US012201633B2

(12) United States Patent
Lassen et al.

(10) Patent No.: US 12,201,633 B2
(45) Date of Patent: Jan. 21, 2025

(54) COMPOUNDS AND METHODS FOR TREATMENT OF VISCERAL PAIN

(71) Applicant: Arena Pharmaceuticals, Inc., New York, NY (US)

(72) Inventors: Cheryl Geraldine Lassen, Zurich (CH); Marcelo Fabian Piccirillo, Cary, NC (US)

(73) Assignee: Arena Pharmaceuticals, Inc., New York, NY (US)

(*) Notice: Subject to any disclaimer, the term of this patent is extended or adjusted under 35 U.S.C. 154(b) by 0 days.

(21) Appl. No.: 17/844,772

(22) Filed: Jun. 21, 2022

(65) Prior Publication Data

US 2023/0033510 A1 Feb. 2, 2023

Related U.S. Application Data

(63) Continuation of application No. 16/611,174, filed as application No. PCT/US2018/031688 on May 8, 2018, now abandoned.

(60) Provisional application No. 62/503,280, filed on May 8, 2017.

(51) Int. Cl.
*A61K 31/497* (2006.01)
*A61P 29/00* (2006.01)

(52) U.S. Cl.
CPC ............ *A61K 31/497* (2013.01); *A61P 29/00* (2018.01)

(58) Field of Classification Search
CPC .................................................. A61K 31/497
See application file for complete search history.

(56) References Cited

U.S. PATENT DOCUMENTS

| | | | |
|---|---|---|---|
| 5,605,906 A | 2/1997 | Lau | |
| 5,971,080 A | 11/1999 | Kikuchi et al. | |
| 5,977,108 A | 11/1999 | Kikuchi et al. | |
| 6,329,402 B1 | 12/2001 | Kikuchi et al. | |
| 6,541,474 B2 | 4/2003 | Kikuchi et al. | |
| 6,630,463 B2 | 10/2003 | Kikuchi et al. | |
| 6,884,808 B2 | 4/2005 | Kikuchi et al. | |
| 7,741,350 B1 | 6/2010 | Luo | |
| 8,778,950 B2 | 7/2014 | Jones | |
| 9,458,136 B2 | 10/2016 | Blackburn | |
| 9,492,447 B2 | 11/2016 | Thatte | |
| 9,597,340 B2 | 3/2017 | Thatte | |
| 9,867,822 B2 | 1/2018 | Thatte | |
| 9,944,606 B2 | 4/2018 | Jones et al. | |
| 10,183,930 B2 | 1/2019 | Blackburn | |
| 10,632,134 B2* | 4/2020 | Thatte | A61K 31/675 |
| 10,981,895 B2* | 4/2021 | Blackburn | A61P 29/00 |
| 11,214,548 B2* | 1/2022 | Jones | C07D 403/12 |
| 11,560,369 B2* | 1/2023 | Blackburn | A61P 29/00 |
| 11,771,695 B2* | 10/2023 | Thatte | A61P 13/12 |
| | | | 514/231.5 |

| | | |
|---|---|---|
| 2003/0079746 A1 | 5/2003 | Hickle |
| 2005/0020544 A1 | 1/2005 | Garzon et al. |
| 2006/0205955 A1 | 9/2006 | Boatman et al. |
| 2007/0041994 A1 | 2/2007 | Kerr et al. |
| 2007/0191362 A1 | 8/2007 | Liotta et al. |
| 2008/0051386 A1 | 2/2008 | Lohray et al. |
| 2008/0064740 A1 | 3/2008 | Bolli et al. |
| 2008/0139635 A1 | 6/2008 | Martin |
| 2010/0160288 A1 | 6/2010 | Astles et al. |
| 2012/0088751 A1 | 4/2012 | Lazzari et al. |
| 2012/0142748 A1 | 6/2012 | Muthuppalaniappan et al. |
| 2013/0165412 A1 | 6/2013 | Jones et al. |
| 2014/0135345 A1 | 5/2014 | Blackburn et al. |
| 2014/0206649 A1 | 7/2014 | Thatte et al. |
| 2015/0126477 A1 | 5/2015 | Thatte et al. |
| 2017/0304327 A1 | 10/2017 | Thatte et al. |
| 2018/0252736 A1 | 9/2018 | Unett et al. |
| 2018/0280386 A1 | 10/2018 | Thatte et al. |
| 2018/0354907 A1 | 12/2018 | Jones et al. |
| 2019/0160058 A1 | 5/2019 | Shanahan |

(Continued)

FOREIGN PATENT DOCUMENTS

| | | |
|---|---|---|
| DE | 102004054666 | 5/2006 |
| EP | 0838453 | 4/2005 |

(Continued)

OTHER PUBLICATIONS

Farrell; Front Pharmacol. 2014, 5, 27. https://doi.org/10.3389%2Ffphar.2014.00027 (Year: 2014).*
Han; ACS Med. Chem. Lett. 2017, 8, 12, 1309-1313. https://doi.org/10.1021/acsmedchemlett.7b00396 (Year: 2017).*
Plan; Clin Pharmacol Ther 2012, 91, 820-828. https://doi.org/10.1038/clpt.2011.301 (Year: 2012).*
"GW pharmaceuticals announces positive preliminary results in a phase III clinical trial with Sativex in 177 patients with severe cancer pain," GW Pharmaceuticals Press Release, Jan. 5, 2019 and Jun. 19, 2007, 5 pages.
"PI3K / Akt Cell Signaling," (2010) www.cellsignal.com.
"Sativex, a canabis-based medicine, significantly reduces central neuropathis pain in people with multiple sclerosis," GW Pharmaceuticals Press Release, Sep. 27, 2005, 2 pages.

(Continued)

*Primary Examiner* — Daniel R Carcanague
(74) *Attorney, Agent, or Firm* — Haley Guiliano LLP; Karen Managasarian; Mihaela D. Danca

(57) ABSTRACT

The present invention relates to certain compounds of Formula Ia and pharmaceutical compositions thereof and their use in methods for the alleviation and/or treatment of visceral pain, for example abdominal pain; pelvic pain; male pelvic pain; pain from an internal organ; bladder pain; painful bladder syndrome; post-surgical abdominal pain (e.g., GI resection, hysterectomy, oophorectomy, C-section, and the like); or pain arising from or related to: pancreatitis (e.g., chronic pancreatitis), prostatitis (e.g., chronic prostatitis), inflammatory bowel disease (e.g., Crohn's disease), endometriosis, interstitial cystitis, prostatitis (e.g., chronic prostatitis), epididymitis (e.g., chronic epididymitis), or post-surgical abdominal lesions. In some embodiments, the visceral pain is consequent to inflammatory bowel disease, for example Crohn's disease.

13 Claims, 13 Drawing Sheets

(56) References Cited

U.S. PATENT DOCUMENTS

| | | | |
|---|---|---|---|
| 2019/0308952 A1 | 10/2019 | Blackburn et al. | |
| 2020/0078358 A1 | 3/2020 | Lassen | |
| 2020/0289458 A1* | 9/2020 | Wong | A61K 9/0014 |
| 2021/0060040 A1* | 3/2021 | Thatte | A61K 45/06 |
| 2022/0306586 A1* | 9/2022 | Jones | A61P 19/02 |

FOREIGN PATENT DOCUMENTS

| | | | |
|---|---|---|---|
| EP | 1177187 | 7/2007 | |
| FR | 2875230 | 3/2006 | |
| WO | WO 97/02244 | 1/1997 | |
| WO | WO 00/64888 | 11/2000 | |
| WO | WO 2004/060882 | 7/2004 | |
| WO | WO 2005/123677 | 12/2005 | |
| WO | WO 2006/025069 | 3/2006 | |
| WO | WO 2006/030124 | 3/2006 | |
| WO | WO 2006/069242 | 6/2006 | |
| WO | WO 2006/129178 | 12/2006 | |
| WO | WO 2008/003665 | 1/2008 | |
| WO | WO 2008/039645 | 4/2008 | |
| WO | WO 2008/048914 | 4/2008 | |
| WO | WO 2008/053341 | 5/2008 | |
| WO | WO 2008/063781 | 5/2008 | |
| WO | WO 2008/064054 | 5/2008 | |
| WO | WO 2008/079316 | 7/2008 | |
| WO | WO 2008/085302 | 7/2008 | |
| WO | WO 2008/109007 | 9/2008 | |
| WO | WO 2008/119694 | 10/2008 | |
| WO | WO 2008/157500 | 12/2008 | |
| WO | WO 2008/157751 | 12/2008 | |
| WO | WO 2009/009550 | 1/2009 | |
| WO | WO 2009/015169 | 1/2009 | |
| WO | WO 2009/025785 | 2/2009 | |
| WO | WO 2010/088050 | 8/2010 | |
| WO | WO 2011/025541 | 3/2011 | |
| WO | WO 2012/116276 | 8/2012 | |
| WO | WO 2012/116277 | 8/2012 | |
| WO | WO 2012/116278 | 8/2012 | |
| WO | WO 2012/116279 | 8/2012 | |
| WO | WO 2016/085941 | 6/2016 | |
| WO | WO 2017/039643 | 3/2017 | |
| WO | WO 2017/180528 | 10/2017 | |
| WO | WO-2018208847 A1 * | 11/2018 | |
| WO | WO-2022187208 A2 * | 9/2022 | A61K 31/497 |
| WO | WO-2023059610 A1 * | 4/2023 | |

OTHER PUBLICATIONS

"The Facts About Inflammatory Bowel Diseases. New York," NY: Crohn's and Colitis Foundation of America, 2014, 24 pages. Downloaded Apr. 19, 2021 from https://www.crohnscolitisfoundation.org/sites/default/files/2019-02/Updated%20IBD%20Factbook.pdf (Year: 2014).

Agarwal et al., "Cannabinoids mediate analgesia largely via peripheral type 1 cannabinoid receptors in nociceptors", Nat. Neurosci., 2007, 10(7):870-879.

Ahmed et al., "Therapeutic Use of Cannabis in Inflammatory Bowel Disease," Gastroenterology and Hepatology, Nov. 2016, 12(11):668-679.

Akhmetshina et al., "The cannabinoid receptor CB2 exerts antifibrotic effects in experimental dermal fibrosis," Arthritis Rheum, 2009, 60:1129-1136.

Alexander et al., "Cannabinoids in the treatment of cancer," Cancer Letters, 2009, 285: 6-12.

Anand et al., "Cannabinoid Receptor CB2 localisation And Agonist-Mediated Inhibition Of Capsaicin Responses In Human Sensory Neurons" Pain, 2008, 138(3):667-680.

Ashton et al., "The cannabinoid CB2 receptor as a target for inflammation-dependent neurodegeneration", Curr. Neuropharmacol., 2007, 5(2):73-80.

Atwood et al., "Functional Selectivity in CB2 Cannabinoid Receptor Signaling and Regulation: Implications for the Therapeutic Potential of CB2 Ligands," Molecular Pharmacology, 2012, 81(2): 250-263.

Baldassarre et al., "The endocannabinoid system in advanced liver cirrhosis: pathophysiological implication and future perspectives," Liver International, 2012, 33(9):1298-1308.

Barutta et al., "Protective Role of Cannabinoid Receptor in Type 2 in a Mouse Model of Diabetic Nephropathy," Diabetes, 2011, 60:2386-2396.

Belvisi et al., "Inhibitory Activity Of The Novel CB2 Receptor Agonist, GW833972A, On Guinea-Pig And Human Sensory Nerve Function In The Airways" British Journal of Pharmacology, 2008 1-11.

Berge et al., "Pharmaceutical salts", J. of Pharm. Sci., 1977, 66:1-19.

Bingham et al., "Species-specific In Vitro Pharmacological Effects Of The Cannabinoid Receptor 2 (CB2) Selective Ligand AM1241 And Its Resolved Enantiomers" British Journal of Pharmacology, 2007, 151:1061-1070.

Boatman et al., "Potent tricyclic pyrazole tetrazole agonists of the nicotinic acid receptor (GPR109a)," Bioorganic & Medicinal Chemistry Letters, 2010, 20: 2797-2800.

Bouaboula et al., "Signaling Pathway Associated With Stimulation Of CB2 Peripheral Cannabinoid Receptor" Eur. J. Biochem., 1996, 237:704-711.

Caffarel et al., "Cannabinoids Reduce ErbB2-Driven Breast Cancer Progression Through Akt Inhibition" Molecular Cancer, 2010, 9:196 and Supplement.

Calignano et al., "Bidirectional control of airway responsiveness by endogenous cannabinoids", Nature, 2000, 408:96-101.

Calignano et al., "Control of pain initiation by endogenous cannabinoids," Nature, 1998, 394:277-281.

Carracedo et al., "Cannabinoids Induce Apoptosis of Pancreatic Tumor Cells via Endoplasmic Reticulum Stress-Related Genes" Cancer Res, 2006, 66:6748-6755.

Casanova et al., "Inhibition Of Skin Tumor Growth And Angiogenesis In Vivo By Activation Of Cannabinoid Receptors" J. Clin. Invest., 2003, 111:43-50.

Chaplan et al., "Quantitative assessment of tactile allodynia in the tat paw", J. Neuroscience Methods, 1994, 531(1):1022-1027.

Cheng et al., "Discovery and Optimization of a Novel Series of N-Arylamide Oxadiazoles as Potent, Highly Selective and Orally Bioavailable Cannabinoid Receptor 2 (CB2) Agonists" J. Med. Chem., 2008, 51:5019-5034.

Collier et al., "Radiosynthesis and in-vivi evaluation of the psuedopeptie δ-opioid antagonist [125I]-1TIPP(Ψ)", J. Labelled Compd. Radiopharm., 1999, 42:S264-S266.

Compton et al., "Aminoalkylindole Analogs: Cannabimimetic Activity of a Class of Compounds Structurally Distinct from A9-Tetrahydrocannabinols" JPET, 1992, 263:1118-1126.

Dhopeshwarkar "cb2 cannabinoid receptors as a therapeutic target-what does the future hold?" Mol. Phar., 2014, 86: 430-437.

Di Marzo et al., "Plant, Synthetic, And Endogenous Cannabinoids In Medicine" Annu. Rev. Med., 2006, 57:553-74.

Di Mauro et al., "Structural Modifications Of N-arylamide Oxadiazoles: Identification Of N-Arylpiperidine Oxadiazoles As Potent And Selective Agonists Of CB2" Bioorganic & Medicinal Chemistry Letters, 2008, 18:4267-4274.

Diaz et al., "Design and Synthesis of a Novel Series of N-Alkyl Isatin Acylhydrazone Derivatives that Act as Selective Cannabinoid Receptor 2 Agonists for the Treatment of Neuropathic Pain" J. Med. Chem., 2008, 51:4932-4947.

Dorwald, "Side Reactions in Organic Synthesis: A Guide to Successful Synthesis Design," Weinhelm: Wiley-VCH Verlag GmbH & Co. KGaA, 2005, Preface.

Dubois et al., "Quantitative validation of voxel-wise statistical analyses of autoradiographic rat brain vols. application to unilateral visual stimulation," J. Cereb. Blood Flow Metab., 2007, 27:1387-96.

Dvorak et al., "Histamine induced responses are attenuated by a cannabinoid receptor agonist in human skin", Inflamm. Res., 2003, 52:238-245.

(56) References Cited

OTHER PUBLICATIONS

El Bakali et al., "Conformational Restriction Leading to a Selective CB2 Cannabinoid Receptor Agonist Orally Active Against Colitis," ACS Med. Chem. Lett. Feb. 2015, 6(2):198-2030.

Ermann et al., "Arylsulfonamide CB2 receptor agonists: SAR and Optimization of CB2 selectivity" Bioorganic & Medicinal Chemistry Letters, 2008, 18:1725-1729.

Furuse et al., "Reduction of bone cancer pain by activation of spinal cannabinoid receptor 1 and its expression in the superficial dorsal horn of the spinal cord in a murine model of bone cancer pain," Anesthesiology, 2009, 111(1):173-86.

Gabriel et al., "High throughput screening technologies for direct cyclic AMP measurement," ASSAY and Drug Development Technologies, 2003, 1:291-303.

Galiegue et al., "Expression Of Central And Peripheral Cannabinoid Receptors In Human Immune Tissues And Leukocyte Subpopulations" Eur. J. Biochem., 1995, 232:54-61.

Gennaro et al., Remington, "The Science and Practice of Pharmacy" 20th Edition, 2000, Lippincott Williams & Wilkins.

Giblin et al., "Discovery of 2-[(2,4-Dichlorophenyl)amino]-N-[(tetrahydro-2H-pyran-4-yl)methyl]-4-(trifluoromethyl)-5-pyrimidinecarboxamide, a Selective CB2 Receptor Agonist for the Treatment of Inflammatory Pain" J. Med. Chem., 2007, 50:2597-2600.

Goncalves et al., "A diacylglycerol lipase-CB2 cannabinoid pathway regulates adult subventricular zone neurogenesis in an age-dependent manner", Mal. Cell Neurosci., 2008, 38(4):526-36.

Goodman et al., "CB2 selective Sulfamoyl Benzamides: Optimization Of The Amide Functionality" Bioorganic & Medicinal Chemistry Letters, 2009, 19:309-313.

Graham et al., "Cannabinoid Receptors: A Brief History And What's Hot" Frontiers in Bioscience, 2009, 14:944-957.

Gratzke et al., "Effects of cannabinor, a novel selective cannabinoid 2 receptor agonist, on bladder function in normal rats," Eur. Urol., 2010, 57:1093-1100, figure 2a-b.

Guillory, "Generation of Polymorphs, Hydrates, Solvates, and Amorphous Solids," in: Polymorphism in Pharmaceutical Solids, ed. Harry G. Britain, 1999, 95:202-209.

Guillot et al., "Cannabinoid receptor 2 counteracts interleukin-17-induced immune and fibrogenic responses in mouse liver," J Hepatology, 2014, 59(1):296-306.

Guindon et al., "Cannabinoid CB2 receptors: a therapeutic target for the treatment of inflammatory and neuropathic pain," Br. J. Pharmacol., 2008, 153:319-334.

Han et al., "Therapeutic utility of cannabinoid receptor type 2 (CB2) selective agonists," Journal of Medicinal Chmeistry, 2013, 56(21):8224-8256.

Hanus et al., (1999) "HU-308: A Specific Agonist For CB2, A Peripheral Cannabinoid Receptor" PNAS, 1999, 96:14228-14233.

Hasenoehrl et al., "Cannabinoids for treating inflammatory bowel diseases: where are we and where do we go?,"Expert Review of Gastroenterology and Hepatology, Apr. 2017, 11(4)329-337.

Hollinshead et al., "Selective Cannabinoid Receptor Type 2 (CB2) Agonists: Optimization of a Series of Purines Leading to the Identification of a Clinical Candidate for the Treatment of Osteoarthritic Pain," J. Med. Chem., 2013, 56:5722-5733.

Hosohata et al., "AM630 Antagonism Of Cannabinoid-Stimulated ["~S]GTP yS Binding In The Mouse Brain" European Journal of Pharmacology, 1997, 321: R1-R3.

Hu et al., "Depression-like behaviour in rats with mononeuropathy is reduced by the CB2-selective agonist GW405833", Pain, 2009, 143:206-212.

Ibn-e-Sina, Abu Ali; A1 Qaanoon fil Tibb, 1987, p. 327. w/ English translation.

Ibrahim et al., "Activation of CB2 cannabinoid receptors by AM1241 inhibits experimental neuropathic pain: pain inhibition by receptors not present in the CNS," Proc. Natl. Acad. Sci., 2003, 100(18):10529-10533.

Ibrahim et al., "CB2 cannabinoid receptor activation produces antinociception by stimulating peripheral release of endogenous opioids", PNAS, 2005, 102(8):3093-8.

Ibrahim et al., "Activation of CB2 cannabinoid receptors by AM1241 inhibits experimental neuropathic pain: pain inhibition by receptors not present in the CNS", Proc. Natl. Aca. Sci., 2003, 100(18):10529-10533.

International Preliminary Report on Patentability in International Appln. No. PCT/US2018/031688, dated Nov. 12, 2019, 7 pages.

International Search Report and Written Opinion in International Appln. No. PCT/US2018/031688, dated Aug. 2, 2018, 10 pages.

Iwata et al., "Identification of a highly potent and selective CB2 agonist, RQ-00202730, for the treatment of irritable bowel syndrome," Bioorganic & Medicinal Chemistry Letters, 2015, 25(2):236-240.

Izzo et al., "Cannabinoids in intestinal inflammation and cancer," Pharmacological Research, 2009, 60(2):117-125.

Johnson et al., Neuroscience poster: A novel selective cB2 agonist, LY28283620 is efficacious in chronic pain models, 2012.

Jordan, "Tamoxifen: a most unlikely pioneering medicine," Nature Reviews: Drug Discovery, 2003, 2:205-213.

Julien et al., "Antifibrogenic role of the cannabinoid receptor CB2 in the liver," Gastroenterology, 2005, 128:742-755.

Kalbhen et al., "Chemical model of osteoarthritis—a pharmacological evaluation," J Rheumatol, 1987, 14:130-1.

Karsak et al., "Attenuation of allergic contact dermatitis through the endocannabinoid system", Science, 2007, 316(5830):1494-1497.

Khan, Mohammad Naimul Ghani; Khazaain al Advia, 1911, Pa 887. w/ English translation.

Khan, Mohammad Najmul Ghani; Khazaain al Advia, 1911, Pa 886. w/ English translation.

Khan, Mohammad Najmul Ghani; Khazaain al Advia, 1911, Pa 889. w/ English translation.

Kikuchi et al., "Pharmacological Evaluation of a Novel Cannabinoid 2 (CB2) Ligand, PF-03550096, In Vitro and In Vivo by Using a Rat Model of Visceral Hypersensitivity," J. Pharmacol. Sci., 2008, 106:219-224.

Kozela et al., "Cannabinoids decrease the th 17 inflammatory autoimmune phenotype," J Neuroimmune Pharmacology, 2013, 8(5):1265-76.

Le Bas et al., "Radioiodinated Analogs of EP 00652218 for the Exploration of the Tachykinin NK1 Receptor by Spect", J. Labelled Compd. Radiopharm., 2001, S280-S282.

Lotersztajn et al., "CB2 receptors as new therapeutic targets for liver diseases," Br J Pharmacol, 2008, 153:286-289.

Lozano-Ondoua et al., "A Cannabinoid 2 Receptor Agonist Attenuates Bone Cancer-Induced Pain And Bone Loss" Life Sciences, 2010, 86:646-653.

Iwata et al., "Identification of a highly potent and selective CB2 agonist, RQ-00202730, for the treatment of irritable bowel syndrome," Bioorg. Med. Chem. Lett., Jan. 2015, 25:236-240.

Majoosi, Ali Ibn-e-Abbass, Kaamil-al-Sena'ah, 2005, p. 303. w/ English translation.

Malan et al., "CB2 cannabinoid receptor-mediated peripheral antinociception", Pain, 2001, 93:239-245.

Mallat et al., "Cannabinoid signaling and liver therapeutics," J Hepatology, 2013, 59(4):891-896.

Manzanares et al., "Role of the cannabinoid system in pain control and therapeutic implications for the management of acute and chronic pain episodes," Current Neuropharmacology, 2006, 4:239-57.

Maresz et al., "Direct suppression of CNS autoimmune inflammation via the cannabinoid receptor CB1 on neurons and CB2 on autoreactive T cells", Nat. Med., 2007, 13(4):492-497.

Markt et al., "Discovery of Novel CB2 Receptor Ligands by a Pharmacophore-Based Virtual Screening Workflow" J. Med. Chem., 2009, 52:369-378.

Marx et al., "Discovery Of a-Amidosulfones As Potent And Selective Agonists Of CB2: Synthesis, SAR, And Pharmacokinetic Properties" Bioorganic & Medicinal Chemistry Letters, 2009, 19:31-35.

Matsuda et al., "Molecular cloning of a human cannabinoid receptor which is also expressed in testis", Nature, 1990, 346:561-564.

(56) References Cited

OTHER PUBLICATIONS

Matsuda et al., "Structure of a cannabinoid receptor and functional expression of the cloned cDNA," Nature, 1990, 346:561-564.
Mbvundula et al., "Arthritis and cannabinoids: HU-210 and Win-55,212-2 prevent IL-1 α-induced matrix degradation in bovine articular chondrocytes in-vitro", J. Pharm. And Pharmacol., 2006, 58:351-358.
McKallip et al., "Targeting CB2 Cannabinoid Receptors As A Novel Therapy To Treat Malignant Lymphoblastic Disease" Blood, 2002, 100:627-634.
Mendez-Sanchez et al., "Endocannabinoid receptor CB2 in nonalcoholic fatty liver disease," Liver International, 2007, 7(2):215-219.
Merriam et al., "Cannabinoid receptor 2 is increased in acutely and chronically inflamed bladder of rats", Neurosci Lett., 2008, 445(1):130-134.
Michalski et al., "Cannabinoids In Pancreatic Cancer: Correlation With Survival And Pain" Int J Cancer., 2008, 122:742-750.
Mitchell et al., "Pyridine-3-carboxamides As Novel CB2 Agonists For Analgesia" Bioorganic & Medicinal Chemistry Letters, 2009, 19:259-263.
Morita et al., "Antitussive effect of WIN 55212-2, a cannabinoid receptor agonist", Eur. J. Pharmacol., 2003, 474:269-272.
Munoz-Lugue et al., "Regression of fibrosis after chronic stimulation of cannabinoid CB2 receptor in cirrhotic rats," J Pharmacol Exp Ther., 2008, 324:475-483.
Munro et al., "Molecular characterization of a peripheral receptor for cannabinoids", Nature, 1993, 365:61-65.
Naguib et al., "MDA7: A Novel Selective Agonist For CB2 Receptors That Prevents Allodynia In Rat Neuropathic Pain Models" British Journal of Pharmacology, 2008, 1-13.
Narayanan et al., "GRC 10622 : A Novel Orally Active CB2 Receptor Agonist With Potential Anti-Hyperalgesic Effects", poster submitted at Society for Neuroscience—Oct. 14-18, 2006, Atlanta, GA, USA.
Ni et al., "Win 55212-2, a cannabinoid receptor agonist, attenuates leukocyte/endothelial interactions in an experimental autoimmune encephalomyelitis model", Mult. Sclerosis, 2004, 10(2):158-64.
Nunez et al., "Cannabinoid CB2 Receptors Are Expressed by Perivascular Microglial Cells in the Human Brain: An Immunohistochemical Study" Synapse, 2004, 53:208-213.
Ofek et al., "Peripheral cannabinoid receptor, CB2, regulates bone mass", PNAS, 2006, 103(3):696-701.
Ohta et al., "I mine Derivatives As New Potent And Selective CB2 Cannabinoid Receptor Agonists With An Analgesic Action" Bioorganic & Medicinal Chemistry, 2008, 16:1111-1124.
Ohta et al., "N-Alkylidenearylcarboxamides As New Potent And Selective CB2 Cannabinoid Receptor Agonists With Good Oral Bioavailability" Bioorganic & Medicinal Chemistry Letters, 2007, 17:6299-6304.
Olea-Herrero et al., "Inhibition of human tumour prostate PC-3 cell growth by cannabinoids R(+)-Methanandamide and JWH-015: Involvement of CB2," British Journal of Cancer, 2009, 101:940-950.
Omura et al., "The SAR Studies of Novel CB2 Selective Agonists, Benzimidazolone Derivatives" Bioorganic & Medicinal Chemistry Letters, 2008, 18(11):3310-3314.
Pacher et al., "The endocannabinoid system as an emerging target of pharmacotherapy", Pharmacol Rev., 2006, 58(3):389-462.
Page et al., "New 1,2,3,4-Tetrahydropyrrolo[3,4-b]indole Derivatives As Selective CB2 Receptor Agonists" Bioorganic & Medicinal Chemistry Letters, 2007, 17:6183-6187.
Page et al., "Novel Benzimidazole Derivatives As Selective CB2 Agonists" Bioorganic & Medicinal Chemistry Letters, 2008, 18:3695-3700.
Palazuelos et al., "The CB(2) cannabinoid receptor controls myeloid progenitor trafficking: involvement in the pathogenesis of an animal model of multiple sclerosis", Biol. Chem., 2008, 283(19):13320-9.
Parfieniuk et al., "Role of cannabinoids in chronic liver diseases," World J Gastroenterol., 2008, 28; 14(40):6109-14.
Pasquini et al., "Investigations on the 4-Quinolone-3-carboxylic Acid Motif. 2. Synthesis and Structure#Activity Relationship of Potent and Selective Cannabinoid- 2 Receptor Agonists Endowed with Analgesic Activity in Vivo" J. Med. Chem., 2008, 51:5075-5084.
Patel et al., "Inhibition of guinea-pig and human sensory nerve activity and the cough reflex in guinea-pigs by cannabinoid (CB2) receptor activation", British J. Pharma., 2003, 140:261-8.
Petrov et al., "Mastering tricyclic ring systems for desirable functional cannabinoid activity," Eur. J. Med. Chem., Nov. 2013, 69: 881-907.
Pisanti et al., "Use Of Cannabinoid Receptor Agonists In Cancer Therapy As Palliative And Curative Agents" Best Practice & Research Clinical Endocrinology & Metabolism, 2009, 23:117-131.
Preet et al., "Cannabinoid Receptors, CB1 and CB2, as Novel Targets for Inhibition of Non- Small Cell Lung Cancer Growth and Metastasis" Published Online First on Nov. 19, 2010 as 10.1158/ 1940-6207.CAPR-10-0181.
Pryce et al., "Cannabinoids inhibit neurodegeneration in models of multiple sclerosis", Brian, 2003, 126:2191-2202.
Richardson et al., "Antihyperalgesic effects of spinal cannabinoids," Eur. J. Pharmacol., 1997, 345:145-153.
Rinaldi-Carmona et al., "SR 144528, the First Potent and Selective Antagonist of the CB2 Cannabinoid Receptor" JPET, 1998, 284:644-650.
Rukwied et al., "Cannabinoid agonists attenuate capsaicin-induced responses in human skin," Pain, 2003, 102:283-288.
Sanchez et al., "Inhibition of Glioma Growth in Vivo by Selective Activation of the CB2 Cannabinoid Receptor" Cancer Research, 2001, 61:5784-5789.
Servettaz et al., "Targeting the cannabinoid pathway limits the development of fibrosis and autoimmunity in a mouse model of systemic sclerosis," Am J Pathol, 2010, 177:187-19.
Sharma et al., "Cell Line-Based Platforms To Evaluate The Therapeutic Efficacy Of Candidate Anticancer Agents" Nature Reviews I Cancer, 2010, 10:241-253.
Shi et al., "Cannabinoid 2 Receptor Induction By IL-12 And Its Potential As A Therapeutic Target For The Treatment Of Anaplastic Thyroid Carcinoma" Cancer Gene Therapy, 2008, 15:101-107.
Slipetz et al., "Activation of the Human Peripheral Cannabinoid Recepto Results in Inhibition of Adenylyl Cyclase" Molecular Pharmacology, 1995, 48:352-361.
Stahly, "Diversity in Single- and Multiple-Component Crystals. The Search for and Prevalence of Polymorphs and Cocrystals", Crystal Growth & Design, 2007, 7(6):1007-1026.
Stansfield et al., "Development Of Carboxylic Acid Replacements In Indole-N-acetamide Inhibitors Of Hepatitis C Virus NS5B Polymerase" Bioorganic & Medicinal Chemistry Letters, 2007, 17:5143-5149.
Steffans et al., "Low dose oral cannabinoid therapy reduces progression of atherosclerosis in mice", Nature, 2005, 434:782-786.
T. Higuchi and V. Stella, Pro-drugs as Novel Delivery Systems vol. 14 of the A.C.S. Symposium Series; and in Bioreversible Carriers in Drug Design, ed. Edward B. Roche, American Pharmaceutical Association and Pergamon Press, 1987.
Tambaro et al., "Evaluation of selective cannabinoid CB(1) and CB(2) receptor agonists in a mouse model of lipopolysaccharide-induced interstitial cystitis", Eur J Pharmacol, 2014, 15(729):67-74.
Trebicka et al., "Role of cannabinoid receptors in alcoholic hepatic injury: steatosis and fibrogenesis are increased in CB2 receptor-deficient mice and decreased in CB1 receptor," Liver Int, 2011, 31:860-870.
Valenzano et al., "Pharmacological And Pharmacokinetic Characterization Of The Cannabinoid Receptor 2 Agonist, GW405833, Utilizing Rodent Models Of Acute And Chronic Pain, Anxiety, Ataxia And Catalepsy" Neuropharmacology, 2003, 48:658-672.
Van Sickle et al., "Identification and Functional Characterization of Brainstem Cannabinoid CB2 Receptors" Science, 2005, 310:329.
Verbist et al., "5-Sulfonyl-benzimidazoles As Selective CB2 Agonists" Bioorganic & Medicinal Chemistry Letters, 2008, 18:2574-2579.
Vincenzi et al., "Antinociceptive effects of the selective CB2 agonist MT178 in inflammatory and chronic rodent pain models," PAIN, Jun. 2013, 154(6):864-873.
Walker and Huang, "Cannabinoid analgesia," Pharmacol. Ther., 2002, 95:127-135.

(56) References Cited

OTHER PUBLICATIONS

Wei et al., "Presence and regulation of cannabinoid receprots in human retinal pigment epithelial cells," Mol. Vis., 2009, 15:1243-51.

Whiteside et al., "The Role of the Cannabinoid CB2 Receptor in Pain Transmission and Therapeutic Potential of Small Molecule CB2 Receptor Agonists" Current Medicinal Chemistry, 2007, 14:917-936.

Widmer et al., "High concentrations of cannabinoids activate apoptosis in human U373MG glioma cells", Neurosci. Res., 2008, 86(14):3212-20.

Worm et al., "Sulfamoyl Benzamides As Novel CB2 Cannabinoid Receptor Ligands" Bioorganic & Medicinal Chemistry Letters, 2008, 18:2830-2835.

Wotherspoon et al., "Peripheral Nerve Injury Induces Cannabinoid Receptor 2 Protein Expression In Rat Sensory Neurons" Neuroscience, 2005, 135:235--245.

Wright et al., "Cannabinoid CB 2 receptors in the gastrointestinal tract: A regulatory system in states of inflammation," British Journal of Pharmacology, Feb. 2008, 153:263-270.

Yan et al., "Cell-based high-throughput screening assay system for monitoring G protein-coupled receptor activation using beta-galactosidase enzyme complementation technology", J. Biomol. Scree, 2002, 7:451-459.

Yao et al., "Characterization of a Cannabinoid CB2 Receptor Selective Agonist, A-836339, in In Vitro Pharmacological assays and In Vivo Pain Models" JPET, 2008, 328(1):141-151.

Yao et al., "In Vitro And In Vivo Characterization Of A-796260: A Selective Cannabinoid CB2 Receptor Agonist Exhibiting Analgesic Activity In Rodent Pain Models" British Journal of Pharmacology, 2008, 153:390-401.

Zhang et al., "Cannabinoid CB(2) receptor activation decreases cerebral infarction in a mouse focal ischemia/reperfusion model", J. Cereb. Blood Flow Metab., 2007, 27:1387-96.

Zhu et al., "Synthesis and mode of action of (125)I- and (3)H-labeled thieno[2,3-c]pyridine antagonists of cell adhesion molecule expression", J. Org. Che., 2002, 67:943-948.

Zindell et al., "Morpholine Containing CB2 Selective Agonists" Bioorganic & Medicinal Chemistry Letters, 2009, 19:1604-1609.

* cited by examiner

Effects of Compound 455 on Body Temperature and Locomotor Activity in Rats

COMPOUNDS AND METHODS FOR TREATMENT OF VISCERAL PAIN

CROSS-REFERENCE TO RELATED APPLICATIONS

This application is a continuation of U.S. application Ser. No. 16/611,174, filed Nov. 5, 2019, which is a national stage application under 35 U.S.C. § 371 of International Application No. PCT/US2018/031688, filed May 8, 2018, which claims priority to U.S. Provisional Application No. 62/503,280, filed on May 8, 2017, the contents of which are incorporated herein by reference in their entirety.

FIELD OF THE INVENTION

The present invention relates to certain compounds of Formula Ia and pharmaceutical compositions thereof and their use in methods for the alleviation and/or treatment of visceral pain, for example abdominal pain; pelvic pain; pain from an internal organ; or pain arising from or related to pancreatitis (e.g., chronic pancreatitis), inflammatory bowel disease, endometriosis, interstitial cystitis, prostatitis (e.g., chronic prostatitis), or post-surgical abdominal lesions. In some embodiments, the visceral pain arises from or is related to inflammatory bowel disease, for example Crohn's disease.

BACKGROUND

Visceral pain is generally the result of damage or injury to internal organs, and is one of the most common forms of pain. Visceral pain is caused by the activation of pain receptors in the chest, abdomen, or pelvic areas, and can be caused by injury or disease states involving the internal organs, such as the stomach, kidney, gallbladder, urinary bladder, and intestines. Visceral pain can also be caused by problems with abdominal muscles and the abdominal wall, such as spasm. Visceral pain is distinct from somatic pain, which is caused by the activation of pain receptors in either the body surface or musculoskeletal tissues (for example, postsurgical pain from a surgical incision), and from neuropathic pain, which is caused by injury or malfunction to the spinal cord and peripheral nerves.

Examples of visceral pain include abdominal pain; pelvic pain; pain from an internal organ; and pain arising from or related to pancreatitis (e.g., chronic pancreatitis), inflammatory bowel disease, endometriosis, interstitial cystitis, prostatitis (e.g., chronic prostatitis), or post-surgical abdominal lesions.

The two main types of inflammatory bowel disease (IBD) are ulcerative colitis (UC), which is limited to the colon, and Crohn's disease (CD), which can affect any segment of the gastrointestinal tract. In both types, the most common symptoms are diarrhea and abdominal pain. Treatments for pain associated with IBD that are currently available have been borrowed from other pain conditions and are not specific for abdominal pain. They include opioids that have the potential for developing tolerance/tachyphylaxis, addiction and abuse, and potentially fatal respiratory depression; gabapentinoids that are safer than opioids but also produce adverse cognitive effects; tricyclic antidepressants that show some efficacy but can also produce somnolence, hypotension, and arrhythmias; and non-steroidal anti-inflammatories (NSAIDs; drugs such as ibuprofen and naproxen) which when administered long term may be associated with an increased risk of gastrointestinal injury/bleeding, cardiac events, hypertension, kidney injury, and death.

Cannabinoids are a group of extracellular signaling molecules. Signals from these molecules are mediated in animals by two G-protein coupled receptors, Cannabinoid Receptor 1 ($CB_1$) and Cannabinoid Receptor 2 ($CB_2$). $CB_1$ is expressed most abundantly in the neurons of the CNS but is also present at lower concentrations in a variety of peripheral tissues and cells (Matsuda, L. A. et al. (1990) *Nature* 346:561-564). In contrast, $CB_2$ is expressed predominantly, although not exclusively, in non-neural tissues, e.g. in hematopoietic cells, endothelial cells, osteoblasts, osteoclasts, the endocrine pancreas, and cancerous cell lines (Munro, S. et al. (1993) *Nature* 365:61-65; and as reviewed in Pacher, P. et al. (2006) *Pharmacol. Rev.* 58(3): 389-462). As such, $CB_1$ is believed to be primarily responsible for mediating the psychotropic effects of cannabinoids on the body, whereas $CB_2$ is believed to be primarily responsible for most of their non-neural effects.

International Patent Application Publication No. WO2011/025541 reports certain compounds of Formula Ia and pharmaceutical compositions thereof that modulate the activity of the $CB_2$ receptor.

There is a need for alternative approaches to targeted pain management for visceral pain, especially for abdominal pain that is poorly managed in IBD due to limited specific options.

BRIEF SUMMARY

It has been discovered in accordance with the present disclosure that Compounds of Formula Ia, for example Compound A, also referred to herein as Compound 699, are particularly useful for the treatment of visceral pain, for example abdominal pain; pelvic pain; male pelvic pain; pain from an internal organ; bladder pain; painful bladder syndrome; post-surgical abdominal pain (e.g., GI resection, hysterectomy, oophorectomy, C-section); or pain associated with: pancreatitis (e.g., chronic pancreatitis), prostatitis (e.g., chronic prostatitis), inflammatory bowel disease (e.g., Crohn's disease), endometriosis, interstitial cystitis, prostatitis (e.g., chronic prostatitis), epididymitis (e.g., chronic epididymitis), or post-surgical abdominal lesions. In some embodiments, the visceral pain arises from or is related to inflammatory bowel disease, for example Crohn's disease. In some embodiments, the interstitial cystitis is interstitial cystitis induced by chemotherapy, ulcerative interstitial cystitis, nonulcerative interstitial cystitis, or autoimmune interstitial cystitis.

Thus, in some embodiments, the present disclosure provides methods for treating or alleviating visceral pain in a patient in need of such treatment, comprising administering to the patient a therapeutically effective amount of a compound selected from compounds of Formula Ia and pharmaceutically acceptable salts and N-oxides thereof:

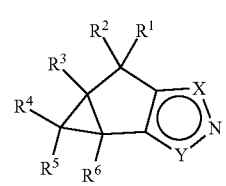

Ia wherein the constituent variables $R^1$-$R^6$, X and Y are as defined below. In some embodiments, the compound of Formula Ia is (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, (Compound A, also referred to herein as Compound 699) having the structure:

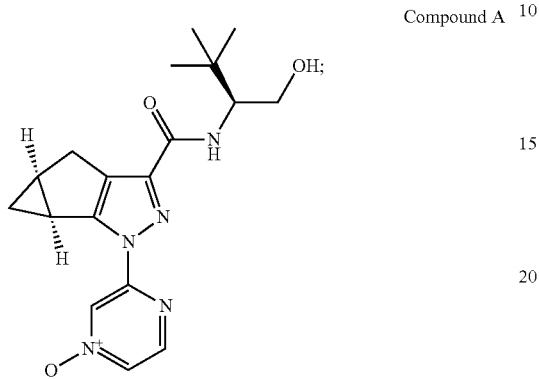

Compound A or a pharmaceutically acceptable salt or crystal form thereof; for example an anhydrous, non-solvated crystalline form.

In some embodiments, the visceral pain is abdominal pain; pain arising from or related to an internal organ; or pain associated with pancreatitis (e.g., chronic pancreatitis), inflammatory bowel disease, endometriosis, interstitial cystitis, prostatitis (e.g., chronic prostatitis), or a post-surgical abdominal lesion. In some embodiments, the visceral pain is pain arising from or related to inflammatory bowel disease, for example pain arising from or related to Crohn's disease.

In some embodiments, the patient is in remission for Crohn's disease, for example where the patient is in remission for Crohn's disease and has chronic visceral pain.

In some embodiments, the patient has previously been treated with an opioid analgesic for pain arising from or related to inflammatory bowel disease, for example Crohn's disease.

In some embodiments, the patient is administered a daily dose of Compound A from 10 mg to 400 mg, from one to three times per day.

In some embodiments, the visceral pain does not arise from or relate to inflammatory bowel disease. In some embodiments, the visceral pain does not arise from or relate to Crohn's disease.

In some embodiments, the present disclosure provides methods for selectively activating a $CB_2$ receptor in a patient experiencing visceral pain, comprising administering to the patient a therapeutically effective amount of a compound selected from compounds of Formula Ia and pharmaceutically acceptable salts and N-oxides thereof, for example Compound A, as described above.

In some embodiments, the present disclosure provides pharmaceutical compositions for alleviation of visceral pain, the compositions comprising a therapeutically effective amount of a compound selected from compounds of Formula Ia and pharmaceutically acceptable salts and N-oxides thereof as described above, for example Compound A.

In some embodiments, the present disclosure provides the use of compounds of Formula Ia and pharmaceutically acceptable salts and N-oxides thereof as described above, for example Compound A, in the manufacture of a medicament for the treatment or alleviation of visceral pain.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

FIG. 13 shows the visceromotor response (VMR) to colorectal distension (CRD) demonstrating enhanced pain responses in rats with colitis relative to naive healthy control rats (i.e., Healthy Control, HC); where open-circles are HC+vehicle (n=11), solid-squares are acute TNBS+vehicle (n=12), solid-circles are acute TNBS+Compound 699 30 gm/kg (n=9), open-squares are HC+Compound 699 30 mg/kg (n=8), and closed-triangles are acute TNBS+Compound 699 10 mg/kg (n=9). See Example 14.

DETAILED DESCRIPTION

Figure 1:
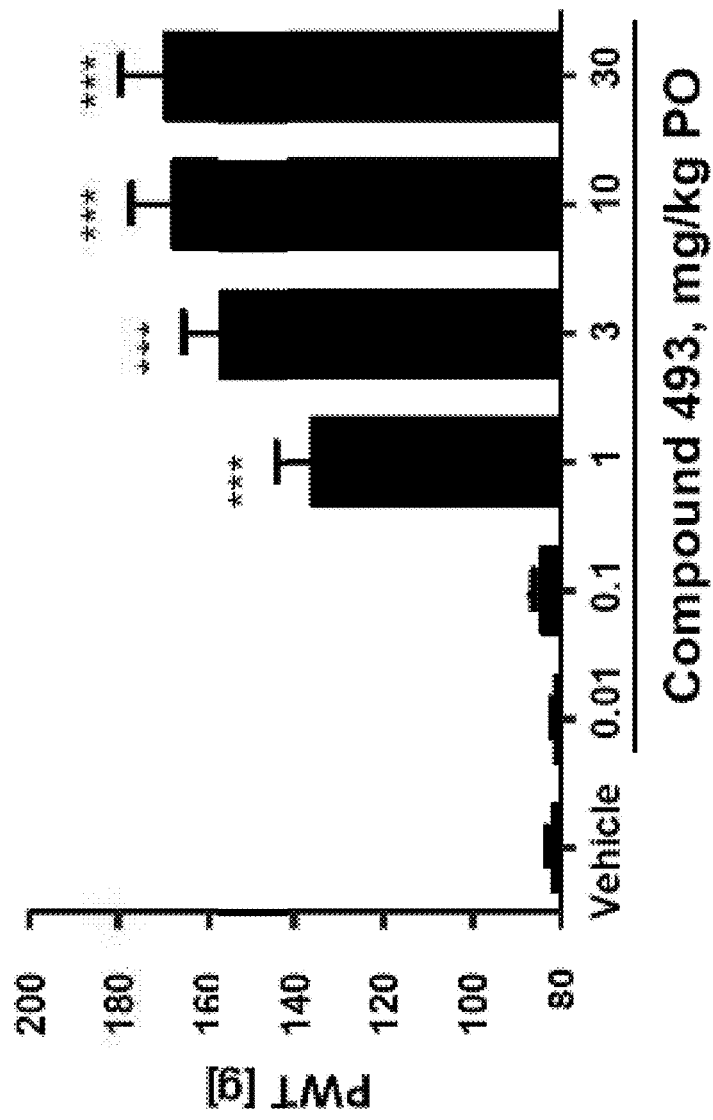
FIG. 1 shows the effect of Compound 493 in the FCA-induced hyperalgesia model of inflammatory pain in rats at 1-hour post dosing. See Example 7.

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The words "treatment" and "treating" are to be understood accordingly as embracing treatment or amelioration of symptoms of disease as well as treatment of the cause of the disease.

The term "patient" may include a human or non-human patient.

It has been discovered in accordance with the present disclosure that Compounds of the general Formula Ia are useful for treating or alleviating visceral pain in a patient in need of such treatment. Thus, in some embodiments the present disclosure provides a method (Method 1) for treating or alleviating visceral pain in a patient in need of such treatment, comprising administering to the patient a therapeutically effective amount of a compound selected from compounds of Formula Ia and pharmaceutically acceptable salts and N-oxides thereof:

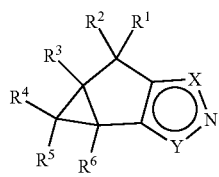

Ia wherein:
- $R^1$, $R^2$, $R^3$, $R^4$, $R^5$, and $R^6$ are each independently selected from: H and $C_1$-$C_6$ alkyl;
- X is $NR^7$ and Y is $CC(O)N(R^8)R^9$; or
- X is $CC(O)N(R^8)R^9$ and Y is $NR^7$;
- $R^7$ is —$R^{10}$—$R^{11}$—$R^{12}$—$R^{13}$; wherein: $R^{10}$ is selected from: $C_1$-$C_6$ alkylene, heteroarylene, and heterocyclylene; or $R^{10}$ is absent;
- $R^{11}$ is selected from: —C(O)NH— and $C_1$-$C_6$ alkylene; or $R^{11}$ is absent;
- $R^{12}$ is $C_1$-$C_6$ alkylene; or $R^{12}$ is absent; and
- $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
- $R^8$ is —$R^{14}$—$R^{15}$—$R^{16}$—$R^{17}$; wherein:
  - $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
  - $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
  - $R^{16}$ is $C_1$-$C_6$ alkylene; or $R^{16}$ is absent; and
  - $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
- $R^9$ is selected from H, $C_1$-$C_6$ alkyl, and $C_3$-$C_7$ cycloalkyl; or
- $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl; for example:

1.1. Method 1, wherein:
- $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent; and
- $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl;

1.2. Method 1, wherein the compound of Formula Ia is selected from compounds of Formula Ic and pharmaceutically acceptable salts, and N-oxides thereof:

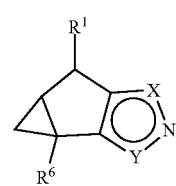

Ic wherein:
R¹ and R⁶ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$;
$R^7$ is $-R^{10}-R^{11}-R^{12}-R^{13}$; wherein:
  $R^{10}$ is selected from: $C_1$-$C_6$ alkylene, heteroarylene, and heterocyclylene; or $R^{10}$ is absent;
  $R^{11}$ is selected from: $-C(O)NH-$ and $C_1$-$C_6$ alkylene; or $R^{11}$ is absent;
  $R^{12}$ is $C_1$-$C_6$ alkylene; or $R^{12}$ is absent; and
  $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is $-R^{14}-R^{15}-R^{16}-R^{17}$; wherein:
  $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
  $R^{15}$ is selected from: $-C(O)NH-$, $-C(O)-$, $-C(O)O-$, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
  $R^{16}$ is $C_1$-$C_6$ alkylene; or $R^{16}$ is absent; and
  $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_8$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl;

1.3. Method 1, wherein the compound of Formula Ia is selected from compounds of Formula Id and pharmaceutically acceptable salts, and N-oxides thereof:

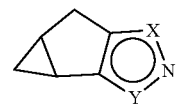

Id wherein:
X is $NR^7$ and Y is $CC(O)NHR^8$; or
X is $CC(O)NHR^8$ and Y is $NR^7$;
$R^7$ is selected from: aryl and heteroaryl; wherein said aryl and heteroaryl are each optionally substituted with one or two substituents selected from: cyano and halogen;
$R^8$ is $-R^{14}-R^{15}-R^{16}-R^{17}$; wherein:
  $R^{14}$ is selected from: $C_1$-$C_6$ alkylene and $C_3$-$C_7$ cycloalkylene; wherein said $C_1$-$C_6$ alkylene is optionally substituted with one or more substituents selected from: $C_1$-$C_6$ alkyl, aryl, heterocyclyl, and hydroxyl; wherein said $C_1$-$C_6$ alkyl is optionally substituted with one substituent selected from: halogen, and hydroxyl; or $R^{14}$ is absent;
  $R^{15}$ is selected from: $-C(O)NH-$ and $-C(O)O-$; or $R^{15}$ is absent;
  $R^{16}$ is $C_1$-$C_6$ alkylene; or $R^{16}$ is absent; and
  $R^{17}$ is selected from: H, $C_1$-$C_6$ alkyl, $C_1$-$C_6$ alkylamino, amino, aryl, carboxy, cyano, $C_1$-$C_6$ haloalkyl, heteroaryl, hydroxyl, and phosphonooxy; wherein said aryl is optionally substituted with one hydroxyl group.

1.4. Method 1, wherein the compound of Formula Ia is selected from compounds of Formula Id and pharmaceutically acceptable salts, and N-oxides thereof:

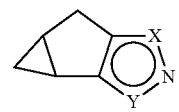

Id wherein:
X is $NR^7$ and Y is $CC(O)NHR^8$; or
X is $CC(O)NHR^8$ and Y is $NR^7$;
$R^7$ is selected from: aryl and heteroaryl; wherein said aryl and heteroaryl are each optionally substituted with one or two substituents selected from: fluoro, chloro, and cyano;
$R^8$ is $-R^{14}-R^{15}-R^{16}-R^{17}$; wherein:
  $R^{14}$ is selected from: $C_1$-$C_6$ alkylene and $C_3$-$C_7$ cycloalkylene; wherein said $C_1$-$C_6$ alkylene is optionally substituted with one or more substituents selected from: tetrahydro-2H-pyranyl, hydroxyl, 2,2,2-trifluoroethyl, and fluoromethyl; or $R^{14}$ is absent;
  $R^{15}$ is selected from: $-C(O)NH-$ and $-C(O)O-$; or $R^{15}$ is absent;

$R^{16}$ is selected from: methylene, isopropyl-methylene, and propylene; or $R^{16}$ is absent; and $R^{17}$ is selected from: H, $C_1$-$C_6$ alkyl, $C_1$-$C_6$ alkylamino, amino, aryl, carboxy, cyano, $C_3$-$C_7$ cycloalkyl, $C_1$-$C_6$ haloalkyl, heteroaryl, heterocyclyl, hydroxyl, and phosphonooxy; wherein said aryl and $C_3$-$C_7$ cycloalkyl are each optionally substituted with one or more substituents selected from hydroxyl and trifluoromethyl.

1.5. Method 1, wherein the compound of Formula Ia is selected from compounds of Formula Id and pharmaceutically acceptable salts, and N-oxides thereof:

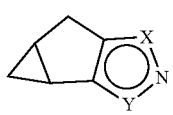

Id wherein:
X is $NR^7$ and Y is $CC(O)NHR^8$; or
X is $CC(O)NHR^8$ and Y is $NR^7$;

$R^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl; and $R^8$ is selected from: 1-hydroxymethyl-2,2-dimethyl-propyl, 2-hydroxy-1,1-dimethyl-ethyl, 1-hydroxymethyl-cyclopropyl, 2-hydroxy-indan-1-yl, 1-hydroxymethyl-cyclobutyl, tert-butyl, 2-hydroxy-1-phenyl-ethyl, 2-hydroxy-1-hydroxymethyl-1-methyl-ethyl, tert-butylamino, 2,2,2-trifluoro-1,1-dimethyl-ethyl, 2-methyl-1-(phosphonooxy)propan-2-yl, 1-methyl-cyclobutyl, 1-hydroxymethyl-2-methyl-propyl, cyano-dimethyl-methyl, 2,2-dimethyl-1-(methyl-carbamoyl)-propyl, 3,3-dimethyl-1-(phosphonooxy)butan-2-yl, 2-hydroxy-1-tetrahydro-pyran-4-yl-ethyl, 1,2-dimethyl-propyl, 1-pyridin-2-yl-cyclobutyl, 2-(methylamino)-2-oxo-1-phenylethyl, 2,2-dimethyl-1-pyridin-2-yl-propyl, 1-methoxy-3,3-dimethyl-1-oxobutan-2-yl, 1-(2-amino-3-methylbutanoyloxy)-3-methylbutan-2-yl, 1-(4-carboxybutanoyloxy)-3-methylbutan-2-yl, 3,3,3-trifluoro-1-hydroxymethyl-propyl, 2-fluoro-1,1-dimethyl-ethyl, 2-fluoro-1-fluoromethyl-1-hydroxymethyl-ethyl, 1-fluoromethyl-2,2-dimethyl-propyl, 1-fluoromethyl-cyclobutyl, 1-trifluoromethyl-cyclopropyl, and 1-trifluoromethyl-cyclobutyl.

1.6. Method 1, wherein the compound of Formula Ia is selected from compounds of Formula Ie and pharmaceutically acceptable salts, and N-oxides thereof:

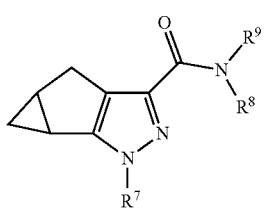

Ie wherein:
$R^7$ is —$R^{10}$—$R^{11}$—$R^{12}$—$R^{13}$; wherein:
$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;

$R^{11}$ is selected from: —C(O)NH— and methylene; or $R^{11}$ is absent;

$R^{12}$ is methylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;

$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl; or $R^{14}$ is absent;

$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl; or $R^{15}$ is absent;

$R^{16}$ is selected from: ethylene and methylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

1.7. Method 1, wherein the compound of Formula Ia is selected from any of Compounds 1-931 disclosed below, and pharmaceutically acceptable salts, and N-oxides thereof, for example any the following compounds, and pharmaceutically acceptable salts, and N-oxides thereof:

(1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

(1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide;

(1aR,5aR)-2-Pyrazin-2-yl-1a,2,5,5a-tetrahydro-1H-2,3-diaza-cyclopropa[a]pentalene-4-carboxylic acid tert-butyl-amide;

(1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

(1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

(1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester;

(1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

(S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

(1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide;

(1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

(1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide;
(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide;
(1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide;
(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;
(1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;
(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and
(1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

1.8. Method 1, wherein the compound of Formula Ia is (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, (Compound A) having the structure:

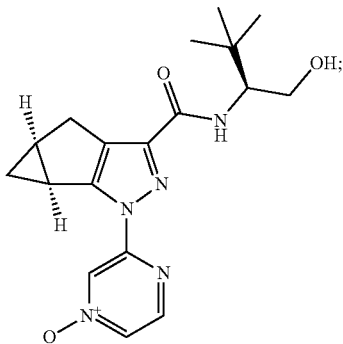

Compound A or a pharmaceutically acceptable salt or crystal form thereof.

1.9. Any Method 1 or 1.1-1.8, wherein the visceral pain is abdominal pain, pelvic pain, pain arising from or related to an internal organ, painful bladder syndrome, pancreatitis (e.g., chronic pancreatitis), inflammatory bowel disease, endometriosis, interstitial cystitis for example interstitial cystitis induced by chemotherapy, ulcerative interstitial cystitis, nonulcerative interstitial cystitis, or autoimmune interstitial cystitis, prostatitis (e.g., chronic prostatitis), or post-surgical abdominal lesion.

1.10. Any Method 1 or 1.1-1.9, wherein the visceral pain is pain arising from or related to inflammatory bowel disease.

1.11. Any Method 1 or 1.1-1.9, wherein the visceral pain is pain arising from or related to Crohn's disease.

1.12. Method 1.11, wherein the patient is in remission for Crohn's disease.

1.13. Method 1.11, wherein the patient is in remission for Crohn's disease and has chronic visceral pain.

1.14. Any Method 1 or 1.1-1.13, wherein the patient has previously been treated with an analgesic for pain arising from or related to inflammatory bowel disease.

1.15. Any Method 1 or 1.1-1.13, wherein the patient has previously been treated with an opioid analgesic for pain arising from or related to Crohn's disease.

1.16. Any Method 1 or 1.1-1.15, wherein the patient is administered a dose from 10 mg to 500 mg of Compound A.

1.17. Any Method 1 or 1.1-1.15, wherein the patient is administered a dose selected from: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg.

1.18. Any Method 1 or 1.1-1.15, wherein the patient is administered a dose from 10 mg to 400 mg of Compound A.

1.19. Any Method 1 or 1.1-1.15, wherein the patient is administered a dose of 25 mg, 50 mg, or 100 mg of Compound A.

1.20. Any Method 1 or 1.16-1.19, wherein the dose is administered once, twice, or three times per day.

1.21. Any Method 1.8-1.20, wherein the Compound A is administered in anhydrous, non-solvated crystalline form.

1.22. Method 1.21, wherein the Compound A displays:
  a powder X-ray diffraction pattern comprising peaks, in terms of 2θ, at 8.5°±0.2°, 10.7°±0.2°, and 16.9°±0.2°;
  a differential scanning calorimetry thermogram comprising an endotherm with an extrapolated onset temperature between about 160.6° C. and about 168.6° C.; and/or
  a thermogravimetric analysis profile showing about 0.25% weight loss below about 135° C.;
or
  a powder X-ray diffraction pattern comprising peaks, in terms of 2θ, at 8.5°±0.2°, 10.7°±0.2°, 16.9°±0.2°, 25.4°±0.2°, and 11.10°±0.2°;
  a differential scanning calorimetry thermogram comprising an endotherm with an extrapolated onset temperature between about 162.6° C. and about 166.6° C.; and/or
  a thermogravimetric analysis profile showing about 0.05% weight loss below about 135° C.;
or
  a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;

a differential scanning calorimetry thermogram comprising an endotherm with an extrapolated onset temperature between about 163.6° C. and about 165.6° C.; and/or a thermogravimetric analysis profile showing about 0.05% weight loss below about 135° C.

or a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;

a differential scanning calorimetry thermogram comprising an endotherm with an extrapolated onset temperature between about 163.6° C. and about 165.6° C.; and/or a thermogravimetric analysis profile showing about 0.05% weight loss below about 135° C.

or a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4° 0.2°, 22.1°±0.2°, and 16.5°±0.2°;

a differential scanning calorimetry thermogram comprising an endotherm with an extrapolated onset temperature at about 164.6° C.; and/or a thermogravimetric analysis profile showing about 0.05% weight loss below about 135° C.

1.23. Any Method 1.8-1.22, wherein the Compound A is administered in a pharmaceutical composition comprising Compound A and a pharmaceutically acceptable carrier.

1.24. Method 1.23, wherein the pharmaceutical composition comprises from 10 mg to 500 mg of Compound A.

1.25. Method 1.23, wherein the patient is administered a dose selected from: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg of Compound A.

1.26. Method 1.23, the pharmaceutical composition comprises from 10 mg to 400 mg of Compound A.

1.27. Method 1.23, the pharmaceutical composition comprises 25 mg, 50 mg, or 100 mg of Compound A.

1.28. Any Method 1.23-1.27, wherein the pharmaceutical composition is administered once, twice, or three times per day.

1.29. Any Method 1 or 1.1-1.28, wherein the patient is administered a pain adjuvant.

1.30. Method 1.29, wherein the pain adjuvant is selected from antidepressants, for example amitriptyline, nortriptyline, venlafaxine, and duloxetine; anti-seizure medications, for example gabapentin, pregabalin, topiramate, lamotrigine, and carbamazepine; muscle relaxants, for example baclofen, cyclobenzaprine, methocarbamol, and diazepam; sleep-inducing medications, for example zopiclone, lorazepam, and temazepam; anti-anxiety medications, for example lorazepam and alprazolam; and botulinum toxin.

1.31. Any Method 1 or 1.1-1.30, wherein the patient is administered an additional active agent.

1.32. Method 1.31, wherein the additional active agent is selected from analgesic agents, and antidiabetic agents.

1.33. Any Method 1, 1.1-1.9 or 1.12-1.32, wherein the visceral pain does not arise from or relate to inflammatory bowel disease.

1.34. Any Method 1, 1.1-1.9 or 1.12-1.32, wherein the visceral pain does not arise from or relate to Crohn's disease.

The disclosure further provides, in one embodiment, a method (Method 2) for selectively activating a CB2 receptor in a patient experiencing visceral pain, comprising administering to the patient a therapeutically effective amount of a compound selected from compounds of Formula Ia and pharmaceutically acceptable salts and N-oxides thereof:

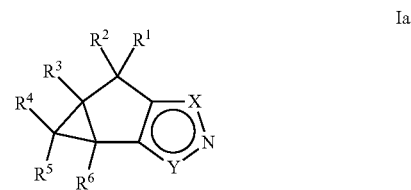

Ia wherein:

$R^1$, $R^2$, $R^3$, $R^4$, $R^5$, and $R^6$ are each independently selected from: H and $C_1$-$C_6$ alkyl;

X is $NR^7$ and Y is $CC(O)N(R^8)R^9$; or

X is $CC(O)N(R^8)R^9$ and Y is $NR^7$;

$R^7$ is —$R^{10}$—$R^{11}$—$R^{12}$—$R^{13}$; wherein:

$R^{10}$ is selected from: $C_1$-$C_6$ alkylene, heteroarylene, and heterocyclylene; or $R^{10}$ is absent;

$R^{11}$ is selected from: —C(O)NH— and $C_1$-$C_6$ alkylene; or $R^{11}$ is absent;

$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_5$ dialkylamino, $C_1$-$C_6$ haloalkyl, halogen, and hydroxyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl; for example:

2.1. Method 2, wherein:
  $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent; and
  $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl;

2.2. Method 2, wherein the compound of Formula Ia is selected from compounds of Formula Ic and pharmaceutically acceptable salts, and N-oxides thereof:

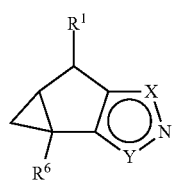

Ic wherein:
  $R^1$ and $R^6$ are each independently selected from: H, and $C_1$-$C_6$ alkyl;
  X is $NR^7$ and Y is $CC(O)N(R^8)R^9$; or
  X is $CC(O)N(R^8)R^9$ and Y is $NR^7$;
  $R^7$ is —$R^{10}$—$R^{11}$—$R^{12}$—$R^{13}$; wherein:
  $R^{10}$ is selected from: $C_1$-$C_6$ alkylene, heteroarylene, and heterocyclylene; or $R^{10}$ is absent;
  $R^{11}$ is selected from: —C(O)NH— and $C_1$-$C_6$ alkylene; or $R^{11}$ is absent;
  $R^{12}$ is $C_1$-$C_6$ alkylene; or $R^{12}$ is absent; and
  $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
  $R^8$ is —$R^{14}$—$R^{15}$—$R^{16}$—$R^{17}$; wherein:
  $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
  $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
  $R^{16}$ is $C_1$-$C_6$ alkylene; or $R^{16}$ is absent; and
  $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
  $R^9$ is selected from H, $C_1$-$C_6$ alkyl, and $C_3$-$C_7$ cycloalkyl; or
  $R^8$ and $R^9$ together with the nitrogen atom to which they are both bonded form a group selected from: heterocyclyl and heterobicyclyl, each optionally substituted with one or more substituents selected from: $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl;

2.3. Method 2, wherein the compound of Formula Ia is selected from compounds of Formula Id and pharmaceutically acceptable salts, and N-oxides thereof:

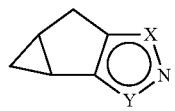

wherein:
X is NR$^7$ and Y is CC(O)NHR$^8$; or
X is CC(O)NHR$^8$ and Y is NR$^7$;
R$^7$ is selected from: aryl and heteroaryl; wherein said aryl and heteroaryl are each optionally substituted with one or two substituents selected from: cyano and halogen;
R$^8$ is —R$^{14}$—R$^{15}$—R$^{16}$—R$^{17}$; wherein:
R$^{14}$ is selected from: C$_1$-C$_6$ alkylene and C$_3$-C$_7$ cycloalkylene; wherein said C$_1$-C$_6$ alkylene is optionally substituted with one or more substituents selected from: C$_1$-C$_6$ alkyl, aryl, heterocyclyl, and hydroxyl; wherein said C$_1$-C$_6$ alkyl is optionally substituted with one substituent selected from: halogen, and hydroxyl; or R$^{14}$ is absent;
R$^{15}$ is selected from: —C(O)NH— and —C(O)O—; or R$^{15}$ is absent;
R$^{16}$ is C$_1$-C$_6$ alkylene; or R$^{16}$ is absent; and
R$^{17}$ is selected from: H, C$_1$-C$_6$ alkyl, C$_1$-C$_6$ alkylamino, amino, aryl, carboxy, cyano, C$_1$-C$_6$ haloalkyl, heteroaryl, hydroxyl, and phosphonooxy; wherein said aryl is optionally substituted with one hydroxyl group.

2.4. Method 2, wherein the compound of Formula Ia is selected from compounds of Formula Id and pharmaceutically acceptable salts, and N-oxides thereof:

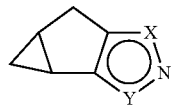

wherein:
X is NR$^7$ and Y is CC(O)NHR$^8$; or
X is CC(O)NHR$^8$ and Y is NR$^7$;
R$^7$ is selected from: aryl and heteroaryl; wherein said aryl and heteroaryl are each optionally substituted with one or two substituents selected from: fluoro, chloro, and cyano;
R$^8$ is —R$^{14}$—R$^{15}$—R$^{16}$—R$^{17}$; wherein:
R$^{14}$ is selected from: C$_1$-C$_6$ alkylene and C$_3$-C$_7$ cycloalkylene; wherein said C$_1$-C$_6$ alkylene is optionally substituted with one or more substituents selected from: tetrahydro-2H-pyranyl, hydroxyl, 2,2,2-trifluoroethyl, and fluoromethyl; or R$^{14}$ is absent;
R$^{15}$ is selected from: —C(O)NH— and —C(O)O—; or R$^{15}$ is absent;
R$^{16}$ is selected from: methylene, isopropyl-methylene, and propylene; or R$^{16}$ is absent; and
R$^{17}$ is selected from: H, C$_1$-C$_6$ alkyl, C$_1$-C$_6$ alkylamino, amino, aryl, carboxy, cyano, C$_3$-C$_7$ cycloalkyl, C$_1$-C$_6$ haloalkyl, heteroaryl, heterocyclyl, hydroxyl, and phosphonooxy; wherein said aryl and C$_3$-C$_7$ cycloalkyl are each optionally substituted with one or more substituents selected from hydroxyl and trifluoromethyl.

2.5. Method 2, wherein the compound of Formula Ia is selected from compounds of Formula Id and pharmaceutically acceptable salts, and N-oxides thereof:

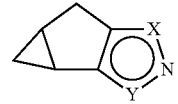

wherein:
X is NR$^7$ and Y is CC(O)NHR$^8$; or
X is CC(O)NHR$^8$ and Y is NR$^7$;
R$^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl; and
R$^8$ is selected from: 1-hydroxymethyl-2,2-dimethyl-propyl, 2-hydroxy-1,1-dimethyl-ethyl, 1-hydroxymethyl-cyclopropyl, 2-hydroxy-indan-1-yl, 1-hydroxymethyl-cyclobutyl, tert-butyl, 2-hydroxy-1-phenyl-ethyl, 2-hydroxy-1-hydroxymethyl-1-methyl-ethyl, tert-butylamino, 2,2,2-trifluoro-1,1-dimethyl-ethyl, 2-methyl-1-(phosphonooxy)propan-2-yl, 1-methyl-cyclobutyl, 1-hydroxymethyl-2-methyl-propyl, cyano-dimethyl-methyl, 2,2-dimethyl-1-(methylcarbamoyl)-propyl, 3,3-dimethyl-1-(phosphonooxy)butan-2-yl, 2-hydroxy-1-tetrahydro-pyran-4-yl-ethyl, 1,2-dimethyl-propyl, 1-pyridin-2-yl-cyclobutyl, 2-(methylamino)-2-oxo-1-phenylethyl, 2,2-dimethyl-1-pyridin-2-yl-propyl, 1-methoxy-3,3-dimethyl-1-oxobutan-2-yl, 1-(2-amino-3-methylbutanoyloxy)-3-methylbutan-2-yl, 1-(4-carboxybutanoyloxy)-3-methylbutan-2-yl, 3,3,3-trifluoro-1-hydroxymethyl-propyl, 2-fluoro-1,1-dimethyl-ethyl, 2-fluoro-1-fluoromethyl-1-hydroxymethyl-ethyl, 1-fluoromethyl-2,2-dimethyl-propyl, 1-fluoromethyl-cyclobutyl, 1-trifluoromethyl-cyclopropyl, and 1-trifluoromethyl-cyclobutyl.

2.6. Method 2, wherein the compound of Formula Ia is selected from compounds of Formula Ie and pharmaceutically acceptable salts, and N-oxides thereof:

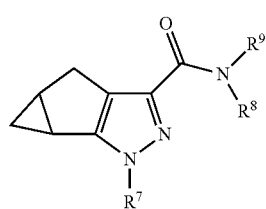

wherein:
R$^7$ is —R$^{10}$—R$^{11}$—R$^{12}$—R$^{13}$; wherein:
R$^{10}$ is selected from: 1,1-dimethylethylene, 1,1-dimethylmethylene, ethylene, methylene, 1,4-piperidinylene, 2,5-pyrazinylene, and 2,4-pyridinylene; or R$^{10}$ is absent;

$R^{11}$ is selected from: —C(O)NH— and methylene; or $R^{11}$ is absent;

$R^{12}$ is methylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl; or $R^{14}$ is absent;

$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl; or $R^{15}$ is absent;

$R^{16}$ is selected from: ethylene and methylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

2.7. Method 2, wherein the compound of Formula Ia is selected from any of Compounds 1-931 disclosed below, and pharmaceutically acceptable salts, and N-oxides thereof, for example any the following compounds, and pharmaceutically acceptable salts, and N-oxides thereof:

(1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

(1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide;

(1aR,5aR)-2-Pyrazin-2-yl-1a,2,5,5a-tetrahydro-1H-2,3-diaza-cyclopropa[a]pentalene-4-carboxylic acid tert-butylamide;

(1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

(1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

(1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester;

(1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

(S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

(1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide;

(1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

(1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

2.8. Method 2, wherein the compound of Formula Ia is (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, (Compound A) having the structure:

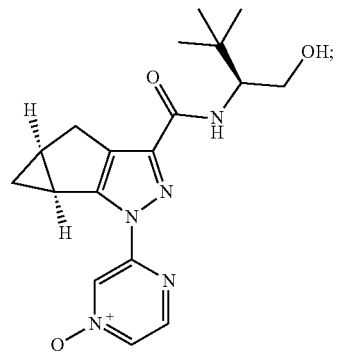

Compound A or a pharmaceutically acceptable salt or crystal form thereof.

2.9. Any Method 2 or 2.1-2.8, wherein the visceral pain is abdominal pain, pelvic pain, pain arising from or related to an internal organ, painful bladder syndrome, pancreatitis (e.g., chronic pancreatitis), inflammatory bowel disease, endometriosis, interstitial cystitis for example interstitial cystitis induced by chemotherapy, ulcerative interstitial cystitis, nonulcerative interstitial cystitis, or autoimmune interstitial cystitis, prostatitis (e.g., chronic prostatitis), or post-surgical abdominal lesion.

2.10. Any Method 2 or 2.1-2.9, wherein the visceral pain is pain arising from or related to inflammatory bowel disease.

2.11. Any Method 2 or 2.1-2.9, wherein the visceral pain is pain arising from or related to Crohn's disease.

2.12. Method 2.11, wherein the patient is in remission for Crohn's disease.

2.13. Method 2.11, wherein the patient is in remission for Crohn's disease and has chronic visceral pain.

2.14. Any Method 2 or 2.1-2.13, wherein the patient has previously been treated with an analgesic for pain arising from or related to inflammatory bowel disease.

2.15. Any Method 2 or 2.1-2.14, wherein the patient has previously been treated with an opioid analgesic for pain arising from or related to Crohn's disease.

2.16. Any Method 2 or 2.1-2.15, wherein the patient is administered a dose from 10 mg to 500 mg of Compound A.

2.17. Any Method 2 or 2.1-2.15, wherein the patient is administered a dose selected from: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg of Compound A.

2.18. Any Method 2 or 2.1-2.15, wherein the patient is administered a daily dose from 10 mg to 400 mg of Compound A.

2.19. Any Method 2 or 2.1-2.15, wherein the patient is administered a dose of 25 mg, 50 mg, or 100 mg of Compound A.

2.20. Any Method 2.16-2.19, wherein the dose is administered once, twice, or three times per day.

2.21. Any Method 2.8-2.20, wherein the Compound A is administered in an anhydrous, non-solvated crystalline form.

2.22. Method 2.21, wherein the Compound A displays:
  a powder X-ray diffraction pattern comprising peaks, in terms of 2θ, at 8.5°±0.2°, 10.7°±0.2°, and 16.9°±0.2°;
  a differential scanning calorimetry thermogram comprising an endotherm with an extrapolated onset temperature between about 160.6° C. and about 168.6° C.; and/or
  a thermogravimetric analysis profile showing about 0.25% weight loss below about 135° C.;
or
  a powder X-ray diffraction pattern comprising peaks, in terms of 2θ, at 8.5°±0.2°, 10.7°±0.2°, 16.9°±0.2°, 25.4°±0.2°, and 11.1°±0.2°; a differential scanning calorimetry thermogram comprising an endotherm with an extrapolated onset temperature between about 162.6° C. and about 166.6° C.; and/or
  a thermogravimetric analysis profile showing about 0.05% weight loss below about 135° C.;
or
  a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;
  a differential scanning calorimetry thermogram comprising an endotherm with an extrapolated onset temperature between about 163.6° C. and about 165.6° C.; and/or
  a thermogravimetric analysis profile showing about 0.05% weight loss below about 135° C.
or
  a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;
  a differential scanning calorimetry thermogram comprising an endotherm with an extrapolated onset temperature between about 163.6° C. and about 165.6° C.; and/or
  a thermogravimetric analysis profile showing about 0.05% weight loss below about 135° C.
or
  a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4° 0.2°, 22.1°±0.2°, and 16.5°±0.2°;
  a differential scanning calorimetry thermogram comprising an endotherm with an extrapolated onset temperature at about 164.6° C.; and/or
  a thermogravimetric analysis profile showing about 0.05% weight loss below about 135° C.

2.23. Any Method 2.8-2.22, wherein the Compound A is administered in a pharmaceutical composition comprising Compound A and a pharmaceutically acceptable carrier.

2.24. Method 2.23, wherein the pharmaceutical composition comprises from 10 mg to 500 mg of Compound A.

2.25. Method 2.23, wherein the pharmaceutical composition comprises 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg of Compound A.

2.26. Method 2.23, the pharmaceutical composition comprises from 10 mg to 400 mg of Compound A.

2.27. Method 2.23, the pharmaceutical composition comprises 25 mg, 50 mg, or 100 mg of Compound A.

2.28. Any Method 2.23-2.27, wherein the pharmaceutical composition is administered once, twice, or three times per day.

2.29. Any Method 2 or 2.1-2.28, wherein the patient is administered a pain adjuvant.

2.30. Method 2.29, wherein the pain adjuvant is selected from antidepressants, for example amitriptyline, nortriptyline, venlafaxine, and duloxetine; anti-seizure medications, for example gabapentin, pregabalin, topiramate, lamotrigine, and carbamazepine; muscle relaxants, for example baclofen, cyclobenzaprine, methocarbamol, and diazepam; sleep-inducing medications, for example zopiclone, lorazepam, and temazapam; anti-anxiety medications, for example lorazepam and alprazolam; and botulinum toxin.

2.31. Any Method 2 or 2.1-2.30, wherein the patient is administered an additional active agent.

2.32. Method 2.31, wherein the additional active agent is selected from analgesic agents, and antidiabetic agents.

2.33. Any Method 2, 2.1-2.9 or 2.12-2.32, wherein the visceral pain does not arise from or relate to inflammatory bowel disease.

2.34. Any Method 2, 2.1-2.9 or 2.12-2.32, wherein the visceral pain does not arise from or relate to Crohn's disease.

The disclosure further provides, in a further embodiment, the use (Use 1) of compounds of Formula Ia and pharmaceutically acceptable salts and N-oxides thereof as described above, for example any of Compounds 1-931 disclosed below, and pharmaceutically acceptable salts, and N-oxides thereof, including for example any the compounds listed in Method 2.7, and pharmaceutically acceptable salts, and N-oxides thereof, for example Compound A, or a pharmaceutically acceptable salt or crystal form thereof, in the manufacture of a medicament for the treatment or alleviation of visceral pain (e.g., in a patient), for example:

1.1. Use 1, wherein the visceral pain is abdominal pain, pelvic pain, pain arising from or related to an internal organ, painful bladder syndrome, pancreatitis (e.g., chronic pancreatitis), inflammatory bowel disease, endometriosis, interstitial cystitis for example interstitial cystitis induced by chemotherapy, ulcerative interstitial cystitis, nonulcerative interstitial cystitis, or autoimmune interstitial cystitis, prostatitis (e.g., chronic prostatitis), or post-surgical abdominal lesion; such as, in a patient.

1.2. Use 1 or 1.1, wherein the visceral pain is pain arising from or related to inflammatory bowel disease.

1.3. Any Use 1 or 1.1-1.2, wherein the visceral pain is pain arising from or related to Crohn's disease.

1.4. Use 1.3, wherein the patient is in remission for Crohn's disease.

1.5. Use 1.3, wherein the patient is in remission for Crohn's disease and has chronic visceral pain.

1.6. Any Use 1 or 1.1-1.5, wherein the patient has previously been treated with an opioid analgesic for pain arising from or related to inflammatory bowel disease.

1.7. Any Use 1 or 1.1-1.5, wherein the patient has previously been treated with an opioid analgesic for pain arising from or related to Crohn's disease.

1.8. Any Use 1 or 1.1-1.7, wherein the patient is administered a dose of 10 mg to 500 mg of Compound A.

1.9. Any Use 1 or 1.1-1.7, wherein the patient is administered a dose selected from: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg of Compound A.

1.10. Any Use 1 or 1.1-1.7, wherein the patient is administered a dose of 10 mg to 400 mg Compound A.

1.11. Any Use 1 or 1.1-1.7, wherein the patient is administered a dose of 25 mg, 50 mg, or 100 mg of Compound A.

1.12. Any Use 1 or 1.1-1.7, wherein the patient is administered a dose once, twice, or three times per day.

1.13. Any Use 1 or 1.1-1.12, wherein the Compound A is administered in an anhydrous, non-solvated crystalline form, for example as described in Method 2.22 above.

1.14. Any Use 1, 1.1 or 1.4-1.13, wherein the visceral pain does not arise from or relate to inflammatory bowel disease.

1.15. Any Use 1, 1.1 or 1.4-1.13, wherein the visceral pain does not arise from or relate to Crohn's disease.

The disclosure further provides, in a further embodiment, a pharmaceutical composition for alleviation of visceral pain (Composition 1), the composition comprising a therapeutically effective amount of a compound selected from compounds of Formula Ia and pharmaceutically acceptable salts and N-oxides thereof as described above, for example Compound A, or a pharmaceutically acceptable salt or crystal form thereof, for example:

1.1. Composition 1, wherein the visceral pain is abdominal pain, pelvic pain, pain arising from or related to an internal organ, painful bladder syndrome, pancreatitis (e.g., chronic pancreatitis), inflammatory bowel disease, endometriosis, interstitial cystitis for example interstitial cystitis induced by chemotherapy, ulcerative interstitial cystitis, nonulcerative interstitial cystitis, or autoimmune interstitial cystitis, prostatitis (e.g., chronic prostatitis), or post-surgical abdominal lesion;

1.2. Composition 1 or 1.1, wherein the visceral pain is pain arising from or related to inflammatory bowel disease.

1.3. Any Composition 1 or 1.1-1.2, wherein the visceral pain is pain arising from or related to Crohn's disease.

1.4. Composition 1.3, wherein the patient is in remission for Crohn's disease.

1.5. Composition 1.3, wherein the patient is in remission for Crohn's disease and has chronic visceral pain.

1.6. Any Composition 1 or 1.1-1.5, wherein the patient has previously been treated with an analgesic for pain arising from or related to inflammatory bowel disease.

1.7. Composition 1 or 1.1-1.5, wherein the patient has previously been treated with an opioid analgesic for pain arising from or related to Crohn's disease.

1.8. Any Composition 1 or 1.1-1.7, wherein the patient is administered a dose of 10 mg to 500 mg of Compound A.

1.9. Any Composition 1 or 1.1-1.7, wherein the patient is administered a dose selected from: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg of Compound A.

1.10. Any Composition 1 or 1.1-1.7, wherein the patient is administered a dose of 10 mg to 400 mg of Compound A.

1.11. Any Composition 1 or 1.1-1.7, wherein the patient is administered a dose of 25 mg, 50 mg, or 100 mg of Compound A.

1.12. Any Composition 1.8-1.11, wherein the patient is administered a dose once, twice, or three times per day.

1.13. Any Composition 1 or 1.1-1.12, wherein the Compound A is administered in anhydrous, non-solvated crystalline form;

1.14. Composition 1.13, wherein the Compound A displays:
a powder X-ray diffraction pattern comprising peaks, in terms of 2θ, at 8.5°±0.2°, 10.7°±0.2°, and 16.9°±0.2°;
a differential scanning calorimetry thermogram comprising an endotherm with an extrapolated onset temperature between about 160.6° C. and about 168.6° C.; and/or
a thermogravimetric analysis profile showing about 0.25% weight loss below about 135° C.;
or
a powder X-ray diffraction pattern comprising peaks, in terms of 2θ, at 8.5°±0.2°, 10.7°±0.2°, 16.9°±0.2°, 25.4°±0.2°, and 11.1°±0.2°;
a differential scanning calorimetry thermogram comprising an endotherm with an extrapolated onset temperature between about 162.6° C. and about 166.6° C.; and/or
a thermogravimetric analysis profile showing about 0.05% weight loss below about 135° C.;
or
a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;

a differential scanning calorimetry thermogram comprising an endotherm with an extrapolated onset temperature between about 163.6° C. and about 165.6° C.; and/or a thermogravimetric analysis profile showing about 0.05% weight loss below about 135° C.

or a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8° 0.2°, and 17.4°±0.2°;

a differential scanning calorimetry thermogram comprising an endotherm with an extrapolated onset temperature between about 163.6° C. and about 165.6° C.; and/or a thermogravimetric analysis profile showing about 0.05% weight loss below about 135° C.

or a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4° 0.2°, 22.1°±0.2°, and 16.5°±0.2°;

a differential scanning calorimetry thermogram comprising an endotherm with an extrapolated onset temperature at about 164.6° C.; and/or a thermogravimetric analysis profile showing about 0.05% weight loss below about 135° C.

1.15. Any Composition 1.1-1.14, wherein the Compound A is administered in a pharmaceutical composition comprising Compound A and a pharmaceutically acceptable carrier.

1.16. Composition 1.15, wherein the pharmaceutical composition comprises from 10 mg to 500 mg of Compound A 1.17. Composition 1.15, wherein the pharmaceutical composition comprises 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg of Compound A.

1.18. Composition 1.15, wherein the pharmaceutical composition comprises from 10 mg to 400 mg of Compound A.

1.19. Composition 1.15, wherein the pharmaceutical composition comprises 25 mg, 50 mg, or 100 mg of Compound A.

1.20. Any Composition 1 or 1.1-1.19, wherein the pharmaceutical composition is administered once, twice, or three times per day.

1.21. Any Composition 1 or 1.1-1.20, wherein the compound of Formula Ia is selected from any of Compounds 1-931 disclosed below, and pharmaceutically acceptable salts, and N-oxides thereof.

1.22. Any Composition 1 or 1.1-1.21, wherein the compound of Formula Ia is selected from any the following compounds, and pharmaceutically acceptable salts, and N-oxides thereof:

(1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

(1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide;

(1aR,5aR)-2-Pyrazin-2-yl-1a,2,5,5a-tetrahydro-1H-2,3-diaza-cyclopropa[a]pentalene-4-carboxylic acid tert-butyl-amide;

(1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

(1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

(1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester;

(1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

(S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

(1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide;

(1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

(1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

1.23. Any Composition 1 or 1.1-1.22, further comprising a pain adjuvant.

1.24. Composition 1.23, wherein the pain adjuvant is selected from antidepressants, for example amitriptyline, nortriptyline, venlafaxine, and duloxetine; anti-seizure medications, for example gabapentin, pregabalin, topiramate, lamotrigine, and carbamazepine; muscle relaxants, for example baclofen, cyclobenzaprine, methocarbamol, and diazepam; sleep-inducing medications, for example zopiclone, lorazepam, and temazapam; anti-anxiety medications, for example lorazepam and alprazolam; and botulinum toxin.

1.25. Any Composition 1 or 1.1-1.24, wherein the patient is administered an additional active agent.

1.26. Composition 1.25, wherein the additional active agent is selected from analgesic agents, and antidiabetic agents.

1.27. Any Composition 1, 1.1-1.3 or 1.6-1.26, wherein the visceral pain does not arise from or relate to inflammatory bowel disease.

1.28. Any Composition 1, 1.1-1.3 or 1.6-1.26, wherein the visceral pain does not arise from or relate to Crohn's disease.

The present disclosure further provides a method (Method 3) of producing a pharmaceutical composition for alleviation of visceral pain in accordance with any Composition 1 or 1.1-1.28, comprising admixing at least one compound selected from compounds of Formula Ia and pharmaceutically acceptable salts and N-oxides thereof as described above, for example any of Compounds 1-931 disclosed below, and pharmaceutically acceptable salts, and N-oxides thereof, including for example, any of the compounds listed in Method 2.7, and pharmaceutically acceptable salts, and N-oxides thereof, for example Compound A, or a pharmaceutically acceptable salt or crystal form thereof, and a pharmaceutically acceptable carrier.

The present disclosure further provides any Method 1 or 1.1-34; Method 2 or 2.1-2.34; Use 1 or 1.1-15; Composition 1 or 1.1-1.28; or Method 3, wherein the pain is mild to moderate pain. The present disclosure further provides any Method 1 or 1.1-34; Method 2 or 2.1-2.34; Use 1 or 1.1-15; Composition 1 or 1.1-1.28; or Method 3, wherein the pain is mild pain.

The present disclosure further provides any Method 1 or 1.1-34; Method 2 or 2.1-2.34; Use 1 or 1.1-15; Composition 1 or 1.1-1.28; or Method 3, wherein the pain is moderate pain.

The present disclosure further provides any Method 1 or 1.1-34; Method 2 or 2.1-2.34; Use 1 or 1.1-15; Composition 1 or 1.1-1.28; or Method 3, wherein the pain is severe pain.

The present disclosure further provides any Method 1 or 1.1-34; Method 2 or 2.1-2.34; Use 1 or 1.1-15; Composition 1 or 1.1-1.28; or Method 3, wherein the pain is moderate to moderately severe pain.

The present disclosure further provides any Method 1 or 1.1-34; Method 2 or 2.1-2.34; Use 1 or 1.1-15; Composition 1 or 1.1-1.28; or Method 3, wherein the pain is moderate to severe pain.

The present disclosure further provides any Method 1 or 1.1-34; Method 2 or 2.1-2.34; Use 1 or 1.1-15; Composition 1 or 1.1-1.28; or Method 3, wherein the patient has a visual analogue scale pain score of ≥40 mm.

The present disclosure further provides any Method 1 or 1.1-34; Method 2 or 2.1-2.34; Use 1 or 1.1-15; Composition 1 or 1.1-1.28; or Method 3, wherein the patient has a Likert numerical rating scale pain score of ≥4.

The present disclosure further provides any Method 1 or 1.1-34; Method 2 or 2.1-2.34; Use 1 or 1.1-15; Composition 1 or 1.1-1.28; or Method 3, wherein the pain is moderate to severe pain requiring continuous, around-the-clock opioid therapy for an extended period of time.

The present disclosure further provides any Method 1 or 1.1-34; Method 2 or 2.1-2.34; Use 1 or 1.1-15; Composition 1 or 1.1-1.28; or Method 3, wherein the pain is acute pain.

The present disclosure further provides any Method 1 or 1.1-34; Method 2 or 2.1-2.34; Use 1 or 1.1-15; Composition 1 or 1.1-1.28; or Method 3, wherein the method is for short-term use (five days or less).

The present disclosure further provides any Method 1 or 1.1-34; Method 2 or 2.1-2.34; Use 1 or 1.1-15; Composition 1 or 1.1-1.28; or Method 3, wherein the pain is chronic visceral pain.

The present disclosure further provides any Method 1 or 1.1-34; Method 2 or 2.1-2.34; Use 1 or 1.1-15; Composition 1 or 1.1-1.28; or Method 3, wherein the compound of Formula Ia is provided in an enterically coated dosage form; a delay release dosage form, or a pulsatile release dosage form.

The present disclosure further provides any Method 1 or 1.1-34; Method 2 or 2.1-2.34; Use 1 or 1.1-15; Composition 1 or 1.1-1.28; or Method 3, wherein the compound is Compound 699, and the pain is abdominal pain, pelvic pain, pain arising from or related to an internal organ, painful bladder syndrome, pancreatitis, chronic pancreatitis, inflammatory bowel disease, endometriosis, interstitial cystitis, interstitial cystitis induced by chemotherapy, ulcerative interstitial cystitis, nonulcerative interstitial cystitis, autoimmune interstitial cystitis, prostatitis, chronic prostatitis, or post-surgical abdominal lesion.

The present disclosure further provides any Method 1 or 1.1-34; Method 2 or 2.1-2.34; Use 1 or 1.1-15; Composition 1 or 1.1-1.28; or Method 3, wherein the compound is Compound 699, and the pain is pain arising from or related to inflammatory bowel disease.

The present disclosure further provides any Method 1 or 1.1-34; Method 2 or 2.1-2.34; Use 1 or 1.1-15; Composition 1 or 1.1-1.28; or Method 3, wherein the compound is Compound 699, and the pain is pain arising from or related to Crohn's disease.

The present disclosure further provides any Method 1 or 1.1-34; Method 2 or 2.1-2.34; Use 1 or 1.1-15; Composition 1 or 1.1-1.28; or Method 3, wherein the compound is administered at one or more initial doses having an initial dosage amount of the compound, and then is subsequently administered at one or more successive doses having a lower dosage amount of the compound. In some embodiments, the initial dose is 100 mg TID and the reduced dose is 50 mg TID; or the initial dose is 25 mg TID and the reduced dose is 25 mg BID.

The present disclosure further provides any foregoing Method, Use or Composition, wherein the visceral pain does not arise from or relate to inflammatory bowel disease.

The present disclosure further provides any foregoing Method, Use or Composition, wherein the visceral pain does not arise from or relate to Crohn's disease.

Preparation of Compounds

The preparation of compounds of Formulas Ia-Id, including Compound A, is described in International Patent Application No. PCT/US2010/002360, published as International Publication No. WO/2011/025541, the entire contents of which are incorporated herein by reference in their entirety.

The preparation of crystal forms of Compound A, including the anhydrous, non-solvated crystalline form, is described in International Patent Application No. PCT/US2012/026506, published as International Publication No. WO2012/116276, the entire contents of which are incorporated herein by reference in their entirety.

Some embodiments of the present disclosure include methods, compositions and uses for every combination of one or more compounds selected from the following group, wherein the Compound Number in bold directly preceding the chemical name is used elsewhere in this disclosure:

Compound 1: (1aR,5aR)-2-(2,4-Difluoro-phenyl)-1a,2,5,5a-tetrahydro-1H-2,3-diaza-cyclopropa[a]pentalene-4-carboxylic acid (2-methyl-2-morpholin-4-yl-propyl)-amide; Compound 2: (1aS,5aS)-2-(2,4-Difluoro-phenyl)-1a,2,5,5a-tetrahydro-1H-2,3-diaza-cyclopropa[a]pentalene-4-carboxylic acid ((R)-1-hydroxymethyl-2,2-dimethyl-propyl)-amide; Compound 3: ((2S,5S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexyl)-carbamic acid tert-butyl ester; Compound 4: (1aR,5aR)-2-(5-Bromo-pyridin-2-yl)-1a,2,5,5a-tetrahydro-1H-2,3-diaza-cyclopropa[a]pentalene-4-carboxylic acid (1-phenyl-cyclopropyl)-amide; Compound 5: (1aR,5aR)-2-(2,4-Difluoro-phenyl)-1a,2,5,5a-tetrahydro-1H-2,3-diaza-cyclopropa[a]pentalene-4-carboxylic acid (5-trifluoromethyl-pyridin-2-yl)-amide; Compound 6: (1aR,5aR)-2-(4-Cyano-phenyl)-1a,2,5,5a-tetrahydro-1H-2,3-diaza-cyclopropa[a]pentalene-4-carboxylic acid (1-methyl-1-phenyl-ethyl)-amide; Compound 7: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-pyrrolidin-3-ylmethyl]-amide; Compound 8: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclopropanecarboxylic acid methyl ester; Compound 9: (4-Cyclohexylmethyl-piperazin-1-yl)-[(1aR,5aR)-2-(2,4-difluoro-phenyl)-1a,2,5,5a-tetrahydro-1H-2,3-diaza-cyclopropa[a]pentalen-4-yl]-methanone; Compound 10: (1aR,5aR)-2-Pyridin-3-yl-1a,2,5,5a-tetrahydro-1H-2,3-diaza-cyclopropa[a]pentalene-4-carboxylic acid (tetrahydro-pyran-4-ylmethyl)-amide; Compound 11: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester; Compound 12: (1aR,5aR)-2-Pyridin-2-yl-1a,2,5,5a-tetrahydro-1H-2,3-diaza-cyclopropa[a]pentalene-4-carboxylic acid [1-(4-fluoro-phenyl)-cyclopropyl]-amide; Compound 13: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-3-ylmethyl)-amide; Compound 14: 1-(2,4-Difluoro-phenyl)-3b,4,4a,5-tetrahydro-1H-cyclopropa[3,4]cyclopenta[1,2-c]pyrazole-3-carboxylic acid ((S)-2-hydroxy-1-phenyl-ethyl)-amide; Compound 15: (1aR,5aR)-2-(2,4-Difluoro-phenyl)-1a,2,5,5a-tetrahydro-1H-2,3-diazacyclopropa[a]pentalene-4-carboxylic acid ((1S,2S,4R)-1,3,3-trimethyl-bicyclo[2.2.1]hept-2-yl)-amide; Compound 16: (1aR,5aR)-2-(2,4-Difluoro-phenyl)-1a,2,5,5a-tetrahydro-1H-2,3-diaza-cyclopropa[a]pentalene-4-carboxylic acid (1-phenyl-cyclopropyl)-amide; Compound 17: (1aS,5aS)-2-(5-Thiazol-2-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 18: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-phenyl-ethyl)-amide; Compound 19: (1aR,5aR)-2-(2,4-Difluoro-phenyl)-1a,2,5,5a-tetrahydro-1H-2,3-diaza-cyclopropa[a]pentalene-4-carboxylic acid [2-(5-hydroxy-1H-indol-3-yl)-ethyl]-amide; Compound 20: (1aR,5aR)-2-(5-Trifluoromethyl-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 21: [(1aR,5aR)-2-(2,4-Difluoro-phenyl)-1a,2,5,5a-tetrahydro-1H-2,3-diaza-cyclopropa[a]pentalen-4-yl]-(S)-hexahydro-pyrrolo[1,2-a]pyrazin-2-yl-methanone; Compound 22: (1aS,5aS)-2-(2,4-Difluoro-phenyl)-1a,2,5,5a-tetrahydro-1H-2,3-diaza-cyclopropa[a]pentalene-4-carboxylic acid (3-chloro-5-methyl-pyridin-2-yl)-amide; Compound 23: (1aS,5aS)-2-(5-o-Tolyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 24: (1aR,5aR)-2-(2,4-Difluoro-phenyl)-1a,2,5,5a-tetrahydro-1H-2,3-diaza-cyclopropa[a]pentalene-4-carboxylic acid (6-fluoro-pyridin-3-yl)-amide; Compound 25: (1aR,5aR)-2-(2,4-Difluoro-phenyl)-1a,2,5,5a-tetrahydro-1H-2,3-diaza-cyclopropa[a]pentalene-4-carboxylic acid [1-(3-fluoro-phenyl)-cyclobutyl]-amide; Compound 26: (1aR,5aR)-2-(2,4-Difluoro-phenyl)-1a,2,5,5a-tetrahydro-1H-2,3-diaza-cyclopropa[a]pentalene-4-carboxylic acid (2-methyl-pyridin-3-yl)-amide; Compound 27: (1aS,5aS)-2-(2,4-Difluoro-phenyl)-1a,2,5,5a-tetrahydro-1H-2,3-diaza-cyclopropa[a]pentalene-4-carboxylic acid [2-hydroxy-1-(tetrahydro-furan-3-yl)-ethyl]-amide; Compound 28: (1aR,5aR)-2-(2,4-Difluoro-phenyl)-1a,2,5,5a-tetrahydro-1H-2,3-diaza-cyclopropa[a]pentalene-4-carboxylic acid [2-(pyridin-3-yloxy)-propyl]-amide; Compound 29: (1aR,5aR)-2-(2,4-Difluoro-phenyl)-1a,2,5,5a-tetrahydro-1H-2,3-diaza-cyclopropa[a]pentalene-4-carboxylic acid ((S)-carbamoyl-phenyl-methyl)-amide; Compound 30: (1aS,5aS)-2-(2,4-Difluoro-phenyl)-1a,2,5,5a-tetrahydro-1H-2,3-diaza-cyclopropa[a]pentalene-4-carboxylic acid (5-fluoro-2-methoxy-phenyl)-amide; Compound 31: (1aR,5aR)-2-(2,4-Difluoro-phenyl)-1a,2,5,5a-tetrahydro-1H-2,3-diaza-cyclopropa[a]pentalene-4-carboxylic acid (2-methoxy-ethyl)-amide; Compound 32: [(1aR,5aR)-2-(2,4-Difluoro-phenyl)-1a,2,5,5a-tetrahydro-1H-2,3-diaza-cyclopropa[a]pentalen-4-yl]-(5,7-dihydro-pyrrolo[3,4-b]pyridin-6-yl)-methanone; Compound 33: (1aS,5aS)-2-(2,4-Difluoro-phenyl)-1a,2,5,5a-tetrahydro-1H-2,3-diaza-cyclopropa[a]pentalene-4-carboxylic acid ((S)-2,3-dihydroxy-propyl)-amide; Compound 34: (S)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-pyrrolidine-1-carboxylic acid tert-butyl ester; Compound 35: (1aS,5aS)-2-(2,4-Difluoro-phenyl)-1a,2,5,5a-tetrahydro-1H-2,3-diaza-cyclopropa[a]pentalene-4-carboxylic acid (2-oxo-2-phenyl-ethyl)-amide; Compound 36: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-azetidin-3-yl]-amide; Compound 37: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-2-yl-ethyl)-amide; Compound 38: [(1aR,5aR)-2-(2,4-Difluoro-phenyl)-1a,2,5,5a-tetrahydro-1H-2,3-diaza-cyclopropa[a]pentalen-4-yl]-(4-methoxy-2,3-dihydro-indol-1-yl)-methanone; Compound 39: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-pyridin-4-yl)-amide; Compound 40: (1aR,5aR)-2-(5-Dimethylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 41: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-4-yl-ethyl)-amide; Compound 42: (1aR,5aR)-2-(2,4-Difluoro-phenyl)-1a,2,5,5a-tetrahydro-1H-2,3-diaza-cyclopropa[a]pentalene-4-carboxylic acid ((R)-1-hydroxymethyl-2-3H-imidazol-4-yl-ethyl)-amide; Compound 43: (1aR,5aR)-2-(2,4-Dichloro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 44: (1aR,5aR)-2-(2,4-Difluoro-phenyl)-1a,2,5,5a-tetrahydro-1H-2,3-diaza-cyclopropa[a]pentalene-4-carboxylic acid 4-hydroxy-3-methoxy-benzylamide; Compound 45: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-oxo-2,3-dihydro-pyrimidin-4-yl)-amide; Compound 46: (1aS,5aS)-2-(2,4-Difluoro-phenyl)-1a,2,5,5a-tetrahydro-1H-2,3-diaza-cyclopropa[a]pentalene-4-carboxylic acid [(R)-1-(4-fluoro-phenyl)-3-hydroxy-propyl]-amide; Compound 47: (1aS,5aS)-2-(2,4-Difluoro-phenyl)-1a,2,5,5a-tetrahydro-1H-2,3-diaza-cyclopropa[a]pentalene-4-carboxylic acid (1-pyridin-4-yl-cyclopropyl)-amide; Compound 48: (1aR,5aR)-2-(5-Isopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 49: [(1aR,5aR)-2-(2,4-Difluoro-phenyl)-1a,2,5,5a-tetrahydro-1H-2,3-diaza-cyclopropa[a]pentalen-4-yl]-((S)-2-phenyl-pyrrolidin-1-yl)-methanone; Compound 50: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1-pyridin-3-yl-ethyl)-amide; Compound 51: [(1aR,5aR)-2-(2,4-Difluoro-phenyl)-1a,2,5,5a-tetrahydro-1H-2,3-diaza-cyclopropa[a]pentalen-4-yl]-(2-pyridin-2-yl-thiomorpholin-4-yl)-methanone; Compound 52: (1aR,5aR)-2-(5-Methyl-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 53: (1aS,5aS)-2-[5-(4-Methoxy-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 54: (1aR,5aR)-2-(2,4-Difluoro-phenyl)-1a,2,5,5a-tetrahydro-1H-2,3-diaza-cyclopropa[a]pentalene-4-carboxylic acid [1,1-dimethyl-2-(4-methyl-piperidin-1-yl)-ethyl]-amide; Compound 55: (1aR,5aR)-2-(2,4-Difluoro-phenyl)-1a,2,5,5a-tetrahydro-1H-2,3-diaza-cyclopropa[a]pentalene-4-carboxylic acid (6-cyano-pyridin-3-yl)-amide; Compound 56: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (5-fluoro-pyridin-2-yl)-amide; Compound 57: (1aR,5aR)-2-(2-Fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 58: (1aR,5aR)-2-(2,4-Difluoro-phenyl)-1a,2,5,5a-tetrahydro-1H-2,3-diaza-cyclopropa[a]pentalene-4-carboxylic acid 2,5-dimethyl-benzylamide; Compound 59: (1aR,5aR)-2-(2,4-Difluoro-phenyl)-1a,2,5,5a-tetrahydro-1H-2,3-diaza-cyclopropa[a]pentalene-4-carboxylic acid (1-isopropyl-piperidin-4-yl)-amide; Compound 60: (1aR,5aR)-2-(2,4-

Difluoro-phenyl)-1a,2,5,5a-tetrahydro-1H-2,3-diaza-cyclopropa[a]pentalene-4-carboxylic acid (2-methoxy-1-methoxymethyl-ethyl)-amide; Compound 61: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclopropyl)-amide; Compound 62: (1aR,5aR)-2-(2,4-Difluoro-phenyl)-1a,2,5,5a-tetrahydro-1H-2,3-diaza-cyclopropa[a]pentalene-4-carboxylic acid 2,3-dimethyl-benzylamide; Compound 63: (1aR,5aR)-2-(2,4-Difluoro-phenyl)-1a,2,5,5a-tetrahydro-1H-2,3-diaza-cyclopropa[a]pentalene-4-carboxylic acid ((R)-1-pyridin-2-yl-ethyl)-amide; Compound 64: (1aS,5aS)-2-(2,4-Difluoro-phenyl)-1a,2,5,5a-tetrahydro-1H-2,3-diaza-cyclopropa[a]pentalene-4-carboxylic acid (1-phenyl-cyclopropyl)-amide; Compound 65: (1aR,5aR)-2-(5-Chloro-pyridin-2-yl)-1a,2,5,5a-tetrahydro-1H-2,3-diaza-cyclopropa[a]pentalene-4-carboxylic acid ((S)-2-hydroxy-1-phenyl-ethyl)-amide; Compound 66: (1aR,5aR)-2-(2,4-Difluoro-phenyl)-1a,2,5,5a-tetrahydro-1H-2,3-diaza-cyclopropa[a]pentalene-4-carboxylic acid (6-chloro-pyridin-3-ylmethyl)-amide; Compound 67: (1aS,5aS)-2-(2,4-Difluoro-phenyl)-1a,2,5,5a-tetrahydro-1H-2,3-diaza-cyclopropa[a]pentalene-4-carboxylic acid (3-methyl-pyridin-2-yl)-amide; Compound 68: (1aS,5aS)-2-(2,4-Difluoro-phenyl)-1a,2,5,5a-tetrahydro-1H-2,3-diaza-cyclopropa[a]pentalene-4-carboxylic acid ((1S,2R)-2-hydroxy-indan-1-yl)-amide; Compound 69: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclobutyl)-amide; Compound 70: (1aR,5aR)-2-(5-Bromo-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 71: (1aR,5aR)-2-tert-Butyl-1a,2,5,5a-tetrahydro-1H-2,3-diaza-cyclopropa[a]pentalene-4-carboxylic acid [2-(4-chloro-phenyl)-1,1-dimethyl-ethyl]-amide; Compound 72: (1aR,5aR)-2-(2,4-Difluoro-phenyl)-1a,2,5,5a-tetrahydro-1H-2,3-diaza-cyclopropa[a]pentalene-4-carboxylic acid (3-hydroxy-pyridin-2-ylmethyl)-amide; Compound 73: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-4-yl)-amide; Compound 74: (1aR,5aR)-2-(2,4-Difluoro-phenyl)-1a,2,5,5a-tetrahydro-1H-2,3-diaza-cyclopropa[a]pentalene-4-carboxylic acid (5-tert-butyl-isoxazol-3-yl)-amide; Compound 75: (1aR,5aR)-2-(2-Methoxy-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 76: (1aR,5aR)-2-(2,2-Dimethyl-propyl)-1a,2,5,5a-tetrahydro-1H-2,3-diaza-cyclopropa[a]pentalene-4-carboxylic acid (1-methyl-1-phenyl-ethyl)-amide; Compound 77: (1aR,5aR)-2-(2,4-Difluoro-phenyl)-1a,2,5,5a-tetrahydro-1H-2,3-diaza-cyclopropa[a]pentalene-4-carboxylic acid [1-(6-methoxy-pyridin-3-yl)-1-methyl-ethyl]-amide; Compound 78: (1aR,5aR)-2-(2,4-Difluoro-phenyl)-1a,2,5,5a-tetrahydro-1H-2,3-diaza-cyclopropa[a]pentalene-4-carboxylic acid (1H-benzoimidazol-2-yl)-amide; Compound 79: (1aR,5aR)-2-(Tetrahydro-pyran-4-ylmethyl)-1a,2,5,5a-tetrahydro-1H-2,3-diaza-cyclopropa[a]pentalene-4-carboxylic acid tert-butylamide; Compound 80: (1aR,5aR)-2-Phenyl-1a,2,5,5a-tetrahydro-1H-2,3-diaza-cyclopropa[a]pentalene-4-carboxylic acid (2-hydroxy-1,1-dimethyl-ethyl)-amide; Compound 81: (1aR,5aR)-2-(2,4-Difluoro-phenyl)-1a,2,5,5a-tetrahydro-1H-2,3-diaza-cyclopropa[a]pentalene-4-carboxylic acid (4-phenyl-thiazol-2-yl)-amide; Compound 82: (1aR,5aR)-2-(Tetrahydro-pyran-4-ylmethyl)-1a,2,5,5a-tetrahydro-1H-2,3-diaza-cyclopropa[a]pentalene-4-carboxylic acid (1-phenyl-cyclopropyl)-amide; Compound 83: (1aR,5aR)-2-(2,4-Difluoro-phenyl)-1a,2,5,5a-tetrahydro-1H-2,3-diaza-cyclopropa[a]pentalene-4-carboxylic acid [1-(2-fluoro-phenyl)-cyclobutyl]-amide; Compound 84: (1aR,5aR)-2-(2,4-Difluoro-phenyl)-1a,2,5,5a-tetrahydro-1H-2,3-diaza-cyclopropa[a]pentalene-4-carboxylic acid 2,4-dimethoxy-benzylamide; Compound 85: (1aR,5aR)-2-(2,4-Difluoro-phenyl)-1a,2,5,5a-tetrahydro-1H-2,3-diaza-cyclopropa[a]pentalene-4-carboxylic acid (5-bromo-3-methyl-pyridin-2-yl)-amide; Compound 86: (1aR,5aR)-2-(2,4-Difluoro-phenyl)-1a,2,5,5a-tetrahydro-1H-2,3-diaza-cyclopropa[a]pentalene-4-carboxylic acid (4-benzyl-morpholin-2-ylmethyl)-amide; Compound 87: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclobutyl)-amide; Compound 88: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 89: (1aR,5aR)-2-(2,4-Difluoro-phenyl)-1a,2,5,5a-tetrahydro-1H-2,3-diaza-cyclopropa[a]pentalene-4-carboxylic acid (6-trifluoromethyl-pyridin-3-ylmethyl)-amide; Compound 90: 6-{[(1aR,5aR)-2-(2,4-Difluoro-phenyl)-1a,2,5,5a-tetrahydro-1H-2,3-diaza-cyclopropa[a]pentalene-4-carbonyl]-amino}-3,4-dihydro-1H-isoquinoline-2-carboxylic acid tert-butyl ester; Compound 91: (1aR,5aR)-2-(2,4-Difluoro-phenyl)-1a,2,5,5a-tetrahydro-1H-2,3-diaza-cyclopropa[a]pentalene-4-carboxylic acid (3R)-(tetrahydro-furan-3-yl)-amide; Compound 92: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclobutanecarboxylic acid ethyl ester; Compound 93: (1aR,5aR)-2-(6-Chloro-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 94: (1aR,5aR)-2-(2,4-Difluoro-phenyl)-1a,2,5,5a-tetrahydro-1H-2,3-diaza-cyclopropa[a]pentalene-4-carboxylic acid (pyridin-3-ylmethyl)-amide; Compound 95: (1aS,5aS)-2-(2,4-Difluoro-phenyl)-1a,2,5,5a-tetrahydro-1H-2,3-diaza-cyclopropa[a]pentalene-4-carboxylic acid pyrazin-2-ylamide; Compound 96: (1aS,5aS)-2-(2,4-Difluoro-phenyl)-1a,2,5,5a-tetrahydro-1H-2,3-diaza-cyclopropa[a]pentalene-4-carboxylic acid ((1R,2S)-2-hydroxy-indan-1-yl)-amide; Compound 97: (1aR,5aR)-2-(5-Trifluoromethyl-pyridin-2-yl)-1a,2,5,5a-tetrahydro-1H-2,3-diaza-cyclopropa[a]pentalene-4-carboxylic acid (1-phenyl-cyclopropyl)-amide; Compound 98: (1aR,5aR)-2-(1-Oxo-hexahydro-1$\lambda^4$-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 99: (1aR,5aR)-2-(2,4-Difluoro-phenyl)-1a,2,5,5a-tetrahydro-1H-2,3-diaza-cyclopropa[a]pentalene-4-carboxylic acid piperidin-4-ylamide; Compound 100: (1aR,5aR)-2-(2,4-Difluoro-phenyl)-1a,2,5,5a-tetrahydro-1H-2,3-diaza-cyclopropa[a]pentalene-4-carboxylic acid [1-(6-hydroxy-pyridin-3-yl)-1-methyl-ethyl]-amide; Compound 101: (1aS,5aS)-2-(2,4-Difluoro-phenyl)-1a,2,5,5a-tetrahydro-1H-2,3-diaza-cyclopropa[a]pentalene-4-carboxylic acid (1-methyl-1-pyridin-2-yl-ethyl)-amide; Compound 102: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclopentyl)-amide; Compound 103: (1aS,5aS)-2-(5-Morpholin-4-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 104: (1aR,5aR)-2-(2,4-Difluoro-phenyl)-1a,2,5,5a-tetrahydro-1H-2,3-diaza-cyclopropa[a]pentalene-4-carboxylic acid (3S)-(1-aza-bicyclo[2.2.2]oct-3-yl)-amide; Compound 105: (1aS,5aS)-2-(2,4-Difluoro-phenyl)-1a,2,5,5a-tetrahydro-1H-2,3-diaza-cyclopropa[a]pentalene-4-carboxylic acid ((R)-2-hydroxy-1-phenyl-ethyl)-amide; Compound 106: (1aS,5aS)-2-(2,4-Difluoro-phenyl)-1a,2,5,5a-tetrahydro-1H-2,3-diaza-cyclopropa[a]pentalene-4-carboxylic acid ((1S,2S)-2-hydroxy-cyclopentyl)-amide; Compound 107: (1aR,5aR)-2-(2,4-Difluoro-phenyl)-1a,2,5,5a-tetrahydro-1H-2,3-diaza-cyclopropa[a]pentalene-4-carboxylic acid [(R)-2-hydroxy-1-((S)-hydroxymethyl)-propyl]-amide; Compound 108: 4-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-piperidine-1-carboxylic acid tert-butyl ester; Compound 109: (1aR,5aR)-2-(2,4-Difluoro-phenyl)-1a,2,5,5a-tetrahydro-1H-2,3-diaza-cyclopropa[a]pentalene-4-carboxylic acid (3,5-dimethoxy-phenyl)-amide; Compound 110: (1aS,5aS)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 111: (1aR,5aR)-2-(5-Trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 112: (1aR,5aR)-2-(2,4-Difluoro-phenyl)-1a,2,5,5a-tetrahydro-1H-2,3-diaza-cyclopropa[a]pentalene-4-carboxylic acid (6-fluoro-4H-benzo[1,3]dioxin-8-ylmethyl)-amide; Compound 113: (1aS,5aS)-2-(2,4-Difluoro-phenyl)-1a,2,5,5a-tetrahydro-1H-2,3-diaza-cyclopropa[a]pentalene-4-carboxylic acid (4,6-dimethyl-pyridin-2-yl)-amide; Compound 114: 1-(2,4-Difluoro-phenyl)-3b,4,4a,5-tetrahydro-1H-cyclopropa[3,4]cyclopenta[1,2-c]pyrazole-3-carboxylic acid (1,1-dimethyl-2-morpholin-4-yl-ethyl)-amide; Compound 115: (1aR,5aR)-2-(6-Bromo-pyridin-3-yl)-1a,2,5,5a-tetrahydro-1H-2,3-diaza-cyclopropa[a]pentalene-4-carboxylic acid (1-phenyl-cyclopropyl)-amide; Compound 116: (1aS,5aS)-2-(2,4-Difluoro-phenyl)-1a,2,5,5a-tetrahydro-1H-2,3-diaza-cyclopropa[a]pentalene-4-carboxylic acid (1-methyl-1-phenyl-ethyl)-amide; Compound 117: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-hydroxy-cyclohexylmethyl)-amide; Compound 118: (1aR,5aR)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclopropyl]-amide; Compound 119: (1aS,5aS)-2-(2,4-Difluoro-phenyl)-1a,2,5,5a-tetrahydro-1H-2,3-diaza-cyclopropa[a]pentalene-4-carboxylic acid ((S)-1-ethyl-pyrrolidin-2-ylmethyl)-amide; Compound 120: (1aR,5aR)-2-tert-Butyl-1a,2,5,5a-tetrahydro-1H-2,3-diaza-cyclopropa[a]pentalene-4-carboxylic acid (S)-indan-1-ylamide; Compound 121: (1aR,5aR)-2-(2,4-Difluoro-phenyl)-1a,2,5,5a-tetrahydro-1H-2,3-diaza-cyclopropa[a]pentalene-4-carboxylic acid pyrimidin-4-ylamide; Compound 122: (1aR,5aR)-2-(2,4-Difluoro-phenyl)-1a,2,5,5a-tetrahydro-1H-2,3-diaza-cyclopropa[a]pentalene-4-carboxylic acid (2-fluoro-4-methanesulfonyl-phenyl)-amide; Compound 123: (1aR,5aR)-2-(5-Methyl-pyridin-2-yl)-1a,2,5,5a-tetrahydro-1H-2,3-diaza-cyclopropa[a]pentalene-4-carboxylic acid (1-phenyl-cyclopropyl)-amide; Compound 124: (1aR,5aR)-2-(5-Methoxy-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 125: (1aR,5aR)-2-(5,6-Difluoro-pyridin-3-yl)-1a,2,5,5a-tetrahydro-1H-2,3-diaza-cyclopropa[a]pentalene-4-carboxylic acid (1-methyl-1-phenyl-ethyl)-amide; Compound 126: (1aR,5aR)-2-(2,4-Difluoro-phenyl)-1a,2,5,5a-tetrahydro-1H-2,3-diaza-cyclopropa[a]pentalene-4-carboxylic acid (6-hydroxy-pyridin-2-yl)-amide; Compound 127: (1aR,5aR)-2-(2,4-Difluoro-phenyl)-1a,2,5,5a-tetrahydro-1H-2,3-diaza-cyclopropa[a]pentalene-4-carboxylic acid cyclobutylamide; Compound 128: (1aS,5aS)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclopropyl]-amide; Compound 129: (1aR,5aR)-2-(6-Methoxy-pyridazin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 130: (1aR,5aR)-2-(2,4-Difluoro-phenyl)-1a,2,5,5a-tetrahydro-1H-2,3-diaza-cyclopropa[a]pentalene-4-carboxylic acid [(S)-1-(3,3,3-trifluoro-propyl)-pyrrolidin-3-yl]-amide; Compound 131: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-pyridin-3-yl)-amide; Compound 132: (1aR,5aR)-2-(2-Chloro-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 133: (1aR,5aR)-2-(2,4-Difluoro-phenyl)-1a,2,5,5a-tetrahydro-1H-2,3-diaza-cyclopropa[a]pentalene-4-carboxylic acid 4-difluoromethoxy-benzylamide; Compound 134: (1aR,5aR)-2-(2,4-Difluoro-phenyl)-1a,2,5,5a-tetrahydro-1H-2,3-diaza-cyclopropa[a]pentalene-4-carboxylic acid (1-piperidin-1-yl-cyclopentylmethyl)-amide; Compound 135: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-3-methyl-butyl)-amide; Compound 136: (1aR,5aR)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclobutyl]-amide; Compound 137: (1aR,5aR)-2-(5-Cyclopropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 138: (1aR,5aR)-2-(2,4-Difluoro-phenyl)-1a,2,5,5a-tetrahydro-1H-2,3-diaza-cyclopropa[a]pentalene-4-carboxylic acid 4-methoxy-benzylamide; Compound 139: (1aR,5aR)-2-(2,4-Difluoro-phenyl)-1a,2,5,5a-tetrahydro-1H-2,3-diaza-cyclopropa[a]pentalene-4-carboxylic acid methyl-pyridin-2-yl-amide; Compound 140: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-phenyl-ethyl)-amide; Compound 141: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid tert-butylamide; Compound 142: (1aR,5aR)-2-(1-Benzyl-piperidin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 143: [(1aR,5aR)-2-(2,4-Difluoro-phenyl)-1a,2,5,5a-tetrahydro-1H-2,3-diaza-cyclopropa[a]pentalen-4-yl]-((R)-2-hydroxymethyl-2,3-dihydro-indol-1-yl)-methanone; Compound 144: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-pyridin-2-yl)-amide; Compound 145: (1aS,5aS)-2-(2,4-Difluoro-phenyl)-1a,2,5,5a-tetrahydro-1H-2,3-diaza-cyclopropa[a]pentalene-4-carboxylic acid (4-dimethylamino-tetrahydro-pyran-4-ylmethyl)-amide; Compound 146: (1aR,5aR)-2-(4-Cyano-phenyl)-1a,2,5,5a-tetrahydro-1H-2,3-diaza-cyclopropa[a]pentalene-4-carboxylic acid (1-phenyl-cyclopropyl)-amide; Compound 147: (1aR,5aR)-2-(6-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 148: (1aR,5aR)-2-tert-Butyl-1a,2,5,5a-tetrahydro-1H-2,3-diaza-cyclopropa[a]pentalene-4-carboxylic acid [2-(4-fluoro-phenyl)-ethyl]-amide; Compound 149: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-piperidin-4-ylmethyl]-amide; Compound 150: (1aS,5aS)-2-(2,4-Difluoro-phenyl)-1a,2,5,5a-tetrahydro-1H-2,3- diaza-cyclopropa[a]pentalene-4-carboxylic acid (6-hydroxy-pyridin-2-yl)-amide; Compound 151: (1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 152: (1aS,5aS)-2-Pyridin-2-yl-1a,2,5,5a-tetrahydro-1H-2,3-diaza-cyclopropa[a]pentalene-4-carboxylic acid (1-phenyl-cyclopropyl)-amide; Compound 153: [(1aR,5aR)-2-(2,4-Difluoro-phenyl)-1a,2,5,5a-tetrahydro-1H-2,3-diaza-cyclopropa[a]pentalen-4-yl]-(4-hydroxy-piperidin-1-yl)-methanone; Compound 154: (1aR,5aR)-2-(2,4-Difluoro-phenyl)-1a,2,5,5a-tetrahydro-1H-2,3-diaza-cyclopropa[a]pentalene-4-carboxylic acid (2-morpholin-4-yl-ethyl)-amide; Compound 155: (1aR,5aR)-2-Pyridin-2-yl-1a,2,5,5a-tetrahydro-1H-2,3-diaza-cyclopropa[a]pentalene-4-carboxylic acid (tetrahydro-pyran-4-ylmethyl)-amide; Compound 156: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1,4-dicarboxylic acid mono-tert-butyl ester; Compound 157: (1aR,5aR)-2-(2,4-Difluoro-phenyl)-1a,2,5,5a-tetrahydro-1H-2,3-diaza-cyclopropa[a]pentalene-4-carboxylic acid (3-hydroxy-pyridin-2-yl)-amide; Compound 158: (1aR,5aR)-2-(2,4-Difluoro-phenyl)-1a,2,5,5a-tetrahydro-1H-2,3-diaza-cyclopropa[a]pentalene-4-carboxylic acid quinolin-3-ylamide; Compound 159: (1aR,5aR)-2-(2-Hydroxy-2-methyl-propyl)-1a,2,5,5a-tetrahydro-1H-2,3-diaza-cyclopropa[a]pentalene-4-carboxylic acid (1-phenyl-cyclopropyl)-amide; Compound 160: (1aR,5aR)-2-(5-Chloro-pyridin-2-yl)-1a,2,5,5a-tetrahydro-1H-2,3-diaza-cyclopropa[a]pentalene-4-carboxylic acid (1-morpholin-4-ylmethyl-cyclopentyl)-amide; Compound 161: (1aR,5aR)-2-(2,4-Difluoro-phenyl)-1a,2,5,5a-tetrahydro-1H-2,3-diaza-cyclopropa[a]pentalene-4-carboxylic acid (1,4-dimethyl-1H-pyrrol-2-ylmethyl)-amide; Compound 162: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-2-yl-ethyl)-amide; Compound 163: 1-(2,4-Difluoro-phenyl)-3b,4,4a,5-tetrahydro-1H-cyclopropa[3,4]cyclopenta[1,2-c]pyrazole-3-carboxylic acid (tetrahydro-pyran-4-ylmethyl)-amide; Compound 164: (1aR,5aR)-2-(4-Fluoro-phenyl)-1a,2,5,5a-tetrahydro-1H-2,3-diaza-cyclopropa[a]pentalene-4-carboxylic acid (1-phenyl-cyclopropyl)-amide; Compound 165: (1aR,5aR)-2-(2,4-Difluoro-phenyl)-1a,2,5,5a-tetrahydro-1H-2,3-diaza-cyclopropa[a]pentalene-4-carboxylic acid pyridin-3-ylamide; Compound 166: (1aR,5aR)-2-(2,4-Difluoro-phenyl)-1a,2,5,5a-tetrahydro-1H-2,3-diaza-cyclopropa[a]pentalene-4-carboxylic acid 2-dimethylamino-benzylamide; Compound 167: (1aR,5aR)-2-(2,4-Difluoro-phenyl)-1a,2,5,5a-tetrahydro-1H-2,3-diaza-cyclopropa[a]pentalene-4-carboxylic acid (tetrahydro-thiopyran-4-yl)-amide; Compound 168: (1aR,5aR)-2-(2,4-Difluoro-phenyl)-1a,2,5,5a-tetrahydro-1H-2,3-diaza-cyclopropa[a]pentalene-4-carboxylic acid (1-m-tolyl-cyclopropyl)-amide; Compound 169: (1aS,5aS)-2-(5-Ethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 170: (1aR,5aR)-2-Isopropyl-1a,2,5,5a-tetrahydro-1H-2,3-diaza-cyclopropa[a]pentalene-4-carboxylic acid (1-methyl-1-phenyl-ethyl)-amide; Compound 171: (1aR,5aR)-2-(2,4-Difluoro-phenyl)-1a,2,5,5a-tetrahydro-1H-2,3-diaza-cyclopropa[a]pentalene-4-carboxylic acid [(S)-1-(2-methoxy-ethyl)-piperidin-3-yl]-amide; Compound 172: (1aR,5aR)-2-(2,4-Difluoro-phenyl)-1a,2,5,5a-tetrahydro-1H-2,3-diaza-cyclopropa[a]pentalene-4-carboxylic acid (5-methoxy-pyridin-2-ylmethyl)-amide; Compound 173: (1aS,5aS)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-4-yl-ethyl)-amide; Compound 174: (1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide; Compound 175: [(1aR,5aR)-2-(2,4-Difluoro-phenyl)-1a,2,5,5a-tetrahydro-1H-2,3-diaza-cyclopropa[a]pentalen-4-yl]-(R)-hexahydro-pyrrolo[1,2-a]pyrazin-2-yl-methanone; Compound 176: (1aR,5aR)-2-(2,4-Difluoro-phenyl)-1a,2,5,5a-tetrahydro-1H-2,3-diaza-cyclopropa[a]pentalene-4-carboxylic acid (4-methyl-pyridin-2-yl)-amide; Compound 177: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-3-fluoro-benzoic acid; Compound 178: (1aR,5aR)-2-Pyridin-2-yl-1a,2,5,5a-tetrahydro-1H-2,3-diaza-cyclopropa[a]pentalene-4-carboxylic acid (2-hydroxy-1,1-dimethyl-ethyl)-amide; Compound 179: (1aS,5aS)-2-(5-Phenyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 180: 2-[(1aR,5aR)-2-(2,4-Difluoro-phenyl)-1a,2,5,5a-tetrahydro-1H-2,3-diaza-cyclopropa[a]pentalene-carbonyl]-1,2,3,4-tetrahydro-isoquinoline-7-carboxylic acid methyl ester; Compound 181: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-pyridin-3-yl)-amide; Compound 182: (1aR,5aR)-2-Pyridin-3-yl-1a,2,5,5a-tetrahydro-1H-2,3-diaza-cyclopropa[a]pentalene-4-carboxylic acid (1-phenyl-cyclopropyl)-amide; Compound 183: (1aR,5aR)-2-(2,4-Difluoro-phenyl)-1a,2,5,5a-tetrahydro-1H-2,3-diaza-cyclopropa[a]pentalene-4-carboxylic acid (1-o-tolyl-cyclobutyl)-amide; Compound 184: (1aR,5aR)-2-(2,4-Difluoro-phenyl)-1a,2,5,5a-tetrahydro-1H-2,3-diaza-cyclopropa[a]pentalene-4-carboxylic acid (1,1-dimethyl-2-pyrrolidin-1-yl-ethyl)-amide; Compound 185: (1aR,5aR)-2-(2,4-Difluoro-phenyl)-1a,2,5,5a-tetrahydro-1H-2,3-diaza-cyclopropa[a]pentalene-4-carboxylic acid (2,6-dimethoxy-pyridin-3-yl)-amide; Compound 186: (1aR,5aR)-2-Pyridin-4-yl-1a,2,5,5a-tetrahydro-1H-2,3-diaza-cyclopropa[a]pentalene-4-carboxylic acid pyridin-2-ylamide; Compound 187: (1aS,5aS)-2-(2,4-Difluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 188: (1aR,5aR)-2-(2,5-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 189: (1aR,5aR)-2-(2,4-Difluoro-phenyl)-1a,2,5,5a-tetrahydro-1H-2,3-diaza-cyclopropa[a]pentalene-4-carboxylic acid [2-(1H-imidazol-4-yl)-ethyl]-amide; Compound 190: (1aR,5aR)-2-(2,4-Difluoro-phenyl)-1a,2,5,5a-tetrahydro-1H-2,3-diaza-cyclopropa[a]pentalene-4-carboxylic acid (3-fluoro-pyridin-4-yl)-amide; Compound 191: (1aR,5aR)-2-(2,4-Dichloro-phenyl)-1a,2,5,5a-tetrahydro-1H-2,3-diaza-cyclopropa[a]pentalene-4-carboxylic acid (1-methyl-1-phenyl-ethyl)-amide; Compound 192: (1aR,5aR)-2-(2,4-Difluoro-phenyl)-1a,2,5,5a-tetrahydro-1H-2,3-diaza-cyclopropa[a]pentalene-4-carboxylic acid ((S)-1-carbamoyl-2-phenyl-ethyl)-amide; Compound 193: (1aR,5aR)-2-(2,4-Difluoro-phenyl)-1a,2,5,5a-tetrahydro-1H-2,3-diaza-cyclopropa[a]pentalene-4-carboxylic acid (oxazol-4-ylmethyl)-amide; Compound 194: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyrimidin-4-yl)-amide; Compound 195: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-hexahydro-1$\lambda^6$-thiopyran-4-yl)-amide; Compound 196:

(1aR,5aR)-2-(4-Cyano-phenyl)-1a,2,5,5a-tetrahydro-1H-2,3-diaza-cyclopropa[a]pentalene-4-carboxylic acid (tetrahydro-pyran-4-ylmethyl)-amide; Compound 197: (1aR,5aR)-2-(3-Fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 198: 2-[((1aR,5aR)-2-tert-Butyl-1a,2,5,5a-tetrahydro-1H-2,3-diaza-cyclopropa[a]pentalene-4-carbonyl)-amino]-3-phenyl-propionic acid methyl ester; Compound 199: (1aR,5aR)-2-(2,4-Difluoro-phenyl)-1a,2,5,5a-tetrahydro-1H-2,3-diaza-cyclopropa[a]pentalene-4-carboxylic acid [(R)-1-(2-methoxy-ethyl)-pyrrolidin-3-yl]-amide; Compound 200: (1aR,5aR)-2-(2,4-Difluoro-phenyl)-1a,2,5,5a-tetrahydro-1H-2,3-diaza-cyclopropa[a]pentalene-4-carboxylic acid [1-(6-methyl-pyridin-2-yl)-ethyl]-amide; Compound 201: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (1-methyl-1-phenyl-ethyl)-amide; Compound 202: (1aR,5aR)-2-Pyrimidin-4-yl-1a,2,5,5a-tetrahydro-1H-2,3-diaza-cyclopropa[a]pentalene-4-carboxylic acid (2-hydroxy-1,1-dimethyl-ethyl)-amide; Compound 203: (1aR,5aR)-2-(2,4-Difluoro-phenyl)-1a,2,5,5a-tetrahydro-1H-2,3-diaza-cyclopropa[a]pentalene-4-carboxylic acid [(R)-2-hydroxy-1-(4-hydroxy-phenyl)-ethyl]-amide; Compound 204: (1aR,5aR)-2-(2,4-Difluoro-phenyl)-1a,2,5,5a-tetrahydro-1H-2,3-diaza-cyclopropa[a]pentalene-4-carboxylic acid (2-methoxy-pyridin-4-yl)-amide; Compound 205: (1aR,5aR)-2-(2,4-Difluoro-phenyl)-1a,2,5,5a-tetrahydro-1H-2,3-diaza-cyclopropa[a]pentalene-4-carboxylic acid (1-pyridin-2-yl-cyclopropyl)-amide; Compound 206: (1aR,5aR)-2-(2-Fluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 207: (R)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester; Compound 208: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-2-ylmethyl)-amide; Compound 209: (1aR,5aR)-2-[2-(Tetrahydro-pyran-4-yl)-ethyl]-1a,2,5,5a-tetrahydro-1H-2,3-diaza-cyclopropa[a]pentalene-4-carboxylic acid (1-methyl-1-phenyl-ethyl)-amide; Compound 210: (1aR,5aR)-2-(3,5-Difluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 211: [(1aR,5aR)-2-(2,4-Difluoro-phenyl)-1a,2,5,5a-tetrahydro-1H-2,3-diaza-cyclopropa[a]pentalen-4-yl]-(7-methoxy-3,4-dihydro-1H-isoquinolin-2-yl)-methanone; Compound 212: (1aR,5aR)-2-(2,4-Difluoro-phenyl)-1a,2,5,5a-tetrahydro-1H-2,3-diaza-cyclopropa[a]pentalene-4-carboxylic acid (3-fluoro-pyridin-2-yl)-amide; Compound 213: 1-(2,4-Difluoro-phenyl)-3b,4,4a,5-tetrahydro-1H-cyclopropa[3,4]cyclopenta[1,2-c]pyrazole-3-carboxylic acid (1-phenyl-cyclopropyl)-amide; Compound 214: (1aR,5aR)-2-(2-Fluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 215: [(1aR,5aR)-2-(2,4-Difluoro-phenyl)-1a,2,5,5a-tetrahydro-1H-2,3-diaza-cyclopropa[a]pentalen-4-yl]-(1,4,6,7-tetrahydro-imidazo[4,5-c]pyridin-5-yl)-methanone; Compound 216: (1aR,5aR)-2-(2,4-Difluoro-phenyl)-1a,2,5,5a-tetrahydro-1H-2,3-diaza-cyclopropa[a]pentalene-4-carboxylic acid (5-fluoro-pyridin-2-yl)-amide; Compound 217: 3-{[(1aS,5aS)-2-(2,4-Difluoro-phenyl)-1a,2,5,5a-tetrahydro-1H-2,3-diaza-cyclopropa[a]pentalene-4-carbonyl]-amino}-3-(R)-pyridin-3-yl-propionic acid; Compound 218: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-methyl-ethyl)-amide; Compound 219: (1aR,5aR)-2-Pyrazin-2-yl-1a,2,5,5a-tetrahydro-1H-2,3-diaza-cyclopropa[a]pentalene-4-carboxylic acid (4-hydroxymethyl-tetrahydro-pyran-4-yl)-amide; Compound 220: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-phenyl-ethyl)-amide; Compound 221: (1aS,5aS)-2-(2,4-Difluoro-phenyl)-1a,2,5,5a-tetrahydro-1H-2,3-diaza-cyclopropa[a]pentalene-4-carboxylic acid [(S)-1-(4-fluoro-phenyl)-3-hydroxy-propyl]-amide; Compound 222: 1-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexanecarboxylic acid methyl ester; Compound 223: (1aR,5aR)-2-(Tetrahydro-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 224: [(1aR,5aR)-2-(2,4-Difluoro-phenyl)-1a,2,5,5a-tetrahydro-1H-2,3-diaza-cyclopropa[a]pentalen-4-yl]-((R)-2-phenyl-pyrrolidin-1-yl)-methanone; Compound 225: ((1R,2R)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexyl)-carbamic acid tert-butyl ester; Compound 226: (1aS,5aS)-2-(2,4-Difluoro-phenyl)-1a,2,5,5a-tetrahydro-1H-2,3-diaza-cyclopropa[a]pentalene-4-carboxylic acid (5-bromo-3-methyl-pyridin-2-yl)-amide; Compound 227: (1aR,5aR)-2-(2,4-Difluoro-phenyl)-1a,2,5,5a-tetrahydro-1H-2,3-diaza-cyclopropa[a]pentalene-4-carboxylic acid amide; Compound 228: (1aS,5aS)-2-(5-p-Tolyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 229: (1aR,5aR)-2-(2,4-Difluoro-phenyl)-1a,2,5,5a-tetrahydro-1H-2,3-diaza-cyclopropa[a]pentalene-4-carboxylic acid (S)-indan-1-ylamide; Compound 230: (1aR,5aR)-2-(2,4-Difluoro-phenyl)-1a,2,5,5a-tetrahydro-1H-2,3-diaza-cyclopropa[a]pentalene-4-carboxylic acid (3-hydroxymethyl-pyridin-4-yl)-amide; Compound 231: (1aR,5aR)-2-Pyridin-4-yl-1a,2,5,5a-tetrahydro-1H-2,3-diaza-cyclopropa[a]pentalene-4-carboxylic acid (1-phenyl-cyclopropyl)-amide; Compound 232: (1aR,5aR)-2-(4-Fluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 233: (1aR,5aR)-2-(2,4-Difluoro-phenyl)-1a,2,5,5a-tetrahydro-1H-2,3-diaza-cyclopropa[a]pentalene-4-carboxylic acid (3-dimethylamino-tetrahydro-thiophen-3-ylmethyl)-amide; Compound 234: (1aR,5aR)-2-(2,4-Difluoro-phenyl)-1a,2,5,5a-tetrahydro-1H-2,3-diaza-cyclopropa[a]pentalene-4-carboxylic acid (tetrahydro-pyran-4-yl)-amide; Compound 235: (1aR,5aR)-2-(2,4-Difluoro-phenyl)-1a,2,5,5a-tetrahydro-1H-2,3-diaza-cyclopropa[a]pentalene-4-carboxylic acid (5-chloro-pyridin-2-yl)-amide; Compound 236: (1aS,5aS)-2-(2,4-Difluoro-phenyl)-1a,2,5,5a-tetrahydro-1H-2,3-diaza-cyclopropa[a]pentalene-4-carboxylic acid (1-carbamoyl-cyclobutyl)-amide; Compound 237: (1aR,5aR)-2-(2,4-Difluoro-phenyl)-1a,2,5,5a-tetrahydro-1H-2,3-diaza-cyclopropa[a]pentalene-4-carboxylic acid 5-fluoro-2-methyl-benzylamide; Compound 238: (1aR,5aR)-2-(2,4-Difluoro-phenyl)-1a,2,5,5a-tetrahydro-1H-2,3-diaza-cyclopropa[a]pentalene-4-carboxylic acid (2-morpholin-4-yl-2-pyridin-3-yl-ethyl)-amide; Compound 239: (1aR,5aR)-2-(4-Methoxy-phenyl)-1a,2,5,5a-tetrahydro-1H-2,3-diaza-cyclopropa[a]pentalene-4-carboxylic acid (1-methyl-1-phenyl-ethyl)-amide; Compound 240: (1aR,5aR)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclobutyl]-amide; Compound 241: [(1aR,5aR)-2-

(2,4-Difluoro-phenyl)-1a,2,5,5a-tetrahydro-1H-2,3-diaza-cyclopropa[a]pentalen-4-yl]-(5-fluoro-1,3-dihydro-isoindol-2-yl)-methanone; Compound 242: (1aS,5aS)-2-(2,4-Difluoro-phenyl)-1a,2,5,5a-tetrahydro-1H-2,3-diaza-cyclopropa[a]pentalene-4-carboxylic acid (5-methyl-pyridin-2-yl)-amide; Compound 243: (1aR,5aR)-2-(2,4-Difluoro-phenyl)-1a,2,5,5a-tetrahydro-1H-2,3-diaza-cyclopropa[a]pentalene-4-carboxylic acid [(S)-1-(tetrahydro-furan-2-yl)methyl]-amide; Compound 244: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclopentyl)-amide; Compound 245: (1aR,5aR)-2-(2,4-Difluoro-phenyl)-1a,2,5,5a-tetrahydro-1H-2,3-diaza-cyclopropa[a]pentalene-4-carboxylic acid (1-dimethylaminomethyl-cyclopentyl)-amide; Compound 246: (1aR,5aR)-2-tert-Butyl-1a,2,5,5a-tetrahydro-1H-2,3-diaza-cyclopropa[a]pentalene-4-carboxylic acid [2-(4-fluoro-phenyl)-1-methyl-ethyl]-amide; Compound 247: [(1aR,5aR)-2-(2,4-Difluoro-phenyl)-1a,2,5,5a-tetrahydro-1H-2,3-diaza-cyclopropa[a]pentalen-4-yl]-(3-hydroxy-7,8-dihydro-5H-[1,6]naphthyridin-6-yl)-methanone; Compound 248: (1aR,5aR)-2-(2,4-Difluoro-phenyl)-1a,2,5,5a-tetrahydro-1H-2,3-diaza-cyclopropa[a]pentalene-4-carboxylic acid benzothiazol-2-ylamide; Compound 249: (1aR,5aR)-2-(2,4-Difluoro-phenyl)-1a,2,5,5a-tetrahydro-1H-2,3-diaza-cyclopropa[a]pentalene-4-carboxylic acid [1-(2-fluoro-phenyl)-cyclopropyl]-amide; Compound 250: (1aR,5aR)-2-(Tetrahydro-pyran-4-ylmethyl)-1a,2,5,5a-tetrahydro-1H-2,3-diaza-cyclopropa[a]pentalene-4-carboxylic acid (2-hydroxy-1,1-dimethyl-ethyl)-amide; Compound 251: (1aR,5aR)-2-(2-Morpholin-4-yl-ethyl)-1a,2,5,5a-tetrahydro-1H-2,3-diaza-cyclopropa[a]pentalene-4-carboxylic acid (1-methyl-1-phenyl-ethyl)-amide; Compound 252: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-piperidin-4-yl]-amide; Compound 253: 4-[(1aR,5aR)-2-(2,4-Difluoro-phenyl)-1a,2,5,5a-tetrahydro-1H-2,3-diaza-cyclopropa[a]pentalene-4-carbonyl]-3-hydroxymethyl-piperazine-1-carboxylic acid (S)-tert-butyl ester; Compound 254: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-4-yl-ethyl)-amide; Compound 255: (1aR,5aR)-2-(5-Cyano-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 256: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-azetidin-3-ylmethyl]-amide; Compound 257: (1aR,5aR)-2-(2,4-Difluoro-phenyl)-1a,2,5,5a-tetrahydro-1H-2,3-diaza-cyclopropa[a]pentalene-4-carboxylic acid (6-pyrrolidin-1-yl-pyridin-2-ylmethyl)-amide; Compound 258: (1aR,5aR)-2-(Tetrahydro-pyran-4-ylmethyl)-1a,2,5,5a-tetrahydro-1H-2,3-diaza-cyclopropa[a]pentalene-4-carboxylic acid (5-fluoro-pyridin-2-yl)-amide; Compound 259: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-tetrahydro-1$\lambda^6$-thiophen-3-yl)-amide; Compound 260: (1aR,5aR)-2-(2,4-Difluoro-phenyl)-1a,2,5,5a-tetrahydro-1H-2,3-diaza-cyclopropa[a]pentalene-4-carboxylic acid 2,3-dimethoxy-benzylamide; Compound 261: (1aR,5aR)-2-(2,4-Difluoro-phenyl)-1a,2,5,5a-tetrahydro-1H-2,3-diaza-cyclopropa[a]pentalene-4-carboxylic acid (3-cyano-5-methyl-pyridin-2-yl)-amide; Compound 262: (1aR,5aR)-2-(2,4-Difluoro-phenyl)-1a,2,5,5a-tetrahydro-1H-2,3-diaza-cyclopropa[a]pentalene-4-carboxylic acid (2,3-dihydro-benzofuran-3-yl)-amide; Compound 263: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclohexyl)-amide; Compound 264: (1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 265: (1aR,5aR)-2-(2,4-Difluoro-phenyl)-1a,2,5,5a-tetrahydro-1H-2,3-diaza-cyclopropa[a]pentalene-4-carboxylic acid 2,5-difluoro-benzylamide; Compound 266: (1aS,5aS)-2-(2,4-Difluoro-phenyl)-1a,2,5,5a-tetrahydro-1H-2,3-diaza-cyclopropa[a]pentalene-4-carboxylic acid 4-dimethylamino-benzylamide; Compound 267: (1aS,5aS)-2-(2,4-Difluoro-phenyl)-1a,2,5,5a-tetrahydro-1H-2,3-diaza-cyclopropa[a]pentalene-4-carboxylic acid ((3R,4R)-4-hydroxy-1,1-dioxo-tetrahydro-1$\lambda^6$-thiophen-3-yl)-amide; Compound 268: (1aR,5aR)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclopropyl]-amide; Compound 269: (1aR,5aR)-2-Pyridin-3-yl-1a,2,5,5a-tetrahydro-1H-2,3-diaza-cyclopropa[a]pentalene-4-carboxylic acid (2-hydroxy-1,1-dimethyl-ethyl)-amide; Compound 270: [(1aR,5aR)-2-(2,4-Difluoro-phenyl)-1a,2,5,5a-tetrahydro-1H-2,3-diaza-cyclopropa[a]pentalen-4-yl]-(1,3-dihydro-isoindol-2-yl)-methanone; Compound 271: (1aR,5aR)-2-(2,4-Difluoro-phenyl)-1a,2,5,5a-tetrahydro-1H-2,3-diaza-cyclopropa[a]pentalene-4-carboxylic acid (4-trifluoromethyl-pyridin-2-yl)-amide; Compound 272: (1aS,5aS)-2-(2,4-Difluoro-phenyl)-1a,2,5,5a-tetrahydro-1H-2,3-diaza-cyclopropa[a]pentalene-4-carboxylic acid ((1S,2S)-2-hydroxy-indan-1-yl)-amide; Compound 273: (1aS,5aS)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclopropyl]-amide; Compound 274: (1aR,5aR)-2-(5-Ethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 275: [(1aR,5aR)-2-(2,4-Difluoro-phenyl)-1a,2,5,5a-tetrahydro-1H-2,3-diaza-cyclopropa[a]pentalen-4-yl]-(3-trifluoromethyl-5,6-dihydro-8H-[1,2,4]triazolo[4,3-a]pyrazin-7-yl)-methanone; Compound 276: (1aR,5aR)-2-(2,4-Difluoro-phenyl)-1a,2,5,5a-tetrahydro-1H-2,3-diaza-cyclopropa[a]pentalene-4-carboxylic acid (5-methyl-thiazol-2-yl)-amide; Compound 277: [(1aR,5aR)-2-(2,4-Difluoro-phenyl)-1a,2,5,5a-tetrahydro-1H-2,3-diaza-cyclopropa[a]pentalen-4-yl]-(4-morpholin-4-yl-piperidin-1-yl)-methanone; Compound 278: 1-{[[(1aR,5aR)-2-(2,4-Difluoro-phenyl)-1a,2,5,5a-tetrahydro-1H-2,3-diaza-cyclopropa[a]pentalene-4-carbonyl]-amino}-cyclopropanecarboxylic acid methyl ester; Compound 279: (1aS,5aS)-2-(6'-Methyl-[3,3']bipyridinyl-6-yl)-1a,2,5,5a-tetrahydro-1H-2,3-diaza-cyclopropa[a]pentalene-4-carboxylic acid (2-hydroxy-1,1-dimethyl-ethyl)-amide; Compound 280: (1aR,5aR)-2-(2,4-Difluoro-phenyl)-1a,2,5,5a-tetrahydro-1H-2,3-diaza-cyclopropa[a]pentalene-4-carboxylic acid (3R)-(1-aza-bicyclo[2.2.2]oct-3-yl)-amide; Compound 281: (1aR,5aR)-2-(2,4-Difluoro-phenyl)-1a,2,5,5a-tetrahydro-1H-2,3-diaza-cyclopropa[a]pentalene-4-carboxylic acid (6-trifluoromethyl-pyridin-3-yl)-amide; Compound 282: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (1-phenyl-cyclopropyl)-amide; Compound 283: (1aR,5aR)-2-(5-Methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 284: (1aR,5aR)-2-(2,4-Difluoro-phenyl)-1a,2,5,5a-tetrahydro-1H-2,3-diaza-cyclopropa[a]pentalene-4-carboxylic acid (5-hydroxy-1H-pyrazol-3-yl)-amide; Compound 285: (1aR,5aR)-2-(2,4-Difluoro-phenyl)-1a,2,5,5a- tetrahydro-1H-2,3-diaza-cyclopropa[a]pentalene-4-carboxylic acid (2-thiomorpholin-4-yl-ethyl)-amide; Compound 286: (1aR,5aR)-2-(2,4-Dichloro-phenyl)-1a,2,5,5a-tetrahydro-1H-2,3-diaza-cyclopropa[a]pentalene-4-carboxylic acid (1-phenyl-cyclopropyl)-amide; Compound 287: (1aR,5aR)-2-(5-Bromo-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 288: (1aR,5aR)-2-(2,4-Difluoro-phenyl)-1a,2,5,5a-tetrahydro-1H-2,3-diaza-cyclopropa[a]pentalene-4-carboxylic acid (benzo[1,3]dioxol-5-ylmethyl)-amide; Compound 289: (1aR,5aR)-2-(2,4-Difluoro-phenyl)-1a,2,5,5a-tetrahydro-1H-2,3-diaza-cyclopropa[a]pentalene-4-carboxylic acid ((1S,2S)-2-amino-cyclohexyl)-amide; Compound 290: (1aS,5aS)-2-(2,4-Difluoro-phenyl)-1a,2,5,5a-tetrahydro-1H-2,3-diaza-cyclopropa[a]pentalene-4-carboxylic acid (3-dimethylamino-1-oxo-tetrahydro-1$\lambda^4$-thiophen-3-ylmethyl)-amide; Compound 291: (1aR,5aR)-2-(2,4-Difluoro-phenyl)-1a,2,5,5a-tetrahydro-1H-2,3-diaza-cyclopropa[a]pentalene-4-carboxylic acid (4-methyl-morpholin-2-ylmethyl)-amide; Compound 292: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-2-yl)-amide; Compound 293: (1aR,5aR)-2-(2,4-Difluoro-phenyl)-1a,2,5,5a-tetrahydro-1H-2,3-diaza-cyclopropa[a]pentalene-4-carboxylic acid ((1R,2S)-2-hydroxy-cyclohexylmethyl)-amide; Compound 294: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-phenyl)-cyclopropyl]-amide; Compound 295: (1aS,5aS)-2-(2,4-Difluoro-phenyl)-1a,2,5,5a-tetrahydro-1H-2,3-diaza-cyclopropa[a]pentalene-4-carboxylic acid ((R)-1-ethyl-pyrrolidin-2-ylmethyl)-amide; Compound 296: (R)-2-[((1aR,5aR)-2-tert-Butyl-1a,2,5,5a-tetrahydro-1H-2,3-diaza-cyclopropa[a]pentalene-carbonyl)-amino]-3-(4-fluoro-phenyl)-2-methyl-propionic acid; Compound 297: (1aR,5aR)-2-(2,4-Difluoro-phenyl)-1a,2,5,5a-tetrahydro-1H-2,3-diaza-cyclopropa[a]pentalene-4-carboxylic acid pyrazin-2-ylamide; Compound 298: (1aS,5aS)-2-(2,4-Difluoro-phenyl)-1a,2,5,5a-tetrahydro-1H-2,3-diaza-cyclopropa[a]pentalene-4-carboxylic acid (pyridin-2-ylmethyl)-amide; Compound 299: (1aR,5aR)-2-(5-Methyl-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 300: (1aR,5aR)-2-(5-Bromo-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 301: (1aR,5aR)-2-(3,5-Difluoro-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 302: (1aR,5aR)-2-(2,4-Difluoro-phenyl)-1a,2,5,5a-tetrahydro-1H-2,3-diaza-cyclopropa[a]pentalene-4-carboxylic acid pyridazin-3-ylamide; Compound 303: (1aR,5aR)-2-(2,4-Difluoro-phenyl)-1a,2,5,5a-tetrahydro-1H-2,3-diaza-cyclopropa[a]pentalene-4-carboxylic acid (4-pyridin-2-yl-thiazol-2-yl)-amide; Compound 304: (1aS,5aS)-2-(2,4-Difluoro-phenyl)-1a,2,5,5a-tetrahydro-1H-2,3-diaza-cyclopropa[a]pentalene-4-carboxylic acid [1-(2-methoxy-phenyl)-cyclopropyl]-amide; Compound 305: (1aR,5aR)-2-(6-Chloro-pyridazin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 306: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-piperidin-4-ylmethyl]-amide; Compound 307: (1aR,5aR)-2-(2,4-Difluoro-phenyl)-1a,2,5,5a-tetrahydro-1H-2,3-diaza-cyclopropa[a]pentalene-4-carboxylic acid (6-chloro-2-methyl-pyridin-3-yl)-amide; Compound 308: (1aR,5aR)-2-(2,4-Difluoro-phenyl)-1a,2,5,5a-tetrahydro-1H-2,3-diaza-cyclopropa[a]pentalene-4-carboxylic acid (6-hydroxy-pyridin-3-yl)-amide; Compound 309: (1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 310: (1aR,5aR)-2-(2,4-Difluoro-phenyl)-1a,2,5,5a-tetrahydro-1H-2,3-diaza-cyclopropa[a]pentalene-4-carboxylic acid 3-trifluoromethoxy-benzylamide; Compound 311: (1aR,5aR)-2-(2,4-Difluoro-phenyl)-1a,2,5,5a-tetrahydro-1H-2,3-diaza-cyclopropa[a]pentalene-4-carboxylic acid (1-morpholin-4-yl-cyclopentylmethyl)-amide; Compound 312: (1aS,5aS)-2-(2,4-Difluoro-phenyl)-1a,2,5,5a-tetrahydro-1H-2,3-diaza-cyclopropa[a]pentalene-4-carboxylic acid (4-benzyl-morpholin-2-ylmethyl)-amide; Compound 313: (1aR,5aR)-2-(2,4-Difluoro-phenyl)-1a,2,5,5a-tetrahydro-1H-2,3-diaza-cyclopropa[a]pentalene-4-carboxylic acid (1-pyridin-2-yl-cyclobutylmethyl)-amide; Compound 314: (1aR,5aR)-2-(5-Ethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 315: (1aR,5aR)-2-(2,4-Difluoro-phenyl)-1a,2,5,5a-tetrahydro-1H-2,3-diaza-cyclopropa[a]pentalene-4-carboxylic acid (R)-indan-1-ylamide; Compound 316: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 317: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 318: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (1-phenyl-cyclopropyl)-amide; Compound 319: (1aR,5aR)-2-(6-Methoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 320: [(1aR,5aR)-2-(2,4-Difluoro-phenyl)-1a,2,5,5a-tetrahydro-1H-2,3-diaza-cyclopropa[a]pentalen-4-yl]-(3,4-dihydro-1H-isoquinolin-2-yl)-methanone; Compound 321: (1aS,5aS)-2-(2,4-Difluoro-phenyl)-1a,2,5,5a-tetrahydro-1H-2,3-diaza-cyclopropa[a]pentalene-4-carboxylic acid (5-hydroxymethyl-pyridin-2-yl)-amide; Compound 322: (1aS,5aS)-2-(2,4-Difluoro-phenyl)-1a,2,5,5a-tetrahydro-1H-2,3-diaza-cyclopropa[a]pentalene-4-carboxylic acid (5-fluoro-1-oxy-pyridin-2-yl)-amide; Compound 323: (1aR,5aR)-2-(5-Trifluoromethyl-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 324: (1aR,5aR)-2-(5-Dimethylamino-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 325: (1aR,5aR)-2-tert-Butyl-1a,2,5,5a-tetrahydro-1H-2,3-diaza-cyclopropa[a]pentalene-4-carboxylic acid (1-methyl-1-phenyl-ethyl)-amide; Compound 326: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyridin-2-yl)-amide; Compound 327: [(1aR,5aR)-2-(2,4-Difluoro-phenyl)-1a,2,5,5a-tetrahydro-1H-2,3-diaza-cyclopropa[a]pentalen-4-yl]-[4-(3-methoxy-pyridin-2-yl)-piperazin-1-yl]-methanone; Compound 328: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-3-yl-ethyl)-amide; Compound 329: (1aR,5aR)-2-(5-Cyano-pyridin-2-yl)-1a,2,5,5a-tetrahydro-1H-2,3-diaza-cyclopropa[a]pentalene-4-carboxylic acid (1-phenylcyclopropyl)-amide; Compound 330: [(1aR,5aR)-2-(2,4-Difluoro-phenyl)-1a,2,5,5a-tetrahydro-1H-2,3-diaza-cyclopropa[a]pentalen-4-yl]-(3-hydroxy-piperidin-1-yl)-methanone; Compound 331: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-3-yl)-amide; Compound 332: (1aR,5aR)-2-(5-Chloro-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 333: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-hydroxy-1-hydroxymethyl-propyl)-amide; Compound 334: (1aR,5aR)-2-(2,4-Difluoro-phenyl)-1a,2,5,5a-tetrahydro-1H-2,3-diaza-cyclopropa[a]pentalene-4-carboxylic acid pyridin-2-ylamide; Compound 335: (1aR,5aR)-2-(2,4-Difluoro-phenyl)-1a,2,5,5a-tetrahydro-1H-2,3-diaza-cyclopropa[a]pentalene-4-carboxylic acid (2-chloro-pyridin-3-yl)-amide; Compound 336: (1aR,5aR)-2-(2-Hydroxy-2-methyl-propyl)-1a,2,5,5a-tetrahydro-1H-2,3-diaza-cyclopropa[a]pentalene-4-carboxylic acid (tetrahydro-pyran-4-ylmethyl)-amide; Compound 337: (1aR,5aR)-2-(5-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 338: (1aR,5aR)-2-(2,4-Difluoro-phenyl)-1a,2,5,5a-tetrahydro-1H-2,3-diaza-cyclopropa[a]pentalene-4-carboxylic acid (3-methyl-3H-imidazol-4-ylmethyl)-amide; Compound 339: (1aS,5aS)-2-(2,4-Difluoro-phenyl)-1a,2,5,5a-tetrahydro-1H-2,3-diaza-cyclopropa[a]pentalene-4-carboxylic acid (6-fluoro-pyridin-2-yl)-amide; Compound 340: 1-(2,4-Difluoro-phenyl)-3b,4,4a,5-tetrahydro-1H-cyclopropa[3,4]cyclopenta[1,2-c]pyrazole-3-carboxylic acid (1-methyl-1-pyridin-4-yl-ethyl)-amide; Compound 341: (1aR,5aR)-2-(6-Bromo-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 342: (1aR,5aR)-2-[1-(4-Fluoro-phenyl)-1-methyl-ethyl]-1a,2,5,5a-tetrahydro-1H-2,3-diaza-cyclopropa[a]pentalene-4-carboxylic acid (1-methyl-1-pyridin-4-yl-ethyl)-amide; Compound 343: (1aR,5aR)-2-(2,4-Difluoro-phenyl)-1a,2,5,5a-tetrahydro-1H-2,3-diaza-cyclopropa[a]pentalene-4-carboxylic acid 3-dimethylamino-benzylamide; Compound 344: (1aR,5aR)-2-(2,4-Difluoro-phenyl)-1a,2,5,5a-tetrahydro-1H-2,3-diaza-cyclopropa[a]pentalene-4-carboxylic acid (6-morpholin-4-yl-pyridin-3-yl)-amide; Compound 345: (1aR,5aR)-2-(2,4-Difluoro-phenyl)-1a,2,5,5a-tetrahydro-1H-2,3-diaza-cyclopropa[a]pentalene-4-carboxylic acid (1-o-tolyl-cyclopropyl)-amide; Compound 346: (1aS,5aS)-2-Phenyl-1a,2,5,5a-tetrahydro-1H-2,3-diaza-cyclopropa[a]pentalene-4-carboxylic acid (2-hydroxy-1,1-dimethyl-ethyl)-amide; Compound 347: ((1aR,5aR)-2-tert-Butyl-1a,2,5,5a-tetrahydro-1H-2,3-diaza-cyclopropa[a]pentalen-4-yl)-[4-(3-chloro-phenyl)-piperazin-1-yl]-methanone; Compound 348: (1aR,5aR)-2-(2,4-Difluoro-phenyl)-1a,2,5,5a-tetrahydro-1H-2,3-diaza-cyclopropa[a]pentalene-4-carboxylic acid [(R)-1-(3,3,3-trifluoro-propyl)-piperidin-3-yl]-amide; Compound 349: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-4-methyl-pyridin-3-yl)-amide; Compound 350: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-4-yl-ethyl)-amide; Compound 351: (1aS,5aS)-2-(5-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 352: (1aR,5aR)-2-Pyridin-2-yl-1a,2,5,5a-tetrahydro-1H-2,3-diaza-cyclopropa[a]pentalene-4-carboxylic acid (1-methyl-1-phenyl-ethyl)-amide; Compound 353: (1aR,5aR)-2-(2,4-Difluoro-phenyl)-1a,2,5,5a-tetrahydro-1H-2,3-diaza-cyclopropa[a]pentalene-4-carboxylic acid (5-methyl-pyridin-2-yl)-amide; Compound 354: (1aR,5aR)-2-(2,4-Difluoro-phenyl)-1a,2,5,5a-tetrahydro-1H-2,3-diaza-cyclopropa[a]pentalene-4-carboxylic acid (2-methyl-quinolin-4-yl)-amide; Compound 355: (1aS,5aS)-2-(2,4-Difluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 356: (1aS,5aS)-2-(5-Pyrimidin-5-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 357: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-pyrrolidin-3-ylmethyl]-amide; Compound 358: (1aR,5aR)-2-(2,4-Difluoro-phenyl)-1a,2,5,5a-tetrahydro-1H-2,3-diaza-cyclopropa[a]pentalene-4-carboxylic acid benzooxazol-2-ylamide; Compound 359: (1aR,5aR)-2-(2,4-Difluoro-phenyl)-1a,2,5,5a-tetrahydro-1H-2,3-diaza-cyclopropa[a]pentalene-4-carboxylic acid (1-pyridin-4-yl-cyclopropyl)-amide; Compound 360: (1aS,5aS)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 361: (1aR,5aR)-2-(2,4-Difluoro-phenyl)-1a,2,5,5a-tetrahydro-1H-2,3-diaza-cyclopropa[a]pentalene-4-carboxylic acid (1-methyl-piperidin-4-ylmethyl)-amide; Compound 362: (1aR,5aR)-2-(2,4-Difluoro-phenyl)-1a,2,5,5a-tetrahydro-1H-2,3-diaza-cyclopropa[a]pentalene-4-carboxylic acid (tetrahydro-pyran-4-ylmethyl)-amide; Compound 363: (1aR,5aR)-2-Pyridin-4-yl-1a,2,5,5a-tetrahydro-1H-2,3-diaza-cyclopropa[a]pentalene-4-carboxylic acid (5-fluoro-pyridin-2-yl)-amide; Compound 364: (1aS,5aS)-2-(2,4-Difluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 365: (1aR,5aR)-2-(4-Methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 366: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-2-yl-ethyl)-amide; Compound 367: (1aR,5aR)-2-(2,4-Difluoro-phenyl)-1a,2,5,5a-tetrahydro-1H-2,3-diaza-cyclopropa[a]pentalene-4-carboxylic acid [2-(2,6-dimethyl-morpholin-4-yl)-2-methyl-propyl]-amide; Compound 368: (3bS,4aR,5R)-1-(2,4-Difluoro-phenyl)-3b-isopropyl-5-methyl-3b,4,4a,5-tetrahydro-1H-cyclopropa[3,4]cyclopenta[1,2-c]pyrazole-3-carboxylic acid ((1S,2S)-2-hydroxy-indan-1-yl)-amide; Compound 369: (1aR,5aR)-2-(2,4-Difluoro-phenyl)-1a,2,5,5a-tetrahydro-1H-2,3-diaza-cyclopropa[a]pentalene-4-carboxylic acid (1-methyl-piperidin-2-ylmethyl)-amide; Compound 370: (1aR,5aR)-2-(2,4-Difluoro-phenyl)-1a,2,5,5a-tetrahydro-1H-2,3-diaza-cyclopropa[a]pentalene-4-carboxylic acid (pyridin-4-ylmethyl)-amide; Compound 371: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-pyridin-2-yl)-amide; Compound 372: (1aR,5aR)-2-(2,4-Difluoro-phenyl)-1a,2,5,5a-tetrahydro-1H-2,3-diaza-cyclopropa[a]pentalene-4-carboxylic acid (5,7-dimethyl-pyrazolo[1,5-a]pyrimidin-2-yl)-amide; Compound 373: (1aR,5aR)-2-(4-Cyano-phenyl)-1a,2,5,5a-tetrahydro-1H-2,3-diaza-cyclopropa[a]pentalene-4-carboxylic acid tert-butylamide; Compound 374: (1aR,5aR)-2-(5-Methoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 375: (1aR,5aR)-2-tert- Butyl-1a,2,5,5a-tetrahydro-1H-2,3-diaza-cyclopropa[a]pentalene-4-carboxylic acid ((1S,2S,5S)-6,6-dimethyl-bicyclo[3.1.1]hept-2-ylmethyl)-amide; Compound 376: (1aR,5aR)-2-(2,4-Difluoro-phenyl)-1a,2,5,5a-tetrahydro-1H-2,3-diaza-cyclopropa[a]pentalene-4-carboxylic acid [(S)-1-(2-methoxy-ethyl)-pyrrolidin-3-yl]-amide; Compound 377: (1aR,5aR)-2-(2,4-Difluoro-phenyl)-1a,2,5,5a-tetrahydro-1H-2,3-diaza-cyclopropa[a]pentalene-4-carboxylic acid [1-(5-methyl-pyridin-2-yl)-ethyl]-amide; Compound 378: (1aR,5aR)-2-(2,4-Difluoro-phenyl)-1a,2,5,5a-tetrahydro-1H-2,3-diaza-cyclopropa[a]pentalene-4-carboxylic acid [2-hydroxy-1-(tetrahydro-furan-3-yl)-ethyl]-amide; Compound 379: (1aS,5aS)-2-(5-Chloro-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 380: [(1aR,5aR)-2-(2,4-Difluoro-phenyl)-1a,2,5,5a-tetrahydro-1H-2,3-diaza-cyclopropa[a]pentalen-4-yl]-(6-methoxy-3,4-dihydro-1H-isoquinolin-2-yl)-methanone; Compound 381: [(1aR,5aR)-2-(2,4-Difluoro-phenyl)-1a,2,5,5a-tetrahydro-1H-2,3-diaza-cyclopropa[a]pentalen-4-yl]-morpholin-4-yl-methanone; Compound 382: (1aR,5aR)-2-(5-Chloro-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 383: (1aR,5aR)-2-(4-Fluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 384: (S)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester; Compound 385: (1aR,5aR)-2-(2,4-Difluoro-phenyl)-1a,2,5,5a-tetrahydro-1H-2,3-diaza-cyclopropa[a]pentalene-4-carboxylic acid (2-fluoro-pyridin-3-yl)-amide; Compound 386: (1aR,5aR)-2-(Tetrahydro-pyran-4-ylmethyl)-1a,2,5,5a-tetrahydro-1H-2,3-diaza-cyclopropa[a]pentalene-4-carboxylic acid (1-methyl-1-phenyl-ethyl)-amide; Compound 387: (1aR,5aR)-2-Pyrazin-2-yl-1a,2,5,5a-tetrahydro-1H-2,3-diaza-cyclopropa[a]pentalene-4-carboxylic acid (2-hydroxy-1,1-dimethyl-ethyl)-amide; Compound 388: (1aR,5aR)-2-(2,4-Difluoro-phenyl)-1a,2,5,5a-tetrahydro-1H-2,3-diaza-cyclopropa[a]pentalene-4-carboxylic acid morpholin-4-ylamide; Compound 389: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-4-yl-ethyl)-amide; Compound 390: 1-(2,4-Difluoro-phenyl)-3b,4,4a,5-tetrahydro-1H-cyclopropa[3,4]cyclopenta[1,2-c]pyrazole-3-carboxylic acid ((1S,2S)-2-hydroxy-indan-1-yl)-amide; Compound 391: (1aR,5aR)-2-(2-Fluoro-phenyl)-1a,2,5,5a-tetrahydro-1H-2,3-diaza-cyclopropa[a]pentalene-4-carboxylic acid (1-phenyl-cyclopropyl)-amide; Compound 392: (1aR,5aR)-2-(2,4-Difluoro-phenyl)-1a,2,5,5a-tetrahydro-1H-2,3-diaza-cyclopropa[a]pentalene-4-carboxylic acid pyridin-4-ylamide; Compound 393: (1aR,5aR)-2-(2,4-Difluoro-phenyl)-1a,2,5,5a-tetrahydro-1H-2,3-diaza-cyclopropa[a]pentalene-4-carboxylic acid (4-hydroxy-pyridin-2-yl)-amide; Compound 394: (S)-3-{[(1aS,5aS)-2-(2,4-Difluoro-phenyl)-1a,2,5,5a-tetrahydro-1H-2,3-diaza-cyclopropa[a]pentalene-4-carbonyl]-amino}-3-pyridin-3-yl-propionic acid; Compound 395: (1aR,5aR)-2-(5-Chloro-pyridin-2-yl)-1a,2,5,5a-tetrahydro-1H-2,3-diaza-cyclopropa[a]pentalene-4-carboxylic acid [1-(4-fluoro-phenyl)-cyclopropyl]-amide; Compound 396: (1aS,5aS)-2-(5-Propyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 397: (1aR,5aR)-2-(2,4-Difluoro-phenyl)-1a,2,5,5a-tetrahydro-1H-2,3-diaza-cyclopropa[a]pentalene-4-carboxylic acid 3-methoxy-benzylamide; Compound 398: (1aS,5aS)-2-(2,4-Difluoro-phenyl)-1a,2,5,5a-tetrahydro-1H-2,3-diaza-cyclopropa[a]pentalene-4-carboxylic acid (5-fluoro-pyridin-2-yl)-amide; Compound 399: (1aS,5aS)-2-(2,4-Difluoro-phenyl)-1a,2,5,5a-tetrahydro-1H-2,3-diaza-cyclopropa[a]pentalene-4-carboxylic acid (1-oxy-pyridin-2-yl)-amide; Compound 400: (1aR,5aR)-2-(1,1-Dioxo-tetrahydro-1?$^6$-thiophen-3-yl)-1a,2,5,5a-tetrahydro-1H-2,3-diaza-cyclopropa[a]pentalene-4-carboxylic acid (tetrahydro-pyran-4-ylmethyl)-amide; Compound 401: (1aR,5aR)-2-(6-Chloro-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 402: (1aR,5aR)-2-(2,4-Difluoro-phenyl)-1a,2,5,5a-tetrahydro-1H-2,3-diaza-cyclopropa[a]pentalene-4-carboxylic acid (1-ethyl-propyl)-amide; Compound 403: 6-{[(1aR,5aR)-2-(2,4-Difluoro-phenyl)-1a,2,5,5a-tetrahydro-1H-2,3-diaza-cyclopropa[a]pentalene-4-carbonyl]-amino}-pyridine-2-carboxylic acid; Compound 404: (1aS,5aS)-2-(2,4-Difluoro-phenyl)-1a,2,5,5a-tetrahydro-1H-2,3-diaza-cyclopropa[a]pentalene-4-carboxylic acid (3-cyano-5-methyl-pyridin-2-yl)-amide; Compound 405: [(1aR,5aR)-2-(2,4-Difluoro-phenyl)-1a,2,5,5a-tetrahydro-1H-2,3-diaza-cyclopropa[a]pentalen-4-yl]-((S)-2-hydroxymethyl-pyrrolidin-1-yl)-methanone; Compound 406: (1aS,5aS)-2-(5-m-Tolyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 407: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-methoxy-phenyl)-amide; Compound 408: (1aS,5aS)-2-(2,4-Difluoro-phenyl)-1a,2,5,5a-tetrahydro-1H-2,3-diaza-cyclopropa[a]pentalene-4-carboxylic acid (tetrahydro-pyran-4-ylmethyl)-amide; Compound 409: (1aR,5aR)-2-(4-Fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 410: (1aR,5aR)-2-(2,4-Difluoro-phenyl)-1a,2,5,5a-tetrahydro-1H-2,3-diaza-cyclopropa[a]pentalene-4-carboxylic acid (1,2,2,6,6-pentamethyl-piperidin-4-yl)-amide; Compound 411: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyridin-3-yl)-amide; Compound 412: (1aR,5aR)-2-Pyridin-4-yl-1a,2,5,5a-tetrahydro-1H-2,3-diaza-cyclopropa[a]pentalene-4-carboxylic acid cyclopentyl-amide; Compound 413: (1aR,5aR)-2-(2,4-Difluoro-phenyl)-1a,2,5,5a-tetrahydro-1H-2,3-diaza-cyclopropa[a]pentalene-4-carboxylic acid (morpholin-2-ylmethyl)-amide; Compound 414: (1aR,5aR)-2-(5-Hydroxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 415: 3-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-azetidine-1-carboxylic acid tert-butyl ester; Compound 416: (1aR,5aR)-2-(2,4-Difluoro-phenyl)-1a,2,5,5a-tetrahydro-1H-2,3-diaza-cyclopropa[a]pentalene-4-carboxylic acid (2-dimethylamino-2-pyridin-3-yl-ethyl)-amide; Compound 417: (1aR,5aR)-2-(4-Methoxy-phenyl)-1a,2,5,5a-tetrahydro-1H-2,3-diaza-cyclopropa[a]pentalene-4-carboxylic acid (tetrahydro-pyran-4-ylmethyl)-amide; Compound 418: (1aR,5aR)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclobutyl]-amide; Compound 419: (1aR,5aR)-2-(2,4-Difluoro-phenyl)-1a,2,5,5a-tetrahydro-1H-2,3-diaza-cyclopropa[a]pentalene-4-carboxylic acid 3-hydroxy-benzylamide; Compound 420: (1aS,5aS)-2-(2,4-Difluoro-phenyl)-1a,2,5,5a-tetrahydro-1H-2,3-diaza-cyclopropa[a]pentalene-4-carboxylic acid (6-methoxy-pyridin-2-yl)-amide; Compound 421: (1aR,5aR)-2-(2,4-Difluoro-phenyl)-1a,2,5,5a-tetrahydro-1H-2,3-diaza-cyclopropa[a]pentalene-4-carboxylic acid [(R)-1-(tetrahydro-furan-2-yl)methyl]-amide; Compound 422: 2-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-morpholine-4-carboxylic acid tert-butyl ester; Compound 423: (1aR,5aR)-2-(5-Cyclopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 424: (1aR,5aR)-2-tert-Butyl-1a,2,5,5a-tetrahydro-1H-2,3-diaza-cyclopropa[a]pentalene-4-carboxylic acid (1,1-dimethyl-2-morpholin-4-yl-ethyl)-amide; Compound 425: [(1aR,5aR)-2-(2,4-Difluoro-phenyl)-1a,2,5,5a-tetrahydro-1H-2,3-diaza-cyclopropa[a]pentalen-4-yl]-(1,3-dihydro-pyrrolo[3,4-c]pyridin-2-yl)-methanone; Compound 426: (R)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-3-phenyl-propionic acid methyl ester; Compound 427: (1aR,5aR)-2-(2,4-Difluoro-phenyl)-1a,2,5,5a-tetrahydro-1H-2,3-diaza-cyclopropa[a]pentalene-4-carboxylic acid [1-(3-fluoro-phenyl)-cyclopropyl]-amide; Compound 428: (1aR,5aR)-2-(2,6-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 429: (R)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-pyrrolidine-1-carboxylic acid tert-butyl ester; Compound 430: (1aR,5aR)-2-(2,4-Difluoro-phenyl)-1a,2,5,5a-tetrahydro-1H-2,3-diaza-cyclopropa[a]pentalene-4-carboxylic acid (2-o-tolyl-ethyl)-amide; Compound 431: (1aS,5aS)-2-(2,4-Difluoro-phenyl)-1a,2,5,5a-tetrahydro-1H-2,3-diaza-cyclopropa[a]pentalene-4-carboxylic acid (3-hydroxymethyl-1-isobutyl-pyrrolidin-3-yl)-amide; Compound 432: (1aR,5aR)-2-(3-Fluoro-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 433: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-azetidin-3-yl]-amide; Compound 434: (1aR,5aR)-2-(2,4-Difluoro-phenyl)-1a,2,5,5a-tetrahydro-1H-2,3-diaza-cyclopropa[a]pentalene-4-carboxylic acid (6-morpholin-4-yl-pyridin-2-ylmethyl)-amide; Compound 435: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-2-yl-ethyl)-amide; Compound 436: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-tetrahydro-1?$^6$-thiophen-3-ylmethyl)-amide; Compound 437: (1aR,5aR)-2-(2,4-Difluoro-phenyl)-1a,2,5,5a-tetrahydro-1H-2,3-diaza-cyclopropa[a]pentalene-4-carboxylic acid [2-(4-fluoro-phenoxy)-ethyl]-amide; Compound 438: (1aR,5aR)-2-(2,4-Difluoro-phenyl)-1a,2,5,5a-tetrahydro-1H-2,3-diaza-cyclopropa[a]pentalene-4-carboxylic acid (3-chloro-5-methyl-pyridin-2-yl)-amide; Compound 439: (1aS,5aS)-2-(2,4-Difluoro-phenyl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 440: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclopropyl)-amide; Compound 441: (1aR,5aR)-2-(5-Isopropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 442: (1aR,5aR)-2-(2,4-Difluoro-phenyl)-1a,2,5,5a-tetrahydro-1H-2,3-diaza-cyclopropa[a]pentalene-4-carboxylic acid (pyridin-2-ylmethyl)-amide; Compound 443: (1aR,5aR)-2-(2,4-Difluoro-phenyl)-1a,2,5,5a-tetrahydro-1H-2,3-diaza-cyclopropa[a]pentalene-4-carboxylic acid (2,6-dimethyl-pyrimidin-4-yl)-amide; Compound 444: (1aR,5aR)-2-(2,4-Difluoro-phenyl)-1a,2,5,5a-tetrahydro-1H-2,3-diaza-cyclopropa[a]pentalene-4-carboxylic acid [(S)-1-hydroxymethyl-2-(3H-imidazol-4-yl)-ethyl]-amide; Compound 445: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-3-yl-ethyl)-amide; Compound 446: (1aR,5aR)-2-(5-Bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 447: (1aR,5aR)-2-(2,4-Difluoro-phenyl)-1a,2,5,5a-tetrahydro-1H-2,3-diaza-cyclopropa[a]pentalene-4-carboxylic acid 4-methanesulfonyl-benzylamide; Compound 448: (1aR,5aR)-2-(2,4-Difluoro-phenyl)-1a,2,5,5a-tetrahydro-1H-2,3-diaza-cyclopropa[a]pentalene-4-carboxylic acid (6-fluoro-pyridin-2-yl)-amide; Compound 449: (1aS,5aS)-2-(2,4-Difluoro-phenyl)-1a,2,5,5a-tetrahydro-1H-2,3-diaza-cyclopropa[a]pentalene-4-carboxylic acid ((1R,2R)-2-hydroxy-indan-1-yl)-amide; Compound 450: (1aS,5aS)-2-(2,4-Difluoro-phenyl)-1a,2,5,5a-tetrahydro-1H-2,3-diaza-cyclopropa[a]pentalene-4-carboxylic acid (1-pyridin-3-yl-cyclopropyl)-amide; Compound 451: (1aR,5aR)-2-(5-Propyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 452: [(1aR,5aR)-2-(2,4-Difluoro-phenyl)-1a,2,5,5a-tetrahydro-1H-2,3-diaza-cyclopropa[a]pentalen-4-yl]-(3-pyridin-4-yl-pyrrolidin-1-yl)-methanone; Compound 453: (1aR,5aR)-2-(2,4-Difluoro-phenyl)-1a,2,5,5a-tetrahydro-1H-2,3-diaza-cyclopropa[a]pentalene-4-carboxylic acid (5-hydroxymethyl-pyridin-2-yl)-amide; Compound 454: [(1aR,5aR)-2-(2,4-Difluoro-phenyl)-1a,2,5,5a-tetrahydro-1H-2,3-diaza-cyclopropa[a]pentalen-4-yl]-[4-(pyridin-2-yloxy)-piperidin-1-yl]-methanone; Compound 455: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 456: (1aS,5aS)-2-[5-(2,4-Difluoro-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 457: (1aR,5aR)-2-(2,4-Difluoro-phenyl)-1a,2,5,5a-tetrahydro-1H-2,3-diaza-cyclopropa[a]pentalene-4-carboxylic acid (9-methyl-9-aza-bicyclo[3.3.1]non-1-yl)-amide; Compound 458: (1aR,5aR)-2-(2,4-Difluoro-phenyl)-1a,2,5,5a-tetrahydro-1H-2,3-diaza-cyclopropa[a]pentalene-4-carboxylic acid (2,6-dimethyl-pyridin-3-yl)-amide; Compound 459: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (tetrahydro-pyran-4-ylmethyl)-amide; Compound 460: (1aR,5aR)-2-(2-Fluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 461: (1aR,5aR)-2-(2,4-Difluoro-phenyl)-1a,2,5,5a-tetrahydro-1H-2,3-diaza-cyclopropa[a]pentalene-4-carboxylic acid 4-hydroxy-benzylamide; Compound 462: (1aR,5aR)-2-(2,4-Difluoro-phenyl)-1a,2,5,5a-tetrahydro-1H-2,3-diaza-cyclopropa[a]pentalene-4-carboxylic acid (2-oxo-2-phenyl-ethyl)-amide; Compound 463: (1aR,5aR)-2-(2,4-Difluoro-phenyl)-1a,2,5,5a-tetrahydro-1H-2,3-diaza-cyclopropa[a]pentalene-4-carboxylic acid tert-butylamide; Compound 464: (1aR,5aR)-2-(5-Bromo-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 465: (1aR,5aR)-2-(2,4-Difluoro-phenyl)-1a,2,5,5a-tetrahydro-1H-2,3-diaza-cyclopropa[a]pentalene-4- carboxylic acid (1-methyl-1H-pyrazol-3-ylmethyl)-amide; Compound 466: (1aR,5aR)-2-(2,4-Difluoro-phenyl)-1a,2,5,5a-tetrahydro-1H-2,3-diaza-cyclopropa[a]pentalene-4-carboxylic acid ((S)-1-pyridin-2-yl-ethyl)-amide; Compound 467: (1aR,5aR)-2-Pyridin-2-yl-1a,2,5,5a-tetrahydro-1H-2,3-diaza-cyclopropa[a]pentalene-4-carboxylic acid (1-phenyl-cyclopropyl)-amide; Compound 468: (1aR,5aR)-2-(6-Bromo-pyridin-3-yl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 469: [(1aR,5aR)-2-(2,4-Difluoro-phenyl)-1a,2,5,5a-tetrahydro-1H-2,3-diaza-cyclopropa[a]pentalen-4-yl]-(3-pyridin-2-yl-pyrrolidin-1-yl)-methanone; Compound 470: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-amino-cyclohexyl)-amide; Compound 471: (1aS,5aS)-2-(2,4-Difluoro-phenyl)-1a,2,5,5a-tetrahydro-1H-2,3-diaza-cyclopropa[a]pentalene-4-carboxylic acid ((R)-1-pyridin-2-yl-ethyl)-amide; Compound 472: (1aR,5aR)-2-Pyridin-2-yl-1a,2,5,5a-tetrahydro-1H-2,3-diaza-cyclopropa[a]pentalene-4-carboxylic acid (1-pyridin-2-yl-cyclopropyl)-amide; Compound 473: (1aS,5aS)-2-(5-Cyclopentyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 474: (1aR,5aR)-2-(2,4-Difluoro-phenyl)-1a,2,5,5a-tetrahydro-1H-2,3-diaza-cyclopropa[a]pentalene-4-carboxylic acid pyrimidin-2-ylamide; Compound 475: (1aR,5aR)-2-(2,4-Difluoro-phenyl)-1a,2,5,5a-tetrahydro-1H-2,3-diaza-cyclopropa[a]pentalene-4-carboxylic acid (5-methyl-pyrazin-2-yl)-amide; Compound 476: (1aR,5aR)-2-o-Tolyl-1a,2,5,5a-tetrahydro-1H-2,3-diaza-cyclopropa[a]pentalene-4-carboxylic acid (2-hydroxy-1,1-dimethyl-ethyl)-amide; Compound 477: (1aR,5aR)-2-(4-Fluoro-benzyl)-1a,2,5,5a-tetrahydro-1H-2,3-diaza-cyclopropa[a]pentalene-4-carboxylic acid (1-methyl-1-phenyl-ethyl)-amide; Compound 478: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-pyridin-3-yl)-1-methyl-ethyl]-amide; Compound 479: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-2-methyl-pyridin-3-yl)-amide; Compound 480: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-methyl-ethyl)-amide; Compound 481: (1aR,5aR)-2-(3-Methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 482: (1aR,5aR)-2-(2,4-Difluoro-phenyl)-1a,2,5,5a-tetrahydro-1H-2,3-diaza-cyclopropa[a]pentalene-4-carboxylic acid 2-hydroxy-benzylamide; Compound 483: (1aR,5aR)-2-(2,4-Difluoro-phenyl)-1a,2,5,5a-tetrahydro-1H-2,3-diaza-cyclopropa[a]pentalene-4-carboxylic acid (6-bromo-2-methyl-pyridin-3-yl)-amide; Compound 484: (1aR,5aR)-2-(2,4-Difluoro-phenyl)-1a,2,5,5a-tetrahydro-1H-2,3-diaza-cyclopropa[a]pentalene-4-carboxylic acid (2-methoxy-pyridin-3-yl)-amide; Compound 485: (1aR,5aR)-2-(2,4-Difluoro-phenyl)-1a,2,5,5a-tetrahydro-1H-2,3-diaza-cyclopropa[a]pentalene-4-carboxylic acid [1-(4-chloro-phenyl)-cyclobutyl]-amide; Compound 486: (1aR,5aR)-2-(2,4-Difluoro-phenyl)-1a,2,5,5a-tetrahydro-1H-2,3-diaza-cyclopropa[a]pentalene-4-carboxylic acid [2-(pyridine-2-sulfonyl)-ethyl]-amide; Compound 487: [(1aR,5aR)-2-(2,4-Difluoro-phenyl)-1a,2,5,5a-tetrahydro-1H-2,3-diaza-cyclopropa[a]pentalene-4-yl]-(7-methyl-3,4-dihydro-2H-[1,8]naphthyridin-1-yl)-methanone; Compound 488: (1aS,5aS)-2-(2,4-Difluoro-phenyl)-1a,2,5,5a-tetrahydro-1H-2,3-diaza-cyclopropa[a]pentalene-4-carboxylic acid (1-pyridin-2-yl-cyclopropyl)-amide; Compound 489: (1aR,5aR)-2-(2,4-Difluoro-phenyl)-1a,2,5,5a-tetrahydro-1H-2,3-diaza-cyclopropa[a]pentalene-4-carboxylic acid (1-pyridin-2-yl-cyclopropylmethyl)-amide; Compound 490: (1aR,5aR)-2-(6-Methyl-4-trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 491: (1aR,5aR)-2-(2,4-Difluoro-phenyl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 492: (1aR,5aR)-2-(2,4-Difluoro-phenyl)-1a,2,5,5a-tetrahydro-1H-2,3-diaza-cyclopropa[a]pentalene-4-carboxylic acid (1-methyl-1,2,3,4-tetrahydro-quinolin-7-yl)-amide; Compound 493: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 494: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclohexanecarboxylic acid methyl ester; Compound 495: (1aR,5aR)-2-(6-Dimethylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 496: (1aR,5aR)-2-(2,4-Difluoro-phenyl)-1a,2,5,5a-tetrahydro-1H-2,3-diaza-cyclopropa[a]pentalene-4-carboxylic acid benzylamide; Compound 497: (1aS,5aS)-2-(2,4-Difluoro-phenyl)-1a,2,5,5a-tetrahydro-1H-2,3-diaza-cyclopropa[a]pentalene-4-carboxylic acid (3,5-dimethyl-pyrazin-2-yl)-amide; Compound 498: (1aR,5aR)-2-(2,4-Difluoro-phenyl)-1a,2,5,5a-tetrahydro-1H-2,3-diaza-cyclopropa[a]pentalene-4-carboxylic acid (5-fluoro-1-oxy-pyridin-2-yl)-amide; Compound 499: (1aR,5aR)-2-(5-Trifluoromethyl-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 500: (1aR,5aR)-2-(1,1-Dioxo-hexahydro-1$?^6$-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 501: [(1aR,5aR)-2-(2,4-Difluoro-phenyl)-1a,2,5,5a-tetrahydro-1H-2,3-diaza-cyclopropa[a]pentalen-4-yl]-(3-pyridin-3-yl-pyrrolidin-1-yl)-methanone; Compound 502: (1aR,5aR)-2-(2,4-Difluoro-phenyl)-1a,2,5,5a-tetrahydro-1H-2,3-diaza-cyclopropa[a]pentalene-4-carboxylic acid [1-(2-hydroxy-pyridin-3-yl)-1-methyl-ethyl]-amide; Compound 503: (1aS,5aS)-2-(2,4-Difluoro-phenyl)-1a,2,5,5a-tetrahydro-1H-2,3-diaza-cyclopropa[a]pentalene-4-carboxylic acid (2-fluoro-pyridin-3-yl)-amide; Compound 504: 1-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclobutanecarboxylic acid ethyl ester; Compound 505: (1aS,5aS)-2-(5-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 506: [(1aR,5aR)-2-(2,4-Difluoro-phenyl)-1a,2,5,5a-tetrahydro-1H-2,3-diaza-cyclopropa[a]pentalen-4-yl]-((S)-3-hydroxy-pyrrolidin-1-yl)-methanone; Compound 507: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 508: (1aR,5aR)-2-(2-Difluoro-phenyl)-1a,2,5,5a-tetrahydro-1H-2,3-diaza-cyclopropa[a]pentalene-4-carboxylic acid ((1R,2S)-2-hydroxy-1-hydroxymethyl-propyl)-amide; Compound 509: 3-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-pyrrolidine-1-carboxylic acid tert-butyl ester; Compound 510: (1aS,5aS)-2-(2,4-Difluoro-phenyl)-1a,2,5,5a-tetrahydro-1H-2,3-diaza-cyclopropa[a]pentalene-4-carboxylic acid (tetrahydro-pyran-4-yl)-amide; Compound 511: (1aR,5aR)-2-(2-Hydroxy-2-methyl-propyl)-1a,2,5,5a-tetrahydro-1H-2,3-diaza-cyclopropa[a]pentalene-4-carboxylic acid (5-fluoro-pyridin-2-yl)-amide; Compound 512: (1aR,5aR)-2-(5-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 513: (1aR,5aR)-2-(2,4-Difluoro-phenyl)-1a,2,5,5a-tetrahydro-1H-2,3-diaza-cyclopropa[a]pentalene-4-carboxylic acid (quinolin-4-ylmethyl)-amide; Compound 514: (1aS,5aS)-2-(2,4-Difluoro-phenyl)-1a,2,5,5a-tetrahydro-1H-2,3-diaza-cyclopropa[a]pentalene-4-carboxylic acid pyrimidin-4-ylamide; Compound 515: 1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide; Compound 516: 1-{[(1aR,5aR)-2-(6-Bromo-pyridin-3-yl)-1a,2,5,5a-tetrahydro-1H-2,3-diaza-cyclopropa[a]pentalene-4-carbonyl]-amino}-cyclohexanecarboxylic acid methyl ester; Compound 517: (1aR,5aR)-2-tert-Butyl-1a,2,5,5a-tetrahydro-1H-2,3-diaza-cyclopropa[a]pentalene-4-carboxylic acid [(R)-2-(4-fluoro-phenyl)-1-(2-hydroxy-ethylcarbamoyl)-1-methyl-ethyl]-amide; Compound 518: (1aS,5aS)-2-(2,4-Difluoro-phenyl)-1a,2,5,5a-tetrahydro-1H-2,3-diaza-cyclopropa[a]pentalene-4-carboxylic acid pyridin-2-ylamide; Compound 519: (1aS,5aS)-2-(2,4-Difluoro-phenyl)-1a,2,5,5a-tetrahydro-1H-2,3-diaza-cyclopropa[a]pentalene-4-carboxylic acid ((S)-1-pyridin-2-yl-ethyl)-amide; Compound 520: (1aR,5aR)-2-(2,4-Difluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 521: (1aS,5aS)-2-[5-(4-Fluoro-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 522: (1aR,5aR)-2-tert-Butyl-1a,2,5,5a-tetrahydro-1H-2,3-diaza-cyclopropa[a]pentalene-4-carboxylic acid (R)-indan-1-ylamide; Compound 523: (1aR,5aR)-2-(2,4-Difluoro-phenyl)-1a,2,5,5a-tetrahydro-1H-2,3-diaza-cyclopropa[a]pentalene-4-carboxylic acid [(S)-1-(3,3,3-trifluoro-propyl)-piperidin-3-yl]-amide; Compound 524: (1aR,5aR)-2-(2,4-Difluoro-phenyl)-1a,2,5,5a-tetrahydro-1H-2,3-diaza-cyclopropa[a]pentalene-4-carboxylic acid (2-morpholin-4-yl-pyridin-3-yl)-amide; Compound 525: (1aR,5aR)-2-(5-Methyl-pyridin-2-yl)-1a,2,5,5a-tetrahydro-1H-2,3-diaza-cyclopropa[a]pentalene-4-carboxylic acid tert-butylamide; Compound 526: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 527: (1aR,5aR)-2-Pyridin-3-yl-1a,2,5,5a-tetrahydro-1H-2,3-diaza-cyclopropa[a]pentalene-4-carboxylic acid (1-methyl-1-phenyl-ethyl)-amide; Compound 528: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-2-yl)-amide; Compound 529: (1aR,5aR)-2-(2,4-Difluoro-phenyl)-1a,2,5,5a-tetrahydro-1H-2,3-diaza-cyclopropa[a]pentalene-4-carboxylic acid (tetrahydro-furan-2-ylmethyl)-amide; Compound 530: (1aS,5aS)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclopropyl]-amide; Compound 531: (1aS,5aS)-2-(5-Cyclopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 532: (1aR,5aR)-2-(2,4-Difluoro-phenyl)-1a,2,5,5a-tetrahydro-1H-2,3-diaza-cyclopropa[a]pentalene-4-carboxylic acid [(R)-1-(3,3,3-trifluoro-propyl)-pyrrolidin-3-yl]-amide; Compound 533: [(1aR,5aR)-2-(2,4-Difluoro-phenyl)-1a,2,5,5a-tetrahydro-1H-2,3-diaza-cyclopropa[a]pentalen-4-yl]-[4-(4,6-dimethyl-pyrimidin-2-yl)-piperazin-1-yl]-methanone; Compound 534: (1aR,5aR)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclopropyl]-amide; Compound 535: (1aS,5aS)-2-Pyridin-2-yl-1a,2,5,5a-tetrahydro-1H-2,3-diaza-cyclopropa[a]pentalene-4-carboxylic acid (2-hydroxy-1,1-dimethyl-ethyl)-amide; Compound 536: (1aR,5aR)-2-(2,4-Difluoro-phenyl)-1a,2,5,5a-tetrahydro-1H-2,3-diaza-cyclopropa[a]pentalene-4-carboxylic acid 3-difluoromethoxy-benzylamide; Compound 537: (1aS,5aS)-2-(2,4-Difluoro-phenyl)-1a,2,5,5a-tetrahydro-1H-2,3-diaza-cyclopropa[a]pentalene-4-carboxylic acid (4-hydroxy-1-methyl-piperidin-4-ylmethyl)-amide; Compound 538: (1aR,5aR)-2-(2,4-Difluoro-phenyl)-1a,2,5,5a-tetrahydro-1H-2,3-diaza-cyclopropa[a]pentalene-4-carboxylic acid [1-((R)-2-(S)-methyl-5-methyl-pyrrolidine-1-carbonyl)-cyclopentyl]-amide; Compound 539: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-3-yl-ethyl)-amide; Compound 540: (1aR,5aR)-2-(4-Methoxy-phenyl)-1a,2,5,5a-tetrahydro-1H-2,3-diaza-cyclopropa[a]pentalene-4-carboxylic acid (1-phenyl-cyclopropyl)-amide; Compound 541: (1aR,5aR)-2-(2,4-Difluoro-phenyl)-1a,2,5,5a-tetrahydro-1H-2,3-diaza-cyclopropa[a]pentalene-4-carboxylic acid 2-methoxy-benzylamide; Compound 542: 2-({[(1aS,5aS)-2-(2,4-Difluoro-phenyl)-1a,2,5,5a-tetrahydro-1H-2,3-diaza-cyclopropa[a]pentalene-4-carbonyl]-amino}-methyl)-morpholine-4-carboxylic acid tert-butyl ester; Compound 543: (1aR,5aR)-2-(6-Ethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 544: (1aR,5aR)-2-tert-Butyl-1a,2,5,5a-tetrahydro-1H-2,3-diaza-cyclopropa[a]pentalene-4-carboxylic acid (tetrahydro-pyran-4-ylmethyl)-amide; Compound 545: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-2-ylmethyl)-amide; Compound 546: (1aS,5aS)-2-(5-Chloro-pyridin-2-yl)-1a,2,5,5a-tetrahydro-1H-2,3-diaza-cyclopropa[a]pentalene-4-carboxylic acid (1-phenyl-cyclopropyl)-amide; Compound 547: (1aR,5aR)-2-(2,4-Difluoro-phenyl)-1a,2,5,5a-tetrahydro-1H-2,3-diaza-cyclopropa[a]pentalene-4-carboxylic acid (3-chloro-pyridin-4-yl)-amide; Compound 548: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-2-methyl-propionic acid; Compound 549: (1aR,5aR)-2-(2,4-Difluoro-phenyl)-1a,2,5,5a-tetrahydro-1H-2,3-diaza-cyclopropa[a]pentalene-4-carboxylic acid (6-chloro-pyridin-3-yl)-amide; Compound 550: (1aR,5aR)-2-(2,4-Difluoro-phenyl)-1a,2,5,5a-tetrahydro-1H-2,3-diaza-cyclopropa[a]pentalene-4-carboxylic acid (1-morpholin-4-ylmethyl-cyclopentyl)-amide; Compound 551: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-3-yl-ethyl)-amide; Compound 552: (1aR,5aR)-2-(4-Fluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 553: [(1aR,5aR)-2-(2,4-Difluoro-phenyl)-1a,2,5,5a-tetrahydro-1H-2,3-diaza-cyclopropa[a]pentalen-4-yl]-(2-methyl-3,4-dihydro-2H-quinolin-1-yl)-methanone; Compound 554: (1aR,5aR)-2-(2,4-Difluoro-phenyl)-1a,2,5,5a-tetrahydro-1H-2,3-diaza-cyclopropa[a]pentalene-4-carboxylic acid (1-p-tolyl-cyclopropyl)-amide; Compound 555: (1aR,5aR)-2-(2,4-Difluoro-phenyl)-1a,2,5,5a-tetrahydro-1H-2,3-diaza-cyclopropa[a]pentalene-4-carboxylic acid [(R)-1-(2-methoxy-ethyl)-piperidin-3-yl]-amide; Compound 556: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-4-yl-ethyl)-amide; Compound 557: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-piperidin-4-yl]-amide; Compound 558: [(1aR,5aR)-2-(2,4-Difluoro-phenyl)-1a,2,5,5a-tetrahydro-1H-2,3-diaza-cyclopropa[a]pentalen-4-yl]-((R)-2-hydroxymethyl-pyrrolidin-1-yl)-methanone; Compound 559: (1aR,5aR)-2-(2,4-Difluoro-phenyl)-1a,2,5,5a-tetrahydro-1H-2,3-diaza-cyclopropa[a]pentalene-4-carboxylic acid (4-methoxy-pyridin-2-yl)-amide; Compound 560: (1aR,5aR)-2-(5-Chloro-pyridin-2-yl)-1a,2,5,5a-tetrahydro-1H-2,3-diaza-cyclopropa[a]pentalene-4-carboxylic acid (1-phenyl-cyclopropyl)-amide; Compound 561: (1aR,5aR)-2-(2,4-Difluoro-phenyl)-1a,2,5,5a-tetrahydro-1H-2,3-diaza-cyclopropa[a]pentalene-4-carboxylic acid (3-azepan-1-yl-2,2-dimethyl-propyl)-amide; Compound 562: (1aR,5aR)-2-Pyridin-4-yl-1a,2,5,5a-tetrahydro-1H-2,3-diaza-cyclopropa[a]pentalene-4-carboxylic acid (tetrahydro-pyran-4-ylmethyl)-amide; Compound 563: (1aR,5aR)-2-(5-Methylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 564: 3-{[(1aR,5aR)-2-(2,4-Difluoro-phenyl)-1a,2,5,5a-tetrahydro-1H-2,3-diaza-cyclopropa[a]pentalene-4-carbonyl]-amino}-azetidine-1-carboxylic acid tert-butyl ester; Compound 565: (1aR,5aR)-2-(2,4-Dichloro-phenyl)-1a,2,5,5a-tetrahydro-1H-2,3-diaza-cyclopropa[a]pentalene-4-carboxylic acid (tetrahydro-pyran-4-ylmethyl)-amide; Compound 566: (1aR,5aR)-2-(2,4-Difluoro-phenyl)-1a,2,5,5a-tetrahydro-1H-2,3-diaza-cyclopropa[a]pentalene-4-carboxylic acid (5-methyl-pyrazin-2-ylmethyl)-amide; Compound 567: (1aR,5aR)-2-(2,4-Difluoro-phenyl)-1a,2,5,5a-tetrahydro-1H-2,3-diaza-cyclopropa[a]pentalene-4-carboxylic acid (1-oxo-hexahydro-1$\lambda^4$-thiopyran-4-yl)-amide; Compound 568: (1aR,5aR)-2-(5-Methyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 569: ((1aR,5aR)-2-tert-Butyl-1a,2,5,5a-tetrahydro-1H-2,3-diaza-cyclopropa[a]pentalen-4-yl)-(2-phenyl-morpholin-4-yl)-methanone; Compound 570: (S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-3-phenyl-propionic acid methyl ester; Compound 571: (1aS,5aS)-2-(5-Chloro-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 572: (1aR,5aR)-2-(2,4-Difluoro-phenyl)-1a,2,5,5a-tetrahydro-1H-2,3-diaza-cyclopropa[a]pentalene-4-carboxylic acid [2-(2-chloro-phenyl)-ethyl]-amide; Compound 573: (1aR,5aR)-2-(3-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 574: (1aR,5aR)-2-(2,4-Difluoro-phenyl)-1a,2,5,5a-tetrahydro-1H-2,3-diaza-cyclopropa[a]pentalene-4-carboxylic acid (3-chloro-5-trifluoromethyl-pyridin-2-ylmethyl)-amide; Compound 575: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1-hydroxymethyl-ethyl)-amide; Compound 576: (1aR,5aR)-2-(2,4-Difluoro-phenyl)-1a,2,5,5a-tetrahydro-1H-2,3-diaza-cyclopropa[a]pentalene-4-carboxylic acid [5-((S)-1-methyl-pyrrolidin-2-yl)-pyridin-2-yl]-amide; Compound 577: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclohexyl)-amide; Compound 578: (1aR,5aR)-2-(2,4-Difluoro-phenyl)-1a,2,5,5a-tetrahydro-1H-2,3-diaza-cyclopropa[a]pentalene-4-carboxylic acid (4,6-dimethyl-pyridin-2-yl)-amide; Compound 579: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-3-yl-ethyl)-amide; Compound 580: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-hydroxy-phenyl)-amide; Compound 581: (1aR,5aR)-2-(5-Cyclobutyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 582: (1aR,5aR)-2-(5-Ethoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 583: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 584: (1aR,5aR)-2-(5-Trifluoromethyl-pyrazin-2-yl)-1a,2,5,5a-tetrahydro-1H-2,3-diaza-cyclopropa[a]pentalene-4-carboxylic acid dimethylamide; Compound 585: (1aR,5aR)-2-(5-Cyano-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 586: (1aR,5aR)-2-(5-Cyclopropylmethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 587: (1aR,5aR)-2-(4-Trifluoromethyl-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 588: (1aR,5aR)-2-(5-Bromo-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 589: (1aR,5aR)-2-(4-Trifluoromethyl-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 590: (1aR,5aR)-2-(5-Cyclopropyl-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 591: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 592: (1aR,5aR)-2-(5-Cyano-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 593: (1aR,5aR)-2-Pyrazin-2-yl-1a,2,5,5a-tetrahydro-1H-2,3-diaza-cyclopropa[a]pentalene-4-carboxylic acid tert-butylamide; Compound 594: (1aR,5aR)-2-Pyrazin-2-yl-1a,2,5,5a-tetrahydro-1H-2,3-diaza-cyclopropa[a]pentalene-4-carboxylic acid (1-pyridin-4-yl-cyclobutyl)-amide; Compound 595: (1aR,5aR)-2-(5-Bromo-pyrazin-2-yl)-1a,2,5,5a-tetrahydro-1H-2,3-diaza-cyclopropa[a]pentalene-4-carboxylic acid (1-hydroxymethyl-cyclopropyl)-amide; Compound 596: (1aR,5aR)-2-(5-Pentafluoroethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 597: (1aR,5aR)-2-(5-Heptafluoropropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 598: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-1-methyl-piperidine-4-carboxylic acid methyl ester; Compound 599: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-1-methyl-piperidin-4-yl)-amide; Compound 600: (1aR,5aR)-2-(2,4-Difluoro-phenyl)-1a,2,5,5a-tetrahydro-1H-2,3-diaza-cyclopropa[a]pentalene-4-carboxylic acid [2-((R)-2-hydroxymethyl-pyrrolidin-1-yl)-ethyl]-amide; Compound 601: (1aR,5aR)-2-(2,4-Difluoro-phenyl)-1a,2,5,5a-tetrahydro-1H-2,3-diaza-cyclopropa[a]pentalene-4-carboxylic acid [2-((S)-2-hydroxymethyl-pyrrolidin-1-yl)-ethyl]-amide; Compound 602: (1aR,5aR)-2-(4-Trifluoromethyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 603: (1aS,5aS)-2-(4-Trifluoromethyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 604: (1aR,5aR)-2-Pyrazin-2-yl-1a,2,5,5a-tetrahydro-1H-2,3-diaza-cyclopropa[a]pentalene-4-carboxylic acid (1-phenyl-cyclohexyl)-amide; Compound 605: 1-[((1aR,5aR)-2-Pyrazin-2-yl-1a,2,5,5a-tetrahydro-1H-2,3-diaza-cyclopropa[a]pentalene-4-carbonyl)-amino]-cyclohexanecarboxylic acid methyl ester; Compound 606: (1aR,5aR)-2-(5-Chloro-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 607: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 608: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 609: (1aR,5aR)-2-Pyrazin-2-yl-1a,2,5,5a-tetrahydro-1H-2,3-diaza-cyclopropa[a]pentalene-4-carboxylic acid (1-hydroxymethyl-cyclohexyl)-amide; Compound 610: (1aS,5aS)-2-(5-Bromo-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 611: (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 612: (1aS,5aS)-2-(5-Bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 613: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 614: (1aR,5aR)-2-(5-Chloro-4-methyl-pyridin-2-yl)-1a,2,5,5a-tetrahydro-1H-2,3-diaza-cyclopropa[a]pentalene-4-carboxylic acid tert-butylamide; Compound 615: (1aS,5aS)-2-(2,4-Difluoro-phenyl)-1a,2,5,5a-tetrahydro-1H-2,3-diaza-cyclopropa[a]pentalene-4-carboxylic acid tert-butylamide; Compound 616: (1aR,5aR)-2-Pyrazin-2-yl-1a,2,5,5a-tetrahydro-1H-2,3-diaza-cyclopropa[a]pentalene-4-carboxylic acid (3-methyl-1,1-dioxo-tetrahydro-1$\lambda^6$-thiophen-3-yl)-amide; Compound 617: (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 618: (1aR,5aR)-2-Pyrazin-2-yl-1a,2,5,5a-tetrahydro-1H-2,3-diaza-cyclopropa[a]pentalene-4-carboxylic acid (1-cyano-cyclohexyl)-amide; Compound 619: (1aR,5aR)-2-Pyrazin-2-yl-1a,2,5,5a-tetrahydro-1H-2,3-diaza-cyclopropa[a]pentalene-4-carboxylic acid [1-(5-methyl-[1,2,4]oxadiazol-3-yl)-cyclohexyl]-amide; Compound 620: (1aS,5aS)-2-(4-Trifluoromethyl-pyridin-2-yl)-1a,2,5,5a-tetrahydro-1H-2,3-diaza-cyclopropa[a]pentalene-4-carboxylic acid tert-butylamide; Compound 621: (1aS,5aS)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 622: (1aR,5aR)-2-(4-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 623: (1aR,5aR)-2-(4-Trifluoromethyl-pyridin-2-yl)-1a,2,5,5a-tetrahydro-1H-2,3-diaza-cyclopropa[a]pentalene-4-carboxylic acid (cyano-dimethyl-methyl)-amide; Compound 624: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 625: (1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide; Compound 626: (1aR,5aR)-2-Pyrazin-2-yl-1a,2,5,5a-tetrahydro-1H-2,3-diaza-cyclopropa[a]pentalene-4-carboxylic acid N-methylcarbamoyl-N'-phenyl-hydrazide; Compound 627: (1aR,5aR)-2-Pyrazin-2-yl-1a,2,5,5a-tetrahydro-1H-2,3-diaza-cyclopropa[a]pentalene-4-carboxylic acid (cyano-dimethyl-methyl)-amide; Compound 628: (1aR,5aR)-2-Pyrazin-2-yl-1a,2,5,5a-tetrahydro-1H-2,3-diaza-cyclopropa[a]pentalene-4-carboxylic acid (1-carbamoyl-2,2-dimethyl-propyl)-amide; Compound 629: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 630: (1aR,5aR)-2-(4-Cyclopropyl-pyridin-2-yl)-1a,2,5,5a-tetrahydro-1H-2,3-diaza-cyclopropa[a]pentalene-4-carboxylic acid tert-butylamide; Compound 631: (1aR,5aR)-2-Pyrazin-2-yl-1a,2,5,5a-tetrahydro-1H-2,3-diaza-cyclopropa[a]pentalene-4-carboxylic acid N'-tert-butyl-hydrazide; Compound 632: (1aR,5aR)-2-(4-Trifluoromethyl-pyridin-2-yl)-1a,2,5,5a-tetrahydro-1H-2,3-diaza-cyclopropa[a]pentalene-4-carboxylic acid tert-butylamide; Compound 633: (1aR,5aR)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide; Compound 634: (1aR,5aR)-2-(2,4-Difluoro-phenyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 635: (1aR,5aR)-2-(4-Bromo-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 636: (1aR,5aR)-2-(4-Chloro-pyridin-2-yl)-1a,2,5,5a-tetrahydro-1H-2,3-diaza-cyclopropa[a]pentalene-4-carboxylic acid tert-butylamide; Compound 637: (1aR,5aR)-2-(4-Cyano-pyridin-2-yl)-1a,2,5,5a-tetrahydro-1H-2,3-diaza-cyclopropa[a]pentalene-4-carboxylic acid (cyano-dimethyl-methyl)-amide; Compound 638: (1aR,5aR)-2-Pyrazin-2-yl-1a,2,5,5a-tetrahydro-1H-2,3-diaza-cyclopropa[a]pentalene-4-carboxylic acid ((R)-1-cyclopropyl-ethyl)-amide; Compound 639: (1aR,5aR)-2-Pyrazin-2-yl-1a,2,5,5a-tetrahydro-1H-2,3-diaza-cyclopropa[a]pentalene-4-carboxylic acid N-cyclobutyl-hydrazide; Compound 640: (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic acid tert-butylamide; Compound 641: (1aR,5aR)-2-(2,4-Difluoro-phenyl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 642: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 643: (1aR,5aR)-2-Pyrazin-2-yl-1a,2,5,5a-tetrahydro-1H-2,3-diaza-cyclopropa[a]pentalene-4-carboxylic acid N-methylsulfonyl-N'-tert-butyl-hydrazide; Compound 644: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 645:

(1aR,5aR)-2-(4-Bromo-pyridin-2-yl)-1a,2,5,5a-tetrahydro-1H-2,3-diaza-cyclopropa[a]pentalene-4-carboxylic acid (1,1-dimethyl-prop-2-ynyl)-amide; Compound 646: Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester; Compound 647: (1aR,5aR)-2-Pyrazin-2-yl-1a,2,5,5a-tetrahydro-1H-2,3-diaza-cyclopropa[a]pentalene-4-carboxylic acid N-methylcarbamoyl-N'-tert-butyl-hydrazide; Compound 648: (1aR,5aR)-2-(4-Bromo-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 649: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 650: (1aR,5aR)-2-(2,4-Difluoro-phenyl)-1a,2,5,5a-tetrahydro-1H-2,3-diaza-cyclopropa[a]pentalene-4-carboxylic acid (1-carbamoyl-2,2-dimethyl-propyl)-amide; Compound 651: (1aR,5aR)-2-(4-Methanesulfonyl-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 652: (1aR,5aR)-2-(2,4-Difluoro-phenyl)-1a,2,5,5a-tetrahydro-1H-2,3-diaza-cyclopropa[a]pentalene-4-carboxylic acid (4-cyano-tetrahydro-pyran-4-yl)-amide; Compound 653: (1aR,5aR)-2-Pyrazin-2-yl-1a,2,5,5a-tetrahydro-1H-2,3-diaza-cyclopropa[a]pentalene-4-carboxylic acid N-cyclobutyl-N'-methylcarbamoyl-hydrazide; Compound 654: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (cyano-dimethyl-methyl)-amide; Compound 655: (1aR,5aR)-2-(4-Bromo-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 656: (1aR,5aR)-2-Pyrazin-2-yl-1a,2,5,5a-tetrahydro-1H-2,3-diaza-cyclopropa[a]pentalene-4-carboxylic acid (1-methyl-cyclobutyl)-amide; Compound 657: (1aR,5aR)-2-Pyrazin-2-yl-1a,2,5,5a-tetrahydro-1H-2,3-diaza-cyclopropa[a]pentalene-4-carboxylic acid (1-hydroxymethyl-cyclobutyl)-amide; Compound 658: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 659: (1aR,5aR)-2-Pyrazin-2-yl-1a,2,5,5a-tetrahydro-1H-2,3-diaza-cyclopropa[a]pentalene-4-carboxylic acid (1-pyridin-2-yl-cyclopropyl)-amide; Compound 660: (1aR,5aR)-2-(4-Oxy-pyrazin-2-yl)-1a,2,5,5a-tetrahydro-1H-2,3-diaza-cyclopropa[a]pentalene-4-carboxylic acid tert-butylamide; Compound 661: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-2-methyl-propyl)-amide; Compound 662: (1aR,5aR)-2-(4-Methoxy-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 663: (1aR,5aR)-2-(4-Cyano-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 664: (1aR,5aR)-2-Pyrazin-2-yl-1a,2,5,5a-tetrahydro-1H-2,3-diaza-cyclopropa[a]pentalene-4-carboxylic acid N-cyclobutyl-hydrazide; Compound 665: (1aR,5aR)-2-Pyrazin-2-yl-1a,2,5,5a-tetrahydro-1H-2,3-diaza-cyclopropa[a]pentalene-4-carboxylic acid (1-cyano-cyclopentyl)-amide; Compound 666: (1aR,5aR)-2-(2,4-Difluoro-phenyl)-1a,2,5,5a-tetrahydro-1H-2,3-diaza-cyclopropa[a]pentalene-4-carboxylic acid (cyano-dimethyl-methyl)-amide; Compound 667: (1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide; Compound 668: (1aR,5aR)-2-(4-Cyano-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 669: (1aR,5aR)-2-(4-Cyano-pyridin-2-yl)-1a,2,5,5a-tetrahydro-1H-2,3-diaza-cyclopropa[a]pentalene-4-carboxylic acid tert-butylamide; Compound 670: (1aR,5aR)-2-(4-Bromo-pyridin-2-yl)-1a,2,5,5a-tetrahydro-1H-2,3-diaza-cyclopropa[a]pentalene-4-carboxylic acid (1-methyl-cyclobutyl)-amide; Compound 671: (1aR,5aR)-2-Pyrazin-2-yl-1a,2,5,5a-tetrahydro-1H-2,3-diaza-cyclopropa[a]pentalene-4-carboxylic acid ((S)-1-cyclopropyl-ethyl)-amide; Compound 672: (1aR,5aR)-2-Pyrazin-2-yl-1a,2,5,5a-tetrahydro-1H-2,3-diaza-cyclopropa[a]pentalene-4-carboxylic acid N-phenyl-hydrazide; Compound 673: (1aR,5aR)-2-(4-Bromo-pyridin-2-yl)-1a,2,5,5a-tetrahydro-1H-2,3-diaza-cyclopropa[a]pentalene-4-carboxylic acid tert-butylamide; Compound 674: (1aR,5aR)-2-(4-Chloro-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 675: (1aR,5aR)-2-(4-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 676: 1-[((1aR,5aR)-2-Pyrazin-2-yl-1a,2,5,5a-tetrahydro-1H-2,3-diaza-cyclopropa[a]pentalene-4-carbonyl)-amino]-cyclobutanecarboxylic acid ethyl ester; Compound 677: (1aR,5aR)-2-(4-Bromo-pyridin-2-yl)-1a,2,5,5a-tetrahydro-1H-2,3-diaza-cyclopropa[a]pentalene-4-carboxylic acid (cyano-dimethyl-methyl)-amide; Compound 678: (1aR,5aR)-2-Pyrazin-2-yl-1a,2,5,5a-tetrahydro-1H-2,3-diaza-cyclopropa[a]pentalene-4-carboxylic acid ((S)-1-pyridin-2-yl-ethyl)-amide; Compound 679: (1aR,5aR)-2-Pyrazin-2-yl-1a,2,5,5a-tetrahydro-1H-2,3-diaza-cyclopropa[a]pentalene-4-carboxylic acid (1-methyl-1-pyridin-2-yl-ethyl)-amide; Compound 680: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-propyl)-amide; Compound 681: (1aR,5aR)-2-(4-Methoxy-pyridin-2-yl)-1a,2,5,5a-tetrahydro-1H-2,3-diaza-cyclopropa[a]pentalene-4-carboxylic acid tert-butylamide; Compound 682: (1aR,5aR)-2-(4-Chloro-pyridin-2-yl)-1a,2,5,5a-tetrahydro-1H-2,3-diaza-cyclopropa[a]pentalene-4-carboxylic acid [1-methyl-1-(1H-tetrazol-5-yl)-ethyl]-amide; Compound 683: Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester; Compound 684: (1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide; Compound 685: (1aR,5aR)-2-Pyrazin-2-yl-1a,2,5,5a-tetrahydro-1H-2,3-diaza-cyclopropa[a]pentalene-4-carboxylic acid ((R)-2-hydroxy-1-tetrahydro-pyran-4-yl-ethyl)-amide; Compound 686: (1aR,5aR)-2-Pyrazin-2-yl-1a,2,5,5a-tetrahydro-1H-2,3-diaza-cyclopropa[a]pentalene-4-carboxylic acid ((R)-1,2-dimethyl-propyl)-amide; Compound 687: (1aR,5aR)-2-(4-Oxy-pyrazin-2-yl)-1a,2,5,5a-tetrahydro-1H-2,3-diaza-cyclopropa[a]pentalene-4-carboxylic acid N-tert-butyl-hydrazide; Compound 688: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide; Compound 689: (1aR,5aR)-2-(4-Oxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 690: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)- amide; Compound 691: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-phenyl-ethyl)-amide; Compound 692: (4-Methyl-piperazin-1-yl)-((1aR,5aR)-2-pyrazin-2-yl-1a,2,5,5a-tetrahydro-1H-2,3-diaza-cyclopropa[a]pentalen-4-yl)-methanone; Compound 693: (1aR,2S,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 694: (1aR,2R,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 695: (1aS,5aS)-2-Pyrazin-2-yl-1a,2,5,5a-tetrahydro-1H-2,3-diaza-cyclopropa[a]pentalene-4-carboxylic acid (1-pyridin-2-yl-cyclobutyl)-amide; Compound 696: (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 697: (1aS,5aS)-2-Pyrazin-2-yl-1a,2,5,5a-tetrahydro-1H-2,3-diaza-cyclopropa[a]pentalene-4-carboxylic acid ((R)-1-hydroxymethyl-2,2-dimethyl-propyl)-amide; Compound 698: (1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide; Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 700: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide; Compound 701: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 702: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-4-yl-cyclobutyl)-amide; Compound 703: Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester; Compound 704: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 705: (1aR,5aR)-2-(4-Oxy-pyrazin-2-yl)-1a,2,5,5a-tetrahydro-1H-2,3-diaza-cyclopropa[a]pentalene-4-carboxylic acid (4-methylcarbamoyl-tetrahydro-pyran-4-yl)-amide; Compound 706: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-1-methylcarbamoyl-ethyl)-amide; Compound 707: (1aS,5aS)-2-Pyrazin-2-yl-1a,2,5,5a-tetrahydro-1H-2,3-diaza-cyclopropa[a]pentalene-4-carboxylic acid ((S)-2,2-dimethyl-1-morpholin-4-ylmethyl-propyl)-amide; Compound 708: (1aR,5aR)-2-(4-Oxy-pyrazin-2-yl)-1a,2,5,5a-tetrahydro-1H-2,3-diaza-cyclopropa[a]pentalene-4-carboxylic acid (1-methylcarbamoyl-cyclopent-3-enyl)-amide; Compound 709: {[(1aS,5aS)-2-(4-Oxy-pyrazin-2-yl)-1a,2,5,5a-tetrahydro-1H-2,3-diaza-cyclopropa[a]pentalene-4-carbonyl]-amino}-pyridin-2-yl-acetic acid methyl ester; Compound 710: (1aS,5aS)-2-(4-Oxy-pyrazin-2-yl)-1a,2,5,5a-tetrahydro-1H-2,3-diaza-cyclopropa[a]pentalene-4-carboxylic acid (methylcarbamoyl-pyridin-2-yl-methyl)-amide; Compound 711: {[(1aR,5aR)-2-(4-Oxy-pyrazin-2-yl)-1a,2,5,5a-tetrahydro-1H-2,3-diaza-cyclopropa[a]pentalene-4-carbonyl]-amino}-pyridin-2-yl-acetic acid methyl ester; Compound 712: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-morpholin-4-ylmethyl-propyl)-amide; Compound 713: (1aR,5aR)-2-(4-Oxy-pyrazin-2-yl)-1a,2,5,5a-tetrahydro-1H-2,3-diaza-cyclopropa[a]pentalene-4-carboxylic acid (methylcarbamoyl-pyridin-2-yl-methyl)-amide; Compound 714: (1aR,5aR)-2-(4-Oxy-pyrazin-2-yl)-1a,2,5,5a-tetrahydro-1H-2,3-diaza-cyclopropa[a]pentalene-4-carboxylic acid (1-methylcarbamoyl-cyclopentyl)-amide; Compound 715: (1aR,5aR)-2-(4-Oxy-pyrazin-2-yl)-1a,2,5,5a-tetrahydro-1H-2,3-diaza-cyclopropa[a]pentalene-4-carboxylic acid [1-((S)-tert-butylcarbamoyl)-2,2-dimethyl-propyl]-amide; Compound 716: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclopropyl)-amide; Compound 717: (1aS,5aS)-2-(4-Oxy-pyrazin-2-yl)-1a,2,5,5a-tetrahydro-1H-2,3-diaza-cyclopropa[a]pentalene-4-carboxylic acid (1-methyl-1-phenyl-ethyl)-amide; Compound 718: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-1-phenyl-ethyl)-amide; Compound 719: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2,2-dimethyl-1-(pyridin-2-ylcarbamoyl)-propyl]-amide; Compound 720: (1aR,5aR)-2-(4-Oxy-pyrazin-2-yl)-1a,2,5,5a-tetrahydro-1H-2,3-diaza-cyclopropa[a]pentalene-4-carboxylic acid [1-(pyridin-2-ylcarbamoyl)-cyclobutyl]-amide; Compound 721: (1aR,5aR)-2-(4-Oxy-pyrazin-2-yl)-1a,2,5,5a-tetrahydro-1H-2,3-diaza-cyclopropa[a]pentalene-4-carboxylic acid (1-methylcarbamoyl-cyclobutyl)-amide; Compound 722: (1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide; Compound 723: (1aR,5aR)-2-(4-Oxy-pyrazin-2-yl)-1a,2,5,5a-tetrahydro-1H-2,3-diaza-cyclopropa[a]pentalene-4-carboxylic acid pyrrolidin-1-ylamide; Compound 724: (1aR,5aR)-2-(4-Oxy-pyrazin-2-yl)-1a,2,5,5a-tetrahydro-1H-2,3-diaza-cyclopropa[a]pentalene-4-carboxylic acid piperidin-1-ylamide; Compound 725: (1aR,5aR)-2-(4-Oxy-pyrazin-2-yl)-1a,2,5,5a-tetrahydro-1H-2,3-diaza-cyclopropa[a]pentalene-4-carboxylic acid (2,6-dimethyl-piperidin-1-yl)-amide; Compound 726: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-cyclopropylcarbamoyl-2,2-dimethyl-propyl)-amide; Compound 727: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2,2-dimethyl-1-(2,2,2-trifluoro-ethylcarbamoyl)-propyl]-amide; Compound 728: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-ethylcarbamoyl-2,2-dimethyl-propyl)-amide; Compound 729: (1aR,5aR)-2-(4-Oxy-pyrazin-2-yl)-1a,2,5,5a-tetrahydro-1H-2,3-diaza-cyclopropa[a]pentalene-4-carboxylic acid N-tert-butyl-N-methyl-hydrazide; Compound 730: (1aS,5aS)-2-(4-Oxy-pyrazin-2-yl)-1a,2,5,5a-tetrahydro-1H-2,3-diaza-cyclopropa[a]pentalene-4-carboxylic acid tert-butyl-(2,2-dimethyl-1-pyridin-2-yl-propyl)-amide; Compound 731: (1aR,5aR)-2-(4-Oxy-pyrazin-2-yl)-1a,2,5,5a-tetrahydro-1H-2,3-diaza-cyclopropa[a]pentalene-4-carboxylic acid tert-butyl-(2,2-dimethyl-1-pyridin-2-yl-propyl)-amide; Compound 732: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2-methyl-propyl)-amide; Compound 733: (1aR,5aR)-2-(2,4-Difluoro-phenyl)-1a,2,5,5a-tetrahydro-1H-2,3-diaza-cyclopropa[a]pentalene-4-carboxylic acid ((1S,2R)-2-hydroxy-cyclopentyl)-amide; Compound 734: (1aR,5aR)-2-Pyrazin-2-yl-1a,2,5,5a-tetrahydro-1H-2,3-diaza-cyclopropa

[a]pentalene-4-carboxylic acid (1-pyridin-2-yl-cyclobutyl)-amide; Compound 735: (1aR,5aR)-2-(2,4-Difluoro-phenyl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide; Compound 736: (1aR,5aR)-2-Pyrazin-2-yl-1a,2,5,5a-tetrahydro-1H-2,3-diaza-cyclopropa[a]pentalene-4-carboxylic acid N-methylsulfonyl-N'-cyclobutyl-hydrazide; Compound 737: (1aR,5aR)-2-Pyrazin-2-yl-1a,2,5,5a-tetrahydro-1H-2,3-diaza-cyclopropa[a]pentalene-4-carboxylic acid N-methylsulfonyl-N'-phenyl-hydrazide; Compound 738: (1aR,5aR)-2-Pyrazin-2-yl-1a,2,5,5a-tetrahydro-1H-2,3-diaza-cyclopropa[a]pentalene-4-carboxylic acid cyclopentylamide; Compound 739: (1aR,5aR)-2-(2,4-Difluoro-phenyl)-1a,2,5,5a-tetrahydro-1H-2,3-diaza-cyclopropa[a]pentalene-4-carboxylic acid ((S)-1-cyclopropyl-2-hydroxy-ethyl)-amide; Compound 740: (1aR,5aR)-2-Pyrazin-2-yl-1a,2,5,5a-tetrahydro-1H-2,3-diaza-cyclopropa[a]pentalene-4-carboxylic acid ((R)-1,2,2-trimethyl-propyl)-amide; Compound 741: (1aR,5aR)-2-Pyrazin-2-yl-1a,2,5,5a-tetrahydro-1H-2,3-diaza-cyclopropa[a]pentalene-4-carboxylic acid ((1S,2R)-2-hydroxy-cyclopentyl)-amide; Compound 742: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-tetrahydro-pyran-4-yl-ethyl)-amide; Compound 743: (1aS,5aS)-2-(4-Oxy-pyrazin-2-yl)-1a,2,5,5a-tetrahydro-1H-2,3-diaza-cyclopropa[a]pentalene-4-carboxylic acid [pyridin-2-yl-(2,2,2-trifluoro-ethylcarbamoyl)-methyl]-amide; Compound 744: (1aS,5aS)-2-(4-Oxy-pyrazin-2-yl)-1a,2,5,5a-tetrahydro-1H-2,3-diaza-cyclopropa[a]pentalene-4-carboxylic acid (2,2-dimethyl-1-pyridin-2-yl-propyl)-amide; Compound 745: (1aR,5aR)-2-(4-Oxy-pyrazin-2-yl)-1a,2,5,5a-tetrahydro-1H-2,3-diaza-cyclopropa[a]pentalene-4-carboxylic acid (2,2-dimethyl-1-pyridin-2-yl-propyl)-amide; Compound 746: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester; Compound 747: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid; Compound 748: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(hydroxy-methyl-carbamoyl)-2,2-dimethyl-propyl]-amide; Compound 749: (1aR,5aR)-2-(Tetrahydro-pyran-4-ylmethyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 750: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-dimethylcarbamoyl-2,2-dimethyl-propyl)-amide; Compound 751: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(azetidine-1-carbonyl)-2,2-dimethyl-propyl]-amide; Compound 752: (1aR,5aR)-2-(Tetrahydro-pyran-4-ylmethyl)-1a,2,5,5a-tetrahydro-1H-2,3-diaza-cyclopropa[a]pentalene-4-carboxylic acid (1-pyridin-2-yl-cyclobutyl)-amide; Compound 753: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclopropyl)-amide; Compound 754: (1aS,5aS)-2-(4-Oxy-pyrazin-2-yl)-1a,2,5,5a-tetrahydro-1H-2,3-diaza-cyclopropa[a]pentalene-4-carboxylic acid [1-(4-fluoro-phenyl)-cyclobutyl]-amide; Compound 755: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-methoxycarbamoyl-2,2-dimethyl-propyl)-amide; Compound 756: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(methoxy-methyl-carbamoyl)-2,2-dimethyl-propyl]-amide; Compound 757: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 758: (1aR,5aR)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 759: (1aR,5aR)-2-(4-Cyano-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 760: (S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-3,3-dimethyl-butyric acid; Compound 761: (1aR,5aR)-2-(2,4-Difluoro-phenyl)-1a,2,5,5a-tetrahydro-1H-2,3-diaza-cyclopropa[a]pentalene-4-carboxylic acid ((S)-methylcarbamoyl-phenyl-methyl)-amide; Compound 762: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-tert-butoxycarbamoyl-2,2-dimethyl-propyl)-amide; Compound 763: (1aR,5aR)-2-Piperidin-4-yl-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 764: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide; Compound 765: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide; Compound 766: (1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 767: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 768: (1aR,5aR)-2-(Tetrahydro-pyran-4-yl)-1a,2,5,5a-tetrahydro-1H-2,3-diaza-cyclopropa[a]pentalene-4-carboxylic acid (1-pyridin-2-yl-cyclobutyl)-amide; Compound 769: (1aR,5aR)-2-(Tetrahydro-pyran-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 770: (1aR,5aR)-2-((R)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid (1-pyridin-2-yl-cyclobutyl)-amide; Compound 771: (1aR,5aR)-2-(2-Chloro-pyridin-4-yl)-1a,2,5,5a-tetrahydro-1H-2,3-diaza-cyclopropa[a]pentalene-4-carboxylic acid (1-pyridin-2-yl-cyclobutyl)-amide; Compound 772: (1aR,5aR)-2-(2-Chloro-pyridin-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 773: (1aR,5aR)-2-(5-Bromo-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 774: (1aR,5aR)-2-(5-Bromo-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 775: (1aR,5aR)-2-(5-Cyano-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 776: (1aR,5aR)-2-(5-Cyano-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 777: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1- hydroxycarbamoyl-2,2-dimethyl-propyl)-amide; Compound 778: (1aR,5aR)-2-((R)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 779: (1aR,5aR)-2-((S)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 780: (1aR,5aR)-2-(5-Fluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 781: (1aR,5aR)-2-(5-Fluoro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 782: (1aR,5aR)-2-(5-Fluoro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 783: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 784: (1aR,5aR)-2-(5-Chloro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 785: (1aR,5aR)-2-(5-Chloro-pyridin-2-yl)-1a,2,5,5a-tetrahydro-1H-2,3-diaza-cyclopropa[a]pentalene-4-carboxylic acid ((1S,2S)-1-hydroxymethyl-2-methyl-butyl)-amide; Compound 786: (1aR,5aR)-2-(5-Chloro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 787: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 788: (1aR,5aR)-2-(5-Chloro-3-fluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 789: (1aR,5aR)-2-(5-Bromo-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 790: (1aR,5aR)-2-(5-Bromo-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 791: (1aR,5aR)-2-(5-Cyano-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 792: (1aR,5aR)-2-(5-Cyano-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 793: (1aR,5aR)-2-(Tetrahydro-pyran-4-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 794: (1aR,5aR)-2-(5-Chloro-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 795: (1aR,5aR)-2-(5-Chloro-3-fluoro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 796: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 797: (1aR,5aR)-2-Pyrazin-2-yl-1a,2,5,5a-tetrahydro-1H-2,3-diaza-cyclopropa[a]pentalene-4-carboxylic acid (2,2-dimethyl-1-pyridin-2-yl-propyl)-amide; Compound 798: (1aS,5aS)-2-Pyrazin-2-yl-1a,2,5,5a-tetrahydro-1H-2,3-diaza-cyclopropa[a]pentalene-4-carboxylic acid (2,2-dimethyl-1-pyridin-2-yl-propyl)-amide; Compound 799: (1aR,5aR)-2-(3-Fluoro-pyridin-4-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 800: (1aR,5aR)-2-(3-Fluoro-pyridin-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 801: (1aR,5aR)-2-(5-Chloro-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 802: (1aR,5aR)-2-(5-Chloro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 803: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 804: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 805: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 806: (1aR,5aR)-2-(3,5-Difluoro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 807: (1aR,5aR)-2-(3-Fluoro-5-methoxy-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 808: (1aR,5aR)-2-(3,5-Difluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 809: (1aS,5aS)-2-Pyridin-2-yl-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 810: (1aR,5aR)-2-(2,4-Difluoro-phenyl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 811: (1aR,5aR)-2-(2,4-Difluoro-phenyl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 812: (1aR,5aR)-2-Pyridin-2-yl-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 813: (1aR,5aR)-2-Pyridin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 814: (1aR,5aR)-2-(2,4-Difluoro-phenyl)-1a,2,5,5a-tetrahydro-1H-2,3-diaza-cyclopropa[a]pentalene-4-carboxylic acid [1-(2-hydroxy-ethylcarbamoyl)-2,2-dimethyl-propyl]-amide; Compound 815: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(tetrahydro-furan-2-yl)methyl]-amide; Compound 816: (1aR,5aR)-2-(4-Oxy-pyrazin-2-yl)-1a,2,5,5a-tetrahydro-1H-2,3-diaza-cyclopropa[a]pentalene-4-carboxylic acid [1-(2-fluoro-phenyl)-cyclobutyl]-amide; Compound 817: (1aS,5aS)-2-(4-Oxy-pyrazin-2-yl)-1a,2,5,5a-tetrahydro-1H-2,3-diaza-cyclopropa[a]pentalene-4-carboxylic acid [1-(2-fluoro-phenyl)-cyclobutyl]-amide; Compound 818: (1aR,5aR)-2-Pyrazin-2-yl-1a,2,5,5a-tetrahydro-1H-2,3-diaza-cyclopropa[a]pentalene-4-carboxylic acid [(S)-1-(2-hydroxy-ethylcarbamoyl)-2,2-dimethyl-propyl]-amide; Compound 819: (1aR,5aR)-2-(2,4-Difluoro-phenyl)-1a,2,5,5a-tetrahydro-1H-2,3-diaza-cyclopropa[a]pentalene-4-carboxylic acid (1,1-bis-hydroxymethyl-propyl)-amide; Compound 820: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 821: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide; Compound 822: (1aR,5aR)-2-(2-Chloro-4-fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 823: (1aR,5aR)-2-(2-Chloro-4-fluoro-phenyl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 824: (1aR,5aR)-2-(2-Chloro-4-fluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 825: (1aR,5aR)-2-(2-Chloro-4-fluoro-phenyl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 826: (1aR,5aR)-2-(2-Chloro-4-fluoro-phenyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 827: (1aR,5aR)-2-(2-Chloro-4-fluoro-phenyl)-1a,2,5,5a-tetrahydro-1H-2,3-diaza-cyclopropa[a]pentalene-4-carboxylic acid (1-pyridin-2-yl-cyclobutyl)-amide; Compound 828: (1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide; Compound 829: (1aR,5aR)-2-(4-Oxy-pyrazin-2-yl)-1a,2,5,5a-tetrahydro-1H-2,3-diaza-cyclopropa[a]pentalene-4-carboxylic acid (1-phenyl-cyclopropyl)-amide; Compound 830: (1aR,5aR)-2-Pyrazin-2-yl-1a,2,5,5a-tetrahydro-1H-2,3-diaza-cyclopropa[a]pentalene-4-carboxylic acid ((S)-1-hydroxycarbamoyl-2,2-dimethyl-propyl)-amide; Compound 831: (S)-3,3-Dimethyl-2-[((1aR,5aR)-2-pyrazin-2-yl-1a,2,5,5a-tetrahydro-1H-2,3-diaza-cyclopropa[a]pentalene-4-carbonyl)-amino]-butyric acid; Compound 832: (1aR,5aR)-2-(4-Oxy-pyrazin-2-yl)-1a,2,5,5a-tetrahydro-1H-2,3-diaza-cyclopropa[a]pentalene-4-carboxylic acid [1-(5-fluoro-pyridin-2-yl)-2,2-dimethyl-propyl]-amide; Compound 833: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(2-hydroxy-ethylcarbamoyl)-2,2-dimethyl-propyl]-amide; Compound 834: (1aR,5aR)-2-(4-Oxy-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 835: (1aR,5aR)-2-(4-Oxy-pyrazin-2-yl)-1a,2,5,5a-tetrahydro-1H-2,3-diaza-cyclopropa[a]pentalene-4-carboxylic acid (tetrahydro-pyran-4-yl)-amide; Compound 836: (1aR,5aR)-2-(4-Oxy-pyrazin-2-yl)-1a,2,5,5a-tetrahydro-1H-2,3-diaza-cyclopropa[a]pentalene-4-carboxylic acid [(R)-1-(5-fluoro-pyridin-2-yl)-2,2-dimethyl-propyl]-amide; Compound 837: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(5-fluoro-pyridin-2-yl)-2,2-dimethyl-propyl]-amide; Compound 838: (1aR,5aR)—(S)-2-tert-Butoxycarbonylamino-3-methyl-butyric acid) 2-{[2-(2,4-difluoro-phenyl)-1a,2,5,5a-tetrahydro-1H-2,3-diaza-cyclopropa[a]pentalene-4-carbonyl]-amino}-2-methyl-propyl ester; Compound 839: (1aR,5aR)—S)-2-Amino-3-methyl-butyric acid (S)-3-methyl-2-{[2-(4-oxy-pyrazin-2-yl)-1a,2,5,5a-tetrahydro-1H-2,3-diaza-cyclopropa[a]pentalene-4-carbonyl]-amino}-butyl ester; Compound 840: (1aR,5aR)—(S)-2-Amino-3-methyl-butyric acid 2-{[((R)-2-(2,4-difluoro-phenyl)-1a,2,5,5a-tetrahydro-1H-2,3-diaza-cyclopropa[a]pentalene-4-carbonyl]-amino}-2-methyl-propyl ester; Compound 841: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide; Compound 842: (1aR,5aR)-Pentanedioic acid mono-(2-{[(1aR,5aR)-2-(2,4-difluoro-phenyl)-1a,2,5,5a-tetrahydro-1H-2,3-diaza-cyclopropa[a]pentalene-4-carbonyl]-amino}-2-methyl-propyl) ester; Compound 843: (1aR,5aR)-2-Pyrazin-2-yl-1a,2,5,5a-tetrahydro-1H-2,3-diaza-cyclopropa[a]pentalene-4-carboxylic acid [(R)-2-hydroxy-1-(tetrahydro-pyran-4-yl)-ethyl]-amide; Compound 844: (1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester; Compound 845: (1aS,5aS)-Pentanedioic acid mono-((S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl) ester; Compound 846: (1aR,5aR)-2-(4-Oxy-pyrazin-2-yl)-1a,2,5,5a-tetrahydro-1H-2,3-diaza-cyclopropa[a]pentalene-4-carboxylic acid [2-hydroxy-1-(tetrahydro-pyran-4-yl)-ethyl]-amide; Compound 847: (1aR,5aR)-2-(4-Cyano-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 848: (1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester; Compound 849: (1aR,5aR)—(S)-2-Amino-3-methyl-butyric acid (S)-2-[(2-pyrazin-2-yl-1a,2,5,5a-tetrahydro-1H-2,3-diaza-cyclopropa[a]pentalene-4-carbonyl)-amino]-2-(tetrahydro-pyran-4-yl)-ethyl ester; Compound 850: (1aR,5aR)-2-(5-Fluoro-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 851: (1aR,5aR)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 852: (1aR,5aR)-2-(4-Oxy-pyrazin-2-yl)-1a,2,5,5a-tetrahydro-1H-2,3-diaza-cyclopropa[a]pentalene-4-carboxylic acid [(R)-2-hydroxy-1-(tetrahydro-pyran-4-yl)-ethyl]-amide; Compound 853: 3-Fluoro-2-{[(1aR,5aR)-2-(5-fluoro-pyridin-2-yl)-1a,2,5,5a-tetrahydro-1H-2,3-diaza-cyclopropa[a]pentalene-4-carbonyl]-amino}-3-methyl-butyric acid methyl ester; Compound 854: (1aR,5aR)-2-(5-Fluoro-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 855: 4,4,4-Trifluoro-2-{[(1aR,5aR)-2-(5-fluoro-pyridin-2-yl)-1a,2,5,5a-tetrahydro-1H-2,3-diaza-cyclopropa[a]pentalene-4-carbonyl]-amino}-3-trifluoromethyl-butyric acid ethyl ester; Compound 856: (1aR,5aR)-2-(6-Fluoro-pyridin-3-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 857: (1aR,5aR)-2-(6-Fluoro-pyridin-3-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 858: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 859: (1aR,5aR)-2-(5-Fluoro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 860: (S)-2-tert-Butoxycarbonylamino-3-methyl-butyric acid (S)-3,3-dimethyl-2-{[[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl ester; Compound 861: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-4,4,4-trifluoro-butyric acid methyl ester; Compound 862: 3-Fluoro-2-{[(1aR,5aR)-2-(6-fluoro-pyridin-3-yl)-1a,2,5,5a-tetrahydro-1H-2,3-diaza-cyclopropa[a]pentalene-4-carbonyl]-amino}-3-methyl-butyric acid methyl ester; Compound 863: (1aR,5aR)-2-(2,4-Difluoro-phenyl)-1a,2,5,5a-tetrahydro-1H-2,3-diaza-cyclopropa[a]pentalene-4-carboxylic acid (2-fluoro-1,1-dimethyl-ethyl)-amide; Compound 864: (1aR,5aR)-2-(6-Fluoro-pyridin-3-yl)-1a,2,5,5a-tetrahydro-1H-2,3-diaza-cyclopropa[a]pentalene-4-carboxylic acid (2-fluoro-1,1-dimethyl-ethyl)-amide; Compound 865: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 866: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 867: (1aR,5aR)-2-(2,4-Difluoro-phenyl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 868: (1aR,5aR)-2-(6-Cyano-pyridin-3-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 869: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-hydroxy-2-methyl-propionic acid methyl ester; Compound 870: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-hydroxy-2-methyl-propionic acid; Compound 871: 3-Fluoro-2-fluoromethyl-2-{[(1aR,5aR)-2-(5-trifluoromethyl-pyrazin-2-yl)-1a,2,5,5a-tetrahydro-1H-2,3-diaza-cyclopropa[a]pentalene-4-carbonyl]-amino}-propionic acid methyl ester; Compound 872: (1aR,5aR)-2-(2,4-Difluoro-phenyl)-1a,2,5,5a-tetrahydro-1H-2,3-diaza-cyclopropa[a]pentalene-4-carboxylic acid ((R)-3,3,3-trifluoro-1-hydroxymethyl-propyl)-amide; Compound 873: (1aR,5aR)-2-(2,4-Difluoro-phenyl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 874: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 875: (1aR,5aR)-2-(5-Trifluoromethyl-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 876: (1aR,5aR)-2-(4-Oxy-pyrazin-2-yl)-1a,2,5,5a-tetrahydro-1H-2,3-diaza-cyclopropa[a]pentalene-4-carboxylic acid (1,1-bis-hydroxymethyl-propyl)-amide; Compound 877: (1aR,5aR)-2-(6-Cyano-pyridin-3-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 878: (1aR,5aR)-2-(6-Fluoro-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 879: (1aR,5aR)-2-(3-Hydroxy-3-methyl-butyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 880: (1aR,5aR)-2-(6-Chloro-pyridin-3-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 881: (1aR,5aR)-2-(4-Iodo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 882: (1aR,5aR)-2-(4-Iodo-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 883: (1aR,5aR)-2-(1-Oxy-pyridin-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 884: (1aR,5aR)-2-(1-Oxy-pyridin-3-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 885: (1aR,5aR)-2-(4-Chloro-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 886: (1aS,5aS)-2-(4-Chloro-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 887: (1aS,5aS)-2-(4-Chloro-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 888: 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 889: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 890: (1aS,5aS)-2-(4-Chloro-pyridin-2-yl)-1a,2,5,5a-tetrahydro-1H-2,3-diaza-cyclopropa[a]pentalene-4-carboxylic acid N'-tert-butyl-hydrazide; Compound 891: (1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 892: (1aS,5aS)-2-(4-Cyano-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 893: (1aS,5aS)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 894: (1aR,5aR)-2-(1-Oxy-pyridin-3-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 895: (1aR,5aR)-2-(4-Chloro-pyridin-2-yl)-1a,2,5,5a-tetrahydro-1H-2,3-diazacyclopropa[a]pentalene-4-carboxylic acid ((S)-1-hydroxymethyl-2-methyl-propyl)-amide; Compound 896: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 897: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 898: (1aR,5aR)-2-(4-tert-Butylcarbamoyl-pyridin-2-yl)-1a,2,5,5a-tetrahydro-1H-2,3-diaza-cyclopropa[a]pentalene-4-carboxylic acid tert-butylamide; Compound 899: (1aR,5aR)-2-(4-Chloro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 900: (1aR,5aR)-2-(4-Chloro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 901: (1aS,5aS)-2-(4-Chloro-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 902: (1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

Compound 903: (1aS,5aS)-2-(4-Chloro-pyridin-2-yl)-1a,2,5,5a-tetrahydro-1H-2,3-diaza-cyclopropa[a]pentalene-4-carboxylic acid N'-(2,2,2-trifluoro-ethyl)-hydrazide; Compound 904: (1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 905: (1aS,5aS)-2-(4-Chloro-pyridin-2-yl)-1a,2,5,5a-tetrahydro-1H-2,3-diaza-cyclopropa[a]pentalene-4-carboxylic acid N'-(1,1-dioxo-tetrahydro-1$\lambda^6$-thiophen-3-yl)-hydrazide; Compound 906: (1aR,5aR)-2-(4-Methoxy-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 907: (1aR,5aR)-2-(4-Methoxy-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 908: (1aR,5aR)-2-(4-Hydroxy-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 909: (1aR,5aR)-2-(4-Hydroxy-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 910: (1aS,5aS)-2-(4-Chloro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 911: (1aS,5aS)-2-(4-Chloro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 912: (1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide; Compound 913: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide; Compound 914: (1aS,5aS)-2-(4-Oxy-pyrazin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 915: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2-methyl-propyl)-amide; Compound 916: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide; Compound 917: (1aR,5aR)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 918: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide; Compound 919: (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 920: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide; Compound 921: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide; Compound 922: (1aS,5aS)-2-(4-Oxy-pyrazin-2-yl)-1a,2,5,5a-tetrahydro-1H-2,3-diaza-cyclopropa[a]pentalene-4-carboxylic acid (3-methyl-oxetan-3-yl)-amide; Compound 923: (1aS,5aS)-3,3-Dimethyl-2-{[(S)-2-(4-oxy-pyrazin-2-yl)-1a,2,5,5a-tetrahydro-1H-2,3-diaza-cyclopropa[a]pentalene-4-carbonyl]-amino}-butyric acid; Compound 924: (1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide; Compound 925: (1aS,5aS)-2-(4-Oxy-pyrazin-2-yl)-1a,2,5,5a-tetrahydro-1H-2,3-diaza-cyclopropa[a]pentalene-4-carboxylic acid (1,1-bis-hydroxymethyl-2-methyl-propyl)-amide; Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide; Compound 927: (1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide; Compound 928: (1aS,5aS)-2-(4-Oxy-pyrazin-2-yl)-1a,2,5,5a-tetrahydro-1H-2,3-diaza-cyclopropa[a]pentalene-4-carboxylic acid (1-methyl-cyclopropyl)-amide; Compound 929: (1aS,5aS)-2-(4-Oxy-pyrazin-2-yl)-1a,2,5,5a-tetrahydro-1H-2,3-diaza-cyclopropa[a]pentalene-4-carboxylic acid (3-trifluoromethyl-oxetan-3-yl)-amide; Compound 930: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and Compound 931: (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

Additionally, chemical genera of the present disclosure and individual compounds, for example those compounds found in the above list including diastereoisomers and enantiomers thereof, encompass all pharmaceutically acceptable salts, solvates, and particularly hydrates, thereof.

The compounds of the Formula Ia of the present disclosure may be prepared according to relevant published literature procedures that are used by one skilled in the art. Exemplary reagents and procedures for these reactions, and specific procedures from the preparation of numerous compounds can be found in International Publication No. WO2011/025541. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment:
Visceral Pain

The analgesic properties of cannabinoids have been recognized for many years. For example, animal studies have demonstrated that the $CB_1/CB_2$ agonists anandamide, THC, CP55,940 and WIN 55212-2 are effective against acute and chronic pain from chemical, mechanical, and thermal pain stimuli (reviewed in Walker and Huang (2002) *Pharmacol. Ther.* 95:127-135; reviewed in Pacher, P et al. (2006) *Pharmacol. Rev.* 58(3): 389-462). In humans, topical administration of the $CB_1/CB_2$ agonist HU-210 attenuates capsaicin-induced hyperalgesia and allodynia (Rukwied, R. et al. (2003) *Pain* 102:283-288), and co-administration of the $CB_1/CB_2$ agonist THC and cannabidiol (nabiximols, trademark Sativex®) provides relief from cancer-associated pain (GW Pharmaceuticals press release Jan. 19, 2005, Jun. 19, 2007) and multiple-sclerosis-associated pain and spasticity (GW Pharmaceuticals press release Sep. 27, 2005, Mar. 11, 2009).

The role of $CB_1$ in mediating these analgesic effects is well-documented (reviewed in Manzanares, J. et al. (2006) *Current Neuropharmacology* 4:239-57; reviewed in Pacher, P. et al. (2006) *Pharmacol. Rev.* 58(3): 389-462). For example, blockade of peripheral or central $CB_1$ leads to hyperalgesia (Richardson, J. D. et al. (1997) *Eur. J. Pharmacol.* 345:145-153; Calignano, A. et al. (1998) *Nature* 394:277-281), whereas $CB_1$ activation by exogenous administration of a $CB_1$ agonist arachidonyl-2-chloroethylamide reduces pain (Furuse, S. et al. (2009) *Anesthesiology* 111 (1):173-86).

Although less well-documented, $CB_2$ also plays a role in mediating analgesic effects of cannabinoids (reviewed in Guindon and Hohmann (2008) *Br. J. Pharmacol.* 153:319-334). For example, systemic delivery of the $CB_2$-selective agonist AM1241 suppresses hyperalgesia induced in the carrageenan, capsaicin, and formalin models of inflammatory pain in rodents (reviewed in Guindon and Hohmann (2008) *Br. J. Pharmacol.* 153:319-334). Local (subcutaneous) or systemic administration of AM1241 also reverses tactile and thermal hypersensitivity in rats following ligation of spinal nerves in the chronic constriction injury model of neuropathic pain (Malan, T. P. et al. (2001) *Pain* 93:239-245; Ibrahim, M. M. et al. (2003) *Proc. Natl. Acad. Sci.* 100(18): 10529-10533), an effect which is inhibited by treatment with the $CB_2$-selective antagonist AM630 (Ibrahim, M. M. et al. (2005) *Proc. Natl. Acad. Sci.* 102(8):3093-8). The $CB_2$-selective agonist GW405833 administered systemically significantly reverses hypersensitivity to mechanical stimuli in rats following ligation of spinal nerves (Hu, B. et al. (2009) *Pain* 143:206-212). Thus, $CB_2$-selective agonists have also been demonstrated to attenuate pain in experimental models of acute, inflammatory, and neuropathic pain, and hyperalgesia.

Accordingly, $CB_2$-specific agonists and/or $CB_1/CB_2$ agonists find use in the treatment and/or prophylaxis of acute nociception and inflammatory hyperalgesia, as well as the allodynia and hyperalgesia produced by neuropathic pain. For example, these agonists are useful as an analgesic to treat pain arising from autoimmune conditions; allergic reactions; bone and joint pain; muscle pain; dental pain; nephritic syndrome; scleroderma; thyroiditis; migraine and other headache pain; pain associated with diabetic neuropathy; fibromyalgia, HIV-related neuropathy, sciatica, and neuralgias; pain arising from cancer; and pain that occurs as an adverse effect of therapeutics for the treatment of disease.

Furthermore, although cannabinoids exert their antinociceptive effects by complex mechanisms involving effects on the central nervous system, spinal cord, and peripheral sensory nerves (reviewed in Pacher, P. et al. (2006) *Pharmacol. Rev.* 58(3): 389-462), an analysis of models of inflammatory and neuropathic pain in mice that are deficient for $CB_1$ only in nociceptive neurons localized in the peripheral nervous system demonstrates that the contribution of $CB_1$-type receptors expressed on the peripheral terminals of nociceptors to cannabinoid-induced analgesia is paramount (Agarwal, N. et al. (2007) *Nat. Neurosci.* 10(7): 870-879). Accordingly, agonists of $CB_1$ that are unable to cross the blood brain barrier still find use in the treatment and/or prophylaxis of acute pain, inflammatory pain, neuropathic pain, and hyperalgesia.

The Cannabinoid system in inflammatory bowel disease (IBD) is dysregulated, and the enzymes that breakdown endocannabinoids (e.g. fatty acid amide hydrolase—FAAH) are increased in active inflammatory Crohn's disease. The enzymes that synthesize endocannabinoids (e.g. N-acyl-phosphatidylethanolamine-specific phospholipase—NAPE-PLD) are decreased in active inflammatory Crohn's disease and some endocannabinoids are decreased in active inflammatory bowel disease.

The $CB_2$ receptors are located in the target tissue gastrointestinal (GI) cells and local immune cells in both humans and in rodents, and are found in epithelial cells, immune cells, and in enteric neurons where $CB_2$ mediated sensitivity is observed at visceral afferent nerve endings.

The $CB_2$ receptor is increased in the ulcerative margin in Crohn's disease, and cannabinoids have been shown to be effective in clinical trials for Crohn's pain. For example, cannabis has been demonstrated to induce a clinical response in patients with Crohn's disease in a prospective placebo-controlled study, and treatment of Crohn's disease with cannabis in an observational study showed improvements in the pain score.

Several preclinical animal studies support these observations which suggest that $CB_2$ activation can alleviate abdominal pain without the unwanted cognitive effects of $CB_1$ receptor activation. A $CB_2$ agonist has been shown to block mesenteric nerve firing and this effect is blocked in $CB_2$ knockouts. Similarly, a reduction of intestinal pain by probiotic *Lactobacillus acidophophilis* (LCFM) administration in a butyrate-induced model of colonic hypersensitivity is blocked by a $CB_2$ receptor antagonist. Thus, selective binding of an agonist to the $CB_2$ receptor over the $CB_1$ receptor is of significance for potential alleviation of pain, without the unwanted cognitive effects of $CB_1$ receptor activation.

The binding affinity, potency, and selectivity of Compound A for recombinant $CB_2$ receptors were determined using radioligand binding assays and GPCR signaling assays. Compound A was shown to be a full agonist of the $CB_2$ receptor with a Ki of 6 nM for human $CB_2$ and EC50 values between 6 nM and 8 nM for the human, rat, and dog receptors. At test concentrations up to 10 µM, Compound A did not interact with recombinant human, rat, or dog $CB_1$ receptors, indicating a >1000-fold selectivity across these species.

Thus, in accordance with the present disclosure, the Compounds of the Formula Ia, for example Compound A, are particularly useful for the treatment of visceral pain, for example abdominal pain; pelvic pain; pain from an internal organ; or pain arising from or related to pancreatitis (e.g., chronic pancreatitis), inflammatory bowel disease, endometriosis, interstitial cystitis, prostatitis (e.g., chronic prostatitis), or post-surgical abdominal lesions. In some embodiments, the visceral pain arises from or is related to inflammatory bowel disease, for example Crohn's disease. The Compounds of the Formula Ia, for example Compound A, are also particularly useful for the treatment of visceral pain in an organ or tissue expressing the $CB_2$ receptor. $CB_2$ receptor expression has been reported, for example, in the spleen, vermiform appendix, lung, terminal ileum of the small intestine, small intestine Peyer's patch, lymph nodes, urinary bladder, stomach, thymus, and sigmoid colon (EMBL-EBI Expression Atlas, accessed Feb. 22, 2017).

The severity of the pain can be assessed with self-reported measures as is known in the art. Generally, pain is assessed at rest, with appropriate activity (e.g., ambulation, cough), at baseline (prior to administration of the compound of Formula Ia or a pharmaceutically acceptable salt, solvate, hydrate, and/or N-oxide thereof and at regular intervals thereafter). Some of the most commonly used pain assessment instruments include the visual analog scale (VAS), numeric rating scale (NRS), and categorical Likert scale. The VAS is a written assessment that typically utilizes an unmarked 100-mm line with the left end marked as "no pain" and the right end marked as "worst pain imaginable." Subjects put a mark on the line corresponding to their level of pain. The NRS can be applied in either written or verbal form and typically utilizes a rating from 0 (corresponding to "no pain") to 10 (corresponding to "worst pain imaginable"). Likert scales are typically four- or five-item instruments (e.g., ratings of "none", "mild", "moderate", "severe") that attempt to quantify pain.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition for alleviation of visceral pain comprising admixing at least one compound according to Formula Ia and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tableting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy,* 20$^{th}$ Edition, 2000, Lippincott Williams & Wilkins, (Editors: Gennaro et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as cannabinoid receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds of the present invention. Some non-limiting preferred dosages for inclusion in the compositions and methods of the present disclosure include: 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85, mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 275 mg, 280 mg, 290 mg, 300 mg, 325 mg, 350 mg, 375 mg, and 400 mg. Multiple doses may be administered during the day, especially when relatively large amounts are deemed to be needed, for example 2, 3, or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations. The daily dose can be divided, especially when relatively large amounts are administered as deemed appropriate, into several, for example 2, 3, or 4-part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectable.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminum, calcium, lithium, magnesium, potassium, sodium, zinc and the like. In some embodiments, the pharmaceutically acceptable metal is sodium. Representative organic bases include, but are not limited to, benzathine ($N^1,N^2$-dibenzylethane-1, 2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

Hydrates and Solvates

It is understood that when the phrase "pharmaceutically acceptable salts, solvates and hydrates" is used when referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Brittan, Vol. 95, Marcel Dekker, Inc., New York, 1999, incorporated herein by reference in its entirety. Accordingly, one aspect of the present invention pertains to hydrates and solvates of compounds of Formula Ia and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, DE), Avantium Technologies (Amsterdam) and Aptuit (Greenwich, CT).

Polymophs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly recently published a polymorph screens of 245 compounds consisting of a "wide variety of structural types" revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026).

EXAMPLES

Example 1: Preparation of Compounds

The preparation of compounds of Formulas Ia-Id, including Compound A, is described in International Patent Application No. PCT/US2010/002360, published as International Publication No. WO2011/025541, the entire contents of which are incorporated herein by reference in their entirety.

The preparation of crystal forms of Compound A, including the anhydrous, non-solvated crystalline form, is described in International Patent Application No. PCT/US2012/026506, published as International Publication No. WO2012/116276, the entire contents of which are incorporated herein by reference in their entirety.

Example 2: Homogeneous Time-Resolved Fluorescence (HTRF®) Assay for Direct cAMP Measurement A: $CB_2$ Assay Compounds were screened for agonists and inverse agonists of $CB_2$ receptor (e.g., human $CB_2$ receptor) using the HTRF® assay for direct cAMP measurement (Gabriel et al., *ASSAY and Drug Development Technologies,* 1:291-303, 2003) in recombinant CHO-K1 cells stably transfected with the $CB_2$ receptor. CHO-K1 cells were obtained from ATCC® (Manassas, VA; Catalog #CCL-61). An agonist of the $CB_2$ receptor was detected in the HTRF® assay for direct cAMP measurement as a compound which decreased cAMP concentration. An inverse agonist of the $CB_2$ receptor was detected in the HTRF® assay for direct cAMP measurement as a compound which increased cAMP concentration. The HTRF® assay also was used to determine $EC_{50}$ values for $CB_2$ receptor agonists and inverse agonists.

B: $CB_1$ Assay

Compounds were also screened for agonists and inverse agonists of the $CB_1$ receptor (e.g., human $CB_1$ receptor) using HTRF® assay for direct cAMP measurement (Gabriel et al., *ASSAY and Drug Development Technologies,* 1:291-303, 2003) in recombinant CHO-K1 cells stably transfected with the $CB_1$ receptor. CHO-K1 cells were obtained from ATCC® (Manassas, VA; Catalog #CCL-61). An agonist of the $CB_1$ receptor was detected in the HTRF® assay for direct cAMP measurement as a compound which decreased cAMP concentration. An inverse agonist of the $CB_1$ receptor was detected in the HTRF® assay for direct cAMP measurement as a compound which increased cAMP concentration. The HTRF® assay also was used to determine $EC_{50}$ values for $CB_1$ receptor agonists and inverse agonists.

Principle of the assay: The HTRF® assay kit was purchased from Cisbio-US, Inc. (Bedford, MA; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the assay: HTRF® assay was carried out using a two-step protocol essentially according to the kit manufacturer's instructions, in 20 µL total volume per well in 384-well plate format (ProxiPlates; PerkinElmer, Fremont, CA; catalog #6008280). To each of the experimental wells was transferred 1500 recombinant CHO-K1 cells in 5 µL phosphate buffered saline containing calcium chloride and magnesium chloride (PBS+; Invitrogen, Carlsbad, CA; catalog #14040) followed by test compound in 5 µL assay buffer (PBS+supplemented with 0.2% BSA, 4 µM forskolin and 1 mM IBMX (Sigma-Aldrich, St. Louis, MO; catalog #s A8806, F6886 and 15879 respectively). The plate was then incubated at room temperature for 1 hour. To each well was then added 5 µL cAMP-d2 conjugate in lysis buffer and 5 µL Cryptate conjugate in lysis buffer according to the kit manufacturer's instructions. The plate was then further incubated at room temperature for 1 hour, after which the assay plate was read.

Assay readout: The HTRF® readout was accomplished using a PHERAstar (BMG Labtech Inc., Durham, NC) or an EnVision™ (Perkin Elmer, Fremont CA) microplate reader.

Certain compounds of the present invention and their corresponding $EC_{50}$ values are shown in Table A-1.

TABLE A-1

| Compound No. | $EC_{50}$ $hCB_1$ (nM) | $EC_{50}$ $hCB_2$ (nM) |
|---|---|---|
| 269 | NR | 809 |
| 332 | NR | 2.0 |
| 340 | NR | 6.28 |
| 368 | 354.4 | 35.04 |
| 408 | 26,900 | 75.8 |
| 632 | NR | 0.966 |
| 634 | 1.1 | 0.170 |

NR = No Response

Certain other compounds of the invention had $hCB_1$ $EC_{50}$ values ranging from about 279 pM to about 76.47 µM in this assay and $hCB_2$ $EC_{50}$ values ranging from about 170 pM to about 44.72 µM in this assay. Certain other compounds of the invention had $hCB_2$ $EC_{50}$ values ranging from about 94 pM to about 2.7 nM in this assay.

Certain compounds of the present invention and their corresponding $EC_{50}$ values are shown in Table A-2.

TABLE A-2

| Compound No. | EC$_{50}$ hCB$_1$ (nM) | EC$_{50}$ hCB$_2$ (nM) |
|---|---|---|
| 151 | 72,500 | 3.83 |
| 174 | NR | 38.2 |
| 264 | NR | 10.1 |
| 309 | NR | 19 |
| 493 | NR | 3.98 |
| 515 | NR | 4.32 |
| 593 | NR | 7.15 |
| 625 | NR | 4.45 |
| 642 | NR | 4.38 |
| 644 | NR | 0.7 |
| 667 | 195 | 0.3 |
| 684 | NR | 7.08 |
| 690 | NR | 1.79 |
| 696 | NR | 6.89 |
| 698 | NR | 10.2 |
| 699 | 9,770 | 0.4 |
| 700 | NT | 3.14 |
| 704 | NT | 0.2 |
| 764 | NT | 0.5 |
| 765 | NT | 0.1 |
| 820 | NT | 2.62 |
| 821 | NT | 0.6 |
| 841 | NT | 1.4 |
| 919 | NT | 0.2 |
| 921 | NT | 0.2 |
| 924 | NT | 0.8 |
| 926 | NT | 0.2 |

NR = No Response;
NT = Not Tested

Example 3: PathHunter β-Arrestin Assay

A: CB$_2$ Assay

Compounds were screened for agonists of the human CB$_2$ receptor using the DiscoveRx PathHunter β-arrestin assay which measures the β-arrestin binding to the CB$_2$ receptor upon its activation. CB$_2$ was cloned into the pCMV-PK vector (DiscoveRx, Fremont, CA; catalog #93-0167) and transfected into the CHO-K1 EA-Arrestin parental cell line (DiscoveRx, Fremont, CA; catalog #93-0164). CHO-K1 positive clones stably expressing the CB$_2$-ProLink fusion protein were identified by their responses to the CB$_2$ agonist CP55,940. Clone #61 was chosen for its big agonist window and homogenous expression as detected by anti-HA flow cytometry.

Principle of the assay: The PathHunter-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active b-galactosidase enzyme which can be measured using the chemiluminescent PathHunter Flash Detection Kit (DiscoveRx, Fremont, CA: catalog #93-0001).

The assay: The stable CHO-K1 cells expressing CB$_2$-Prolink fusion protein were plated overnight in 384-well plates (Optiplate 384-Plus, PerkinElmer, Fremont CA; catalog #6007299) at 5000 cells/5 μL/well in the Opti-MEM medium (Invitrogen, Carlsbad, CA; catalog #31985088) with 1% FBS. 5 μL of test compound diluted in Opti-MEM supplemented with 1% BSA was transferred to each well of the Optiplate. The plates were then incubated at 37° C./5% CO$_2$ for two hours. 12 μL of substrate prepared from the PathHunter Flash Detection Kit (DiscoveRx, Fremont, CA: catalog #93-0001) was transferred to each well of the Optiplate. The plate was then incubated in the dark at room temperature for 2 h, after which the assay plate was read.

Assay readout: β-Arrestin assay readout was accomplished using a PHERAstar (BMG Labtech Inc., Durham, NC) or an EnVision™ (PerkinElmer, Fremont CA) microplate reader.

B: CB$_1$ Assay

Compounds were screened for agonists of the human CB$_1$ receptor using the DiscoveRx PathHunter β-arrestin assay which measures the β-arrestin binding to the CB$_1$ receptor upon its activation. CB$_1$ was cloned into the pCMV-PK vector (DiscoveRx, Fremont, CA; catalog #93-0167) and transfected into the CHO-K1 EA-Arrestin parental cell line (DiscoveRx, Fremont, CA; catalog #93-0164). CHO-K1 positive clones stably expressing the CB$_1$-ProLink fusion protein were identified by their responses to the CB$_1$ agonist CP55,940. Clone #3 was chosen for its big agonist window and homogenous expression as detected by anti-HA flow cytometry Principle of the assay: The PathHunter β-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger b-galactosidase fragment, EA (Enzyme Acceptor). Binding of β-arrestin to the activated GPCR causes the complementation of the two enzyme fragments, forming an active b-galactosidase enzyme which can be measured using the chemiluminescent PathHunter Flash Detection Kit (DiscoveRx, Fremont, CA: catalog #93-0001).

The assay: The stable CHO-K1 cells expressing CB$_1$-Prolink fusion protein were plated overnight in 384-well plates (Optiplate 384-Plus, PerkinElmer, Fremont CA; catalog #6007299) at 5000 cells/5 μL/well in the Opti-MEM medium (Invitrogen, Carlsbad, CA; catalog #31985088) with 1% FBS. 5 μL of test compound diluted in Opti-MEM supplemented with 1% BSA was transferred to each well of the Optiplate. The plates were then incubated at 37° C./5% CO$_2$ for two h. 12 μL of substrate prepared from the PathHunter Flash Detection Kit (DiscoveRx, Fremont, CA: catalog #93-0001) was transferred to each well of the Optiplate. The plate was then incubated in the dark at room temperature for 2 h, after which the assay plate was read.

Assay readout: β-Arrestin assay readout was accomplished using a PHERAstar (BMG LABTECH Inc., Durham, NC) or EnVision™ (PerkinElmer, Fremont CA) microplate reader.

Certain compounds of the present invention and their corresponding EC$_{50}$ values are shown in Table B-1.

TABLE B-1

| Compound No. | EC$_{50}$ hCB$_1$ (nM) | EC$_{50}$ hCB$_2$ (nM) |
|---|---|---|
| 631 | NR | 107.7 |
| 633 | NR | 3.20 |
| 673 | 1,009 | 0.6437 |
| 711 | NR | 28.1 |
| 728 | 251.1 | 1.1 |

NR = No Response

Certain other compounds of the invention had hCB$_1$ EC$_{50}$ values ranging from about 2.6 nM to about 89.06 μM in this assay and hCB$_2$ EC$_{50}$ values ranging from about 643 pM to about 7 μM in this assay. Certain other compounds of the invention had hCB$_1$ EC$_{50}$ values ranging from about 10.9 nM to about 100 μM in this assay and hCB$_2$ EC$_{50}$ values ranging from about 384 pM to about 100 μM in this assay.

Certain compounds of the present invention and their corresponding EC$_{50}$ values are shown in Table B-2.

TABLE B-2

| Compound No. | EC$_{50}$ hCB$_1$ (nM) | EC$_{50}$ hCB$_2$ (nM) |
|---|---|---|
| 151 | NR | 92.1 |
| 174 | NR | 167 |
| 309 | NT | 136 |
| 493 | NR | 63.6 |
| 593 | 1,330 | 34.6 |
| 625 | NR | 11.8 |
| 642 | NR | 26.4 |
| 644 | 4,470 | 4.69 |
| 646 | NR | 925 |
| 667 | 145 | 1.53 |
| 683 | NR | 3,000 |
| 684 | NR | 59 |
| 690 | NR | 31 |
| 696 | NR | 49.4 |
| 698 | NR | 27.9 |
| 699 | NR | 6.36 |
| 700 | NR | 31.5 |
| 703 | NR | 603 |
| 704 | 228 | 0.8 |
| 722 | NR | 34 |
| 746 | 142 | 0.7 |
| 764 | NR | 5.92 |
| 765 | NR | 1.16 |
| 766 | NR | 4.57 |
| 767 | NR | 66.6 |
| 820 | NR | 38.4 |
| 821 | NR | 7.12 |
| 828 | NT | 4.14 |
| 841 | 1,140 | 17.5 |
| 848 | NR | 50 |
| 889 | 4,070 | 8.6 |
| 891 | 11,800 | 16.2 |
| 896 | NR | 43.5 |
| 897 | 951 | 3.79 |
| 902 | NR | 77.5 |
| 904 | NR | 31.4 |
| 912 | NT | 9.49 |
| 913 | NR | 105 |
| 918 | 437 | 1.01 |
| 919 | NR | 2.35 |
| 920 | NT | 4.6 |
| 921 | NR | 2.59 |
| 924 | NR | 10.5 |
| 926 | NR | 4.43 |
| 927 | NR | 9.39 |
| 930 | NR | 17 |
| 931 | NR | 20.8 |

NR = No Response;
NT = Not Tested

Example 4: Radioligand Binding Assay

Preparation of Membranes: HTEK293 cells stably expressing human CB$_2$ receptor were collected, washed in ice cold PBS, and centrifuged at 48,000×g for 20 min at 4° C. The cell pellet was then collected, resuspended in wash buffer (20 mM HEPES, pH 7.4 and 1 mM EDTA), homogenized on ice using a Brinkman Polytron, and centrifuged at 48,000×g for 20 min at 4° C. The resultant pellet was resuspended in ice cold 20 mM HEPES, pH 7.4, homogenized again on ice, recentrifuged for 20 min at 4° C., and membrane pellets were then stored at −80° C. until needed.

[$^3$H]CP55,940 and [$^3$H]WIN55,212-2 Radioligand Binding Assays: Radioligand binding assays for human CB$_2$ receptors were performed using two different agonist radioligands, [$^3$H]CP55,940 and [$^3$H]WIN55,212-2 and similar assay conditions. For both assays, nonspecific binding was determined in the presence of 10 mM unlabeled compound. Competition experiments consisted of addition of 20 mL of assay buffer (50 mM Tris, pH 7.4, 2.5 mM EDTA, 5 mM MgCl$_2$, and 0.5 mg/mL of fatty acid free BSA) containing test compound (concentrations ranging from 1 pM to 100 μM), 25 μL of radioligand (1 nM final assay concentration for [$^3$H]CP55,904 and [$^3$H]WIN55,212-2), and 50 mL of membranes (20 mg/mL final protein for both assays). Incubations were conducted for 1 hour at room temperature, assay plates were filtered under reduced pressure over GF/B filters, washed with assay buffer and dried overnight in a 50° C. oven. Then, 25 μL of BetaScint scintillation cocktail was added to each well, and plates were read in a Packard TopCount scintillation counter.

Certain compounds of the present invention and their corresponding K$_i$ values are shown in Table C.

TABLE C

| Compound No. | K$_i$ hCB$_1$ (nM) | K$_i$ hCB$_2$ (nM) |
|---|---|---|
| 64 | 207 | 97.6 |
| 629 | NR | 97.7 |
| 701 | 105.1 | 1.45 |
| 752 | 568.4 | 58.7 |
| 755 | 1,200 | 3.8 |

NR = No Response

Certain other compounds of the invention had hCB$_1$ K$_i$ values ranging from about 124 nM to about 19.36 μM in this assay and hCB$_2$ K$_i$ values ranging from about 3.22 nM to about 4.69 μM in this assay.

Example 5: Effect of Compounds on Osteoarthritis Pain

Injection of monosodium iodoacetate (MIA) into a joint (Kalbhen, 1987) inhibits the activity of glyceraldehyde-3-phosphate dehydrogenase in chondrocytes, resulting in disruption of glycolysis and eventually in cell death. The progressive loss of chondrocytes results in histological and morphological changes of the articular cartilage, closely resembling those seen in osteoarthritis patients.

The osteoarthritis was induced in 200 g male Sprague Dawley rats. After brief anesthesia by isoflurane rats received a single intra-articular injection of MIA (2 mg) (Sigma Aldrich, Saint Louis, MO, USA; Cat #19148) dissolved in 0.9% sterile saline in a 50 μL volume administered through the patella ligament into the joint space of the left knee with a 30 G needle. Following the injection, animals were allowed to recover from anesthesia before being returned to the main housing vivarium.

Typically, during disease progression, there was an inflammation period of 0-7 days post-intra-articular injection followed by progressive degeneration of the cartilage and subchondral bone from days 14-55. Efficacy studies with a compound of the present invention for pain development took place from day 14 onwards and were performed twice a week with at least 3 days' wash-out in between each assay. Three different assays were used to measure pain. Tactile allodynia was measured via von Frey assay, hind limb paw weight distribution was monitored using an incapacitence tester (Columbus Instruments, Columbus, OH, USA) and hind limb grip strength was measured using a grip strength meter (Columbus Instruments, Columbus, OH, USA). Briefly, the von Frey assay was performed using the standard up down method with von-Frey filaments. Hind paw weight distribution was determined by placing rats in a chamber so that each hind paw rests on a separate force plate of the incapacitence tester. The force exerted by each hind limb (measured in grams) is averaged over a 3 second period. Three measurements were taken for each rat, and the change in hind paw weight distribution calculated. Peak hind limb grip force was conducted by recoding the maximum compressive force exerted on the hind limb mesh gauge set on the grip strength meter. During the testing, each rat was restrained, and the paw of the injected knee was allowed to grip the mesh. The animal was then pulled in an upward motion until their grip was broken. Each rat is tested 3 times, with the contralateral paw used as a control.

Figure 2:
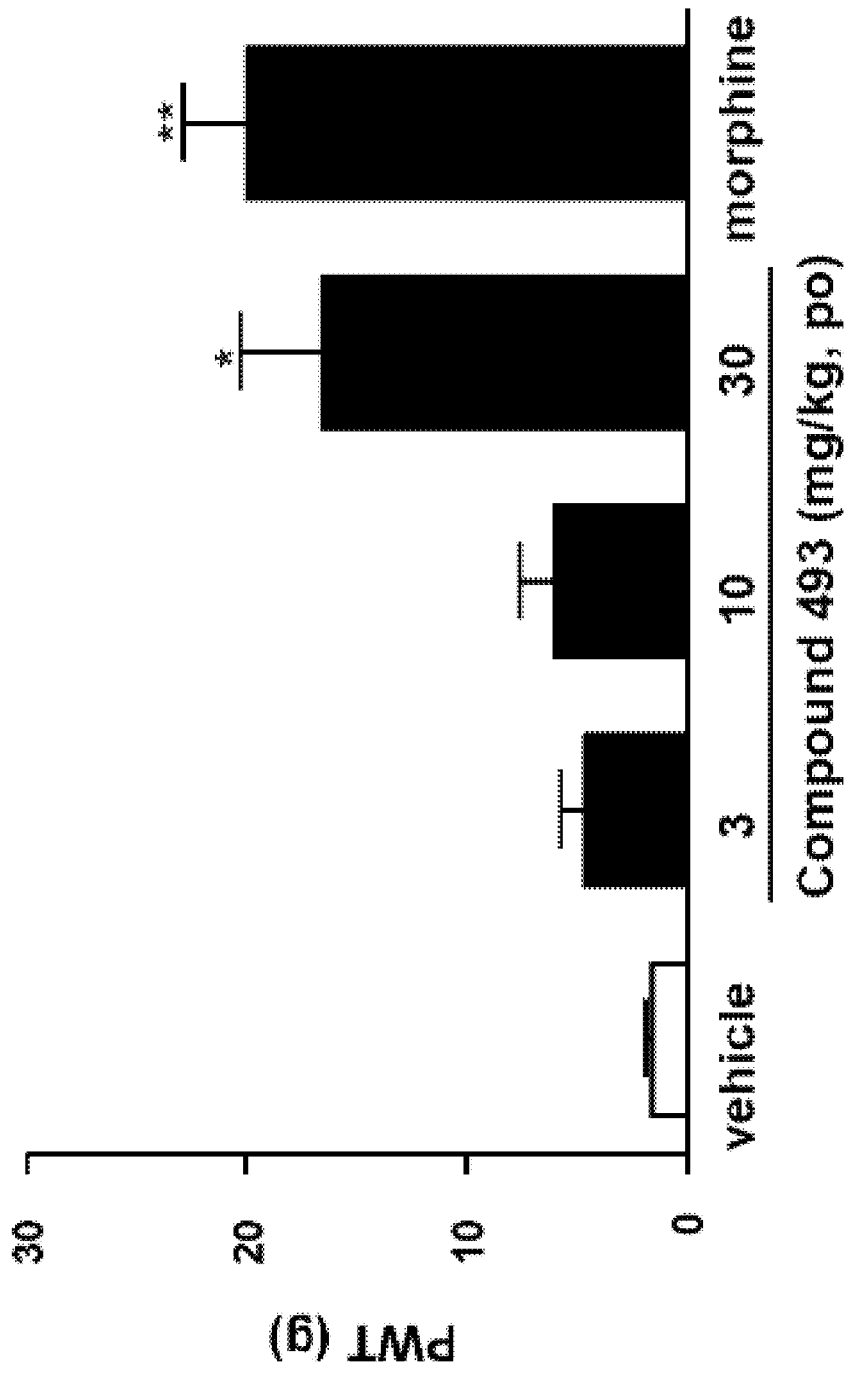
FIG. 2 shows the effect of Compound 493 in the monosodium iodoacetate (MIA) model of osteoarthritis in rats at 1-hour post dosing. See Example 5.

Animals were base-lined prior to treatment of the test compound. The MIA treated groups of rats (6 per group) were then dosed with either vehicle (PEG400, orally), Compound 493 (at 3 mg/kg, 10 mg/kg, and 30 mg/kg, orally) or with morphine (3 mg/kg, subcutaneously). Dosing volume was 500 µL. One hour after dosing, von Frey assay, hind limb weight distribution and/or hind limb grip analysis was performed to measure the efficacy of the test compound. Increase in paw withdrawal threshold (PWT) by Compound 493 in comparison with vehicle shown in FIG. 2 was indicative of the test compound exhibiting therapeutic efficacy in the MIA model of osteoarthritis.

Example 6: Effects of Compounds on Skin-Incision Model in Rats

Postoperative pain was produced by a 1 cm incision of the skin and muscle of the plantar surface of the rat hind paw as described (Brennan et al., 1996), with minor modifications. For surgery, rats weighing 200 to 300 g were anesthetized with 2% isoflurane. The plantar surface of the right hind paw was prepared in a sterile manner with a 10% povidone-iodine solution. A 1 cm longitudinal incision was made with a number 11 blade, through skin and fascia of the plantar aspect of the foot, starting in the middle of the paw and extending toward the heel. The plantaris muscle was elevated and incised longitudinally. After hemostasis with gentle pressure, the skin was apposed with 2 mattress sutures of 5-0 nylon. The animals were allowed to recover individually in their cages with clean bedding.

Figure 4:
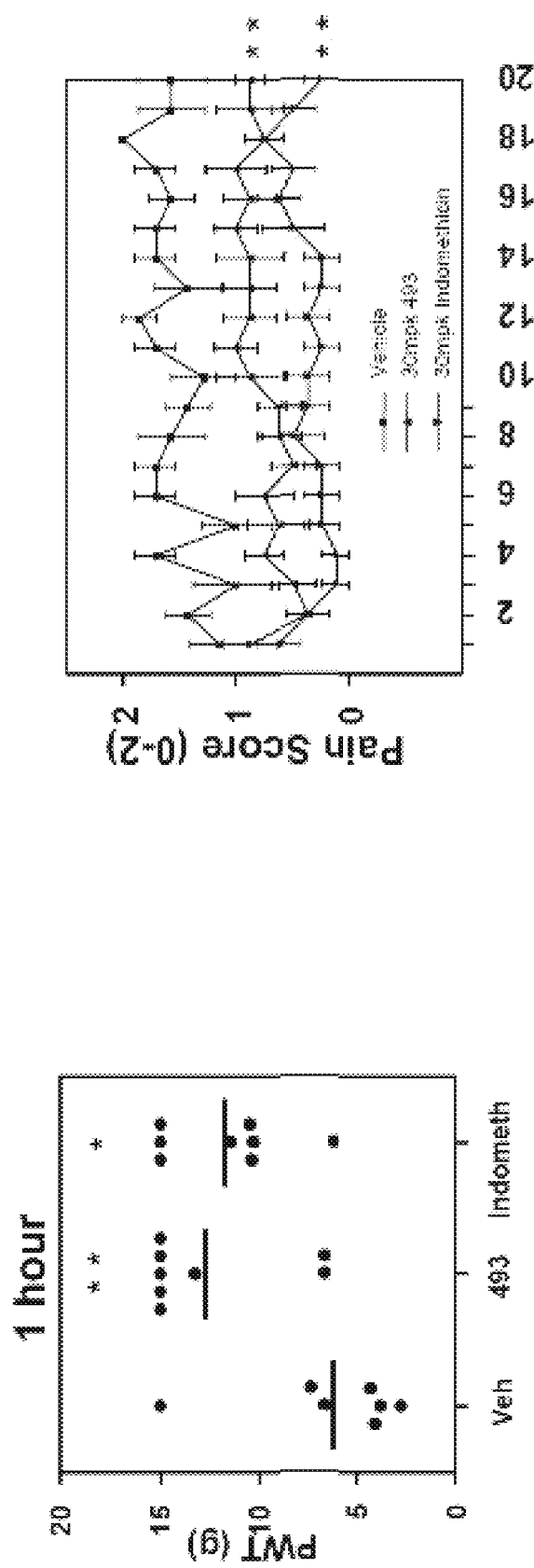
FIG. 4 shows the effect of Compound 493 on the skin incision model of post-operative pain in rats. See Example 6.

Two to three hours after surgery, animals were treated with the test compound. Compound 493 were dosed orally at 30 mg/kg. Tactile allodynia was assessed with von Frey hair calibrated to bend at specific weights (0.4, 1, 2, 4, 6, 8, 15 g for animal weighing less than 250 g; 1, 2, 4, 6, 8, 15, 26 g for animal weighing 250 g or more in some experiments). Regions adjacent to incision on the mid-plantar surface were first probed to assess the responsive spots with a von Frey force of 8 g. If there was no withdrawal response, the next higher force (15 g) was used until no response at the highest force (26 g for rats weighing 250 g or higher, 15 g for rats weighing less than 250 grams). Once responsive spot was identified, the 50% withdrawal threshold was then determined using the up/down method (Chaplan et al., 1994). Each trial started with a von Frey force of 2 g, if there was no withdrawal response, the next higher force was delivered. If there was a response, the next lower force was delivered. This procedure was performed until no response was made at the highest force (15 g or 26 g depending on animal size) or until four stimuli were delivered following the initial response. The 50% paw withdrawal threshold (PWT) was then calculated as described in Chaplan et al., 1994 (Chaplan S. R., Bach F. W., Pogrel J. W., Chung J. M., Yaksh T. L.: Quantitative assessment of tactile allodynia in the tat paw. *J. Neuroscience Methods* 1994, 531(1):1022-1027). FIG. 4 shows the pain response of the animals treated with Compound 493 (dosed orally at 30 mg/kg) compared with vehicle and indomethacin (dosed at 30 mg/kg).

Example 7: Effect of Compounds on FCA-Induced Hyperalgesia in Rats

Animal info: Male Sprague Dawley rats from Harlan (200-225 g when received) were used. Upon arrival, rats were housed 4 per cage in shoe-box polycarbonate cages with wire tops, wood chip bedding and suspended food and water bottles. Animals were acclimated for 5-7 days prior to being injected with Freund's complete adjuvant (FCA) (Sigma; catalog #5881).

Experimental procedure: 2 days (48 h) before testing compounds, baseline readings of all rats were taken right before FCA injection. Rats were then injected with 50 µL FCA containing 1 mg/mL Mtb (*Mycobacterium tuberculosis*) in right hind footpad under inhalation anesthesia (isoflurane). 48 hours after FCA injection, readings were taken as pre-dosing baseline and then rats were dosed orally with 0.5 mL of vehicle or compound (0.5 mL per 250 g rat). Readings were taken again at 1-hour post dosing. All readings were taken with an Analgesy-Meter (Ugo Basile) which measures mechanical hyperalgesia via paw pressure.

Clinical scoring: FCA-induced hyperalgesia was tested with an Analgesy-Meter. Briefly, the Analgesy Meter applied an increasing pressure to the right hind paw. The paw withdrawal threshold was the pressure leading to withdrawal.

Drug treatment: 48 hours after FCA injection, baseline readings were taken prior to dosing of compounds, and then rats were dosed orally with vehicle (PEG400) or Compound 493 at 0.1, 1, 3, 10 and 30 mg/kg. Meanwhile a group of rats were dosed orally with 50 mg/kg of Diclofenac as a positive control. Readings were taken again at 1-hour post dosing. Dosing volume was 500 µL per 250 g rat. As is apparent from FIG. 1, an increase in paw withdrawal threshold (PWT) for Compound 493 in comparison with the vehicle indicates Compound 493 exhibited therapeutic efficacy in the FCA-induced hyperalgesia model of inflammatory pain at 1-hour post dosing.

Example 8: Paclitaxel-Induced Allodynia in Sprague Dawley Rats

The mitotic inhibitor, paclitaxel (Taxol®) is one of the most effective and frequently used chemotherapeutic agents for the treatment of solid tumors as well as ovarian and breast cancers. Therapy however is often associated with the unwanted side effects of painful peripheral neuropathy.

Animals: Male Sprague Dawley rats [200-250 g] (Harlan Laboratories Inc., Livermore, CA) were housed three per cage and maintained in a humidity-controlled (40-60%) and temperature-controlled (68-72° F.) facility on a 12 h:12 h light/dark cycle (lights on at 6:30 am) with free access to food (Harlan Teklad, Orange, CA, Rodent Diet 8604) and water. Rats were allowed one week of habituation to the animal facility before starting treatment.

Induction of Allodynia: Rats were treated intraperitoneally, with 2 mg/kg of paclitaxel (Sigma Aldrich, Saint Louis, MO) in 10% Cremophor vehicle (500 µL) on days 0, 2, 4, and 6.

Clinical scoring: Tactile allodynia was tested using von Frey filaments. Briefly, the von Frey assay was performed using the standardized up down method with von Frey filaments, that determine the tactile sensitivity of the paw. By applying the increasingly or decreasingly thicker filaments to the paw in a logarithmic scale of actual force, a linear scale of perceived intensity is determined.

Figure 3:
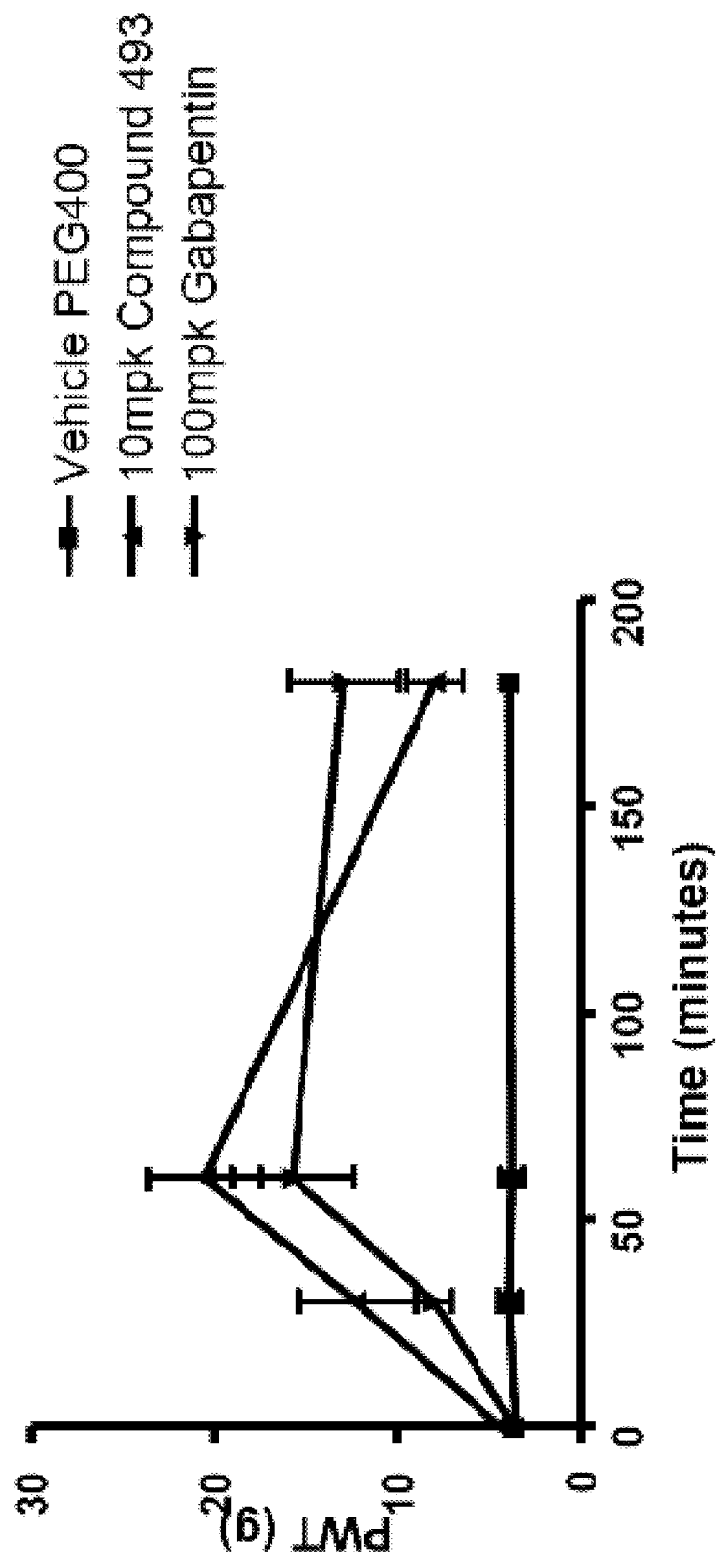
FIG. 3 shows the effect of 10 mg/kg of Compound 493 on paclitaxel-induced allodynia in rats. See Example 8.

Drug treatment: Eight days after the start of paclitaxel dosing, a baseline measurement (von Frey assay) was performed prior to dosing of compounds. The paclitaxel treated groups of rats (6 per group) were dosed orally, with vehicle (PEG400) or 10 mg/kg Compound 493. As a positive control, rats were dosed intraperitoneally with 100 mg/kg gabapentin in water. The dosing volume for oral and peritoneal treatment was 500 µL. The von Frey assay was performed to measure the efficacy of the test compound 30, 60 and 180 minutes after dosing. An increase in paw withdrawal threshold (PWT) by treatment with Compound 493 in comparison with vehicle and gabapentin was indicative of the test compound exhibiting therapeutic efficacy in paclitaxel model of cancer pain. The time course shows maximum efficacy at 1-hour post-dosing. See FIG. 3.

Example 9: Effects of Compounds on Body Temperature and Locomotor Activity in Rats Animals: Male Sprague-Dawley rats (300-400 g) were housed three per cage and maintained in a humidity-controlled (30-70%) and temperature-controlled (20-22° C.) facility on a 12 h:12 h light/dark cycle (lights on at 7:00 am) with free access to food (Harlan-Teklad, Orange, CA, Rodent Diet 8604) and water. Rats were allowed one week of habituation to the animal facility before testing.

Measurement of body temperature and locomotor activity: Body temperature was measured using a stainless-steel rat temperature probe connected to a temperature display device (Physitemp TH-5). The probe was inserted rectally to a depth of 1 inch and the reading was recorded approximately 10 s after insertion, when the reading had stabilized. Body temperature was measured immediately before (time 0) and 60 min post-administration of compounds. Locomotor activity was measured using the Hamilton-Kinder Motor Monitor system, which detected blockage of photocell beams in a standard rat cage and transfers this data to a computer. Motor activity was measured for 30 min starting immediately after the second body temperature measurement, from 60 to 90 min post-administration. Compounds were dosed orally in a volume of 2 to 6 mL/kg, suspended or dissolved in 100% PEG 400.

Figure 5:
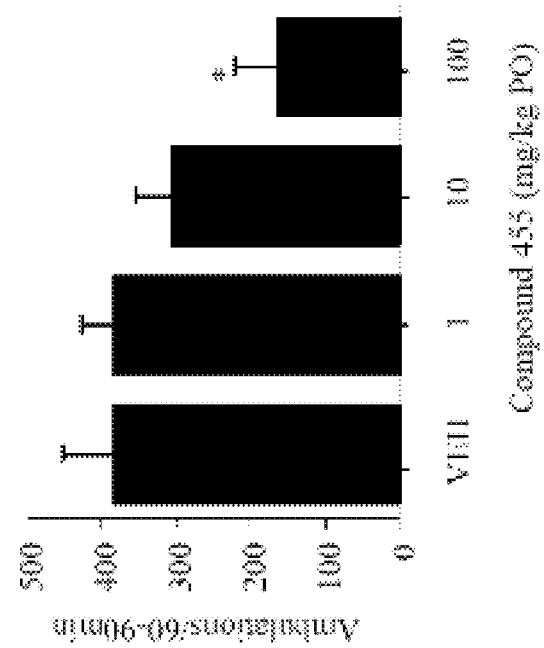
FIG. 5 shows the effect of Compound 455 on body temperature and locomotor activity in rats. See Example 9.
Figure 5:
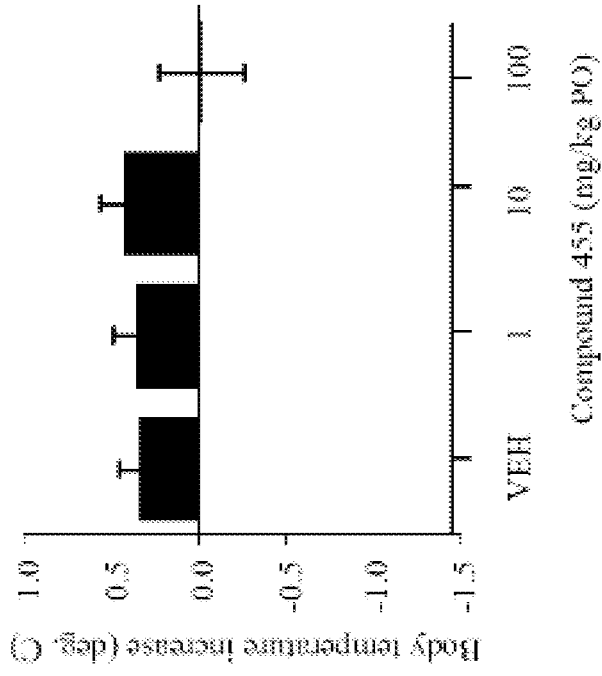
Figure 6:
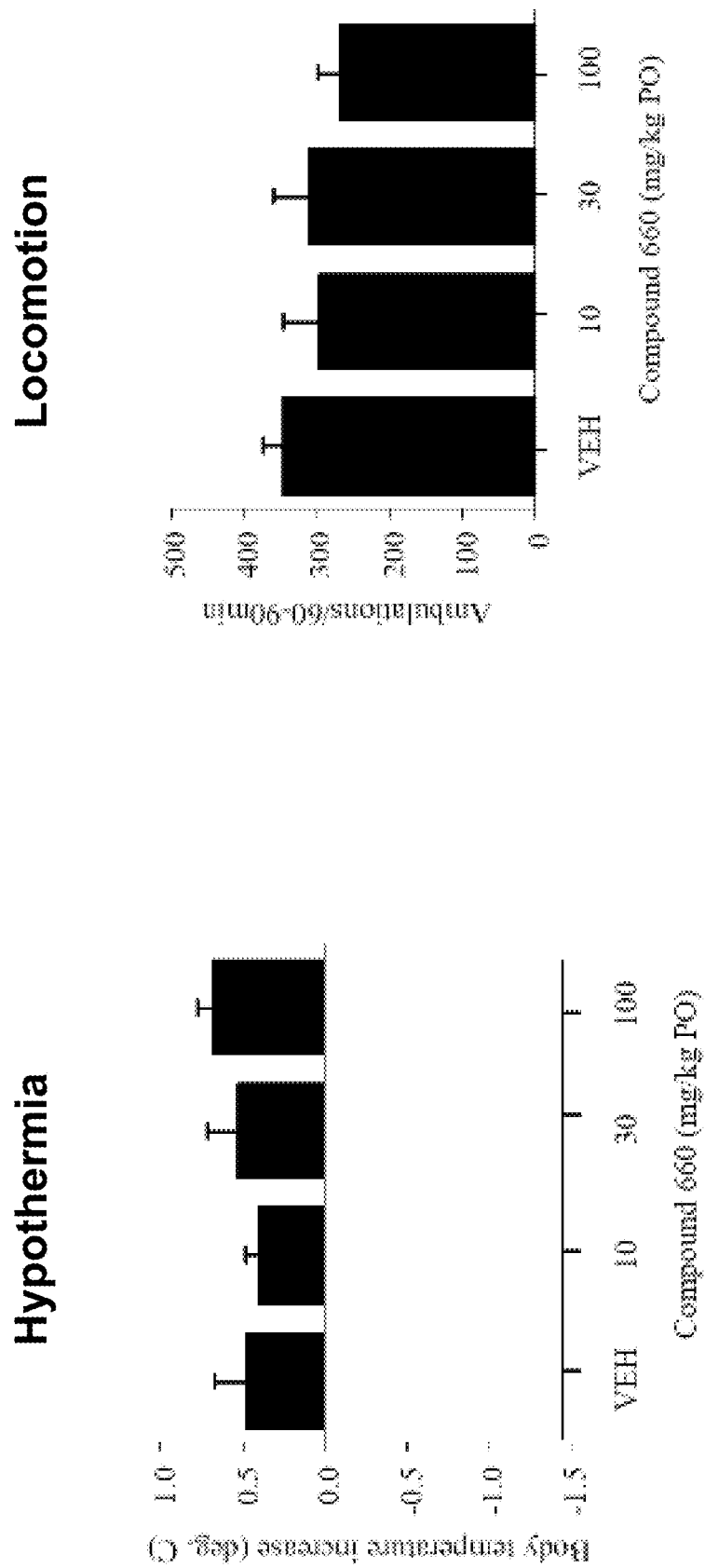
FIG. 6 shows the effect of Compound 660 on body temperature and locomotor activity in rats. See Example 9.
Figure 7:
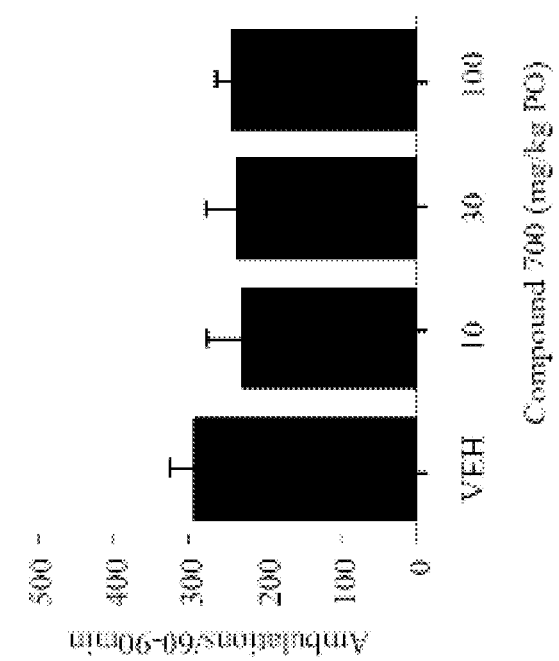
FIG. 7 shows the effect of Compound 700 on body temperature and locomotor activity in rats. See Example 9.
Figure 7:
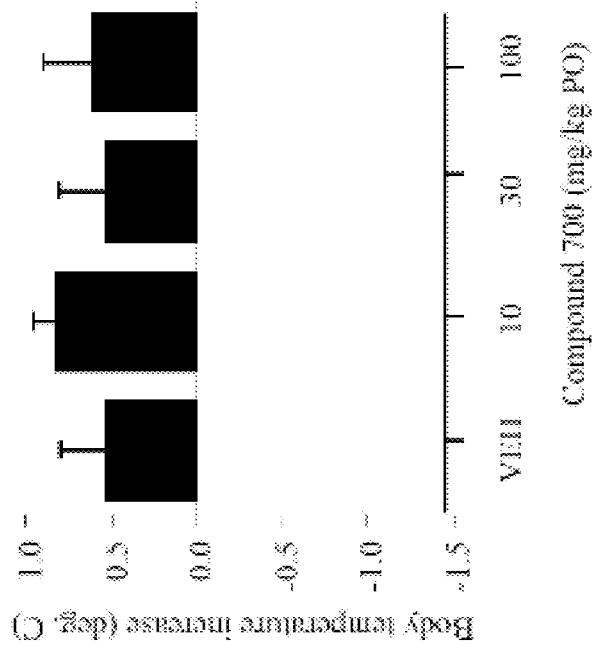
Figure 8:
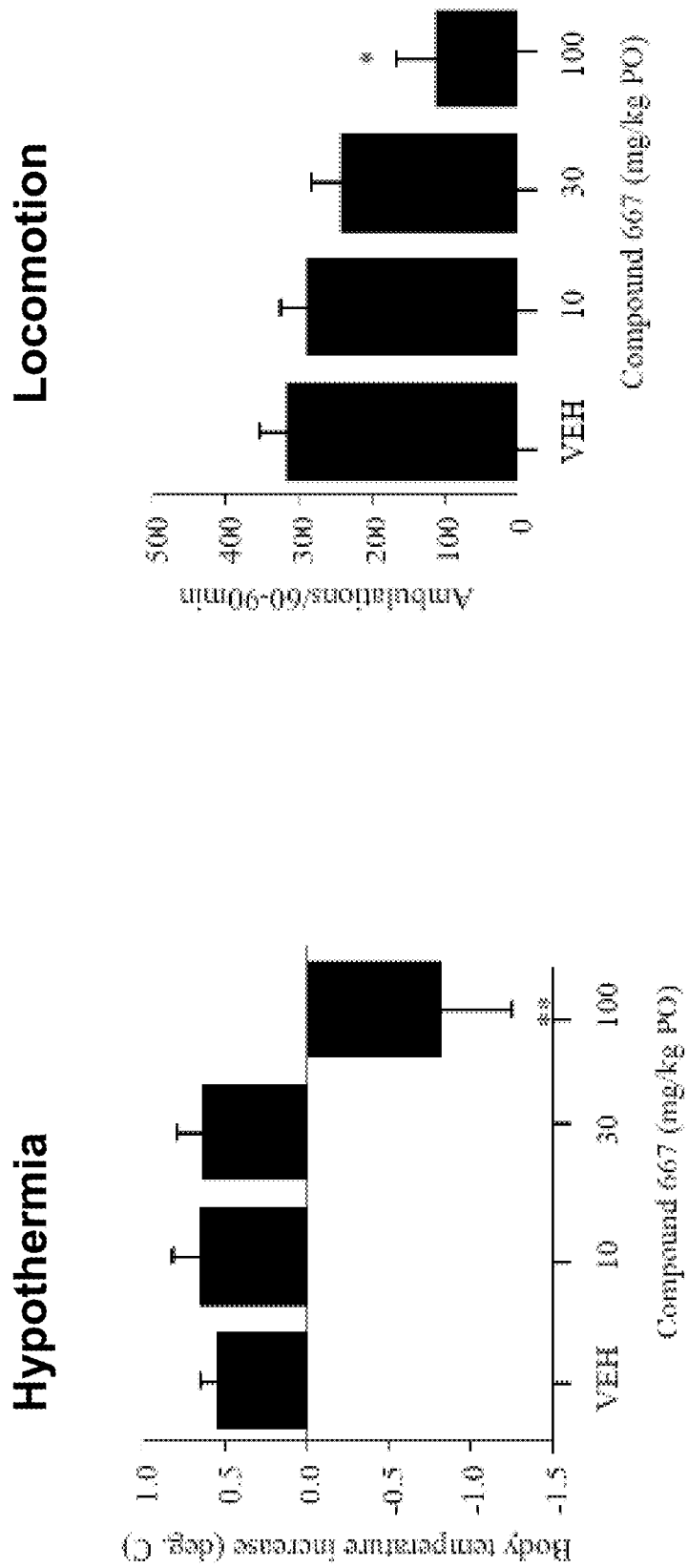
FIG. 8 shows the effect of Compound 667 on body temperature and locomotor activity in rats. See Example 9.

FIGS. 5 to 8 showed the effects of 4 different compounds on body temperature and locomotor activity in rats. The compounds depicted in FIG. 6 and FIG. 7 were inactive in these tests at doses ranging from 1 to 100 mg/kg PO. In FIG. 5, the compound decreased body temperature at the highest dose tested (100 mg/kg), but this effect was not statistically significant; the compound did, however, significantly reduce motor activity. In FIG. 8, the compound significantly decreased both body temperature and locomotor activity at the highest dose tested (100 mg/kg).

Example 10: Effects of Compounds on Spinal Nerve Ligation Surgery

Rats receive nerve injury by tight ligation of L5 and L6 spinal nerves close to the spine, before they join (along with L4) to form the sciatic nerve. For this surgery, animals are placed under general anesthesia using continuous inhalation of isoflurane. Surgery is performed in a dedicated surgery room, using sterile instruments, surgical gloves, and aseptic procedures to prevent clinical infections. The surgical site is shaved and disinfected with iodine solution and alcohol. Animals are observed continuously for their level of anesthesia, testing for the animal's reflex response to tail or paw pinch. A heating pad is used to maintain body temperature both during the procedure and while the animals are recovering from anesthesia. For this procedure, a skin incision is made over the lower back at the level of L4-L6, and the muscle, ligaments, and facet joints are cut away from the spine. Correct location is confirmed by identifying the pelvis and the L5 transverse process. The L5 transverse is carefully removed to expose the L4 and L5 nerves. L5 is carefully hooked (with a pulled glass hook) without damaging L4 and tightly ligated (6-0 silk suture). L6 is then located just under the pelvic bone, hooked and ligated as well. The wound is debrided and closed with internal sutures and external staples. Animals are administered a post-surgery injection of lactated Ringer's solution and returned to their home cages. They are carefully monitored until completely recovered from anesthesia (defined as the ability to move without significant ataxia), typically less than 10 min. Any animal with loss of motor control of the affected hind paw (L4 motor damage) are euthanized. Neuropathic animals are first tested 7-10 days post-surgery for the beginning of tactile allodynia. The allodynia is seen approximately 14 days post-surgery and persists for 45-50 days post-surgery. During this time, analgesic compounds are tested for their ability to reduce or eliminate this chronic pain symptom.

Example 11: Effects of Compounds on Chronic Constriction Injury Surgery

Nerve injury is induced by loose ligature of the sciatic nerve. For this surgery, animals are placed under general anesthesia using continuous inhalation of isoflurane. Surgery is performed in a dedicated surgery room, using sterile instruments, surgical gloves, and aseptic procedures to prevent clinical infections. The surgical site is shaved and disinfected with iodine solution and alcohol. Animals are observed continuously for their level of anesthesia, testing for the animal's reflex response to tail or paw pinch and closely monitoring the animal's breathing. A heating pad is used to maintain body temperature while the animals are recovering from anesthesia. For this procedure, a skin incision is made over the femur and the muscle is bluntly dissected to expose the sciatic nerve. Four loose ligatures (Chromic gut absorbable suture) are placed around the nerve, and the wound is closed with internal sutures and external staples. Animals are administered a post-surgery injection of lactated Ringer's solution and returned to their home cages. They are carefully monitored until complete recovery from anesthesia (defined as the ability to move without significant ataxia), typically less than 10 min. Neuropathic animals are first tested 7-15 days post-surgery for tactile allodynia. During this time period, analgesic compounds are tested for their ability to reduce or eliminate these chronic pain symptoms.

Example 12: Streptozotocin-Induced Painful Diabetic Peripheral Neuropathy (PDPN) Model Male Sprague-Dawley rats were injected intraperitoneally with 50 mg/kg of streptozotocin (STZ) in sodium citrate buffer. 10% sucrose water was provided ad libitum for the first 48 hours post-STZ followed by regular drinking water.

Figure 9:
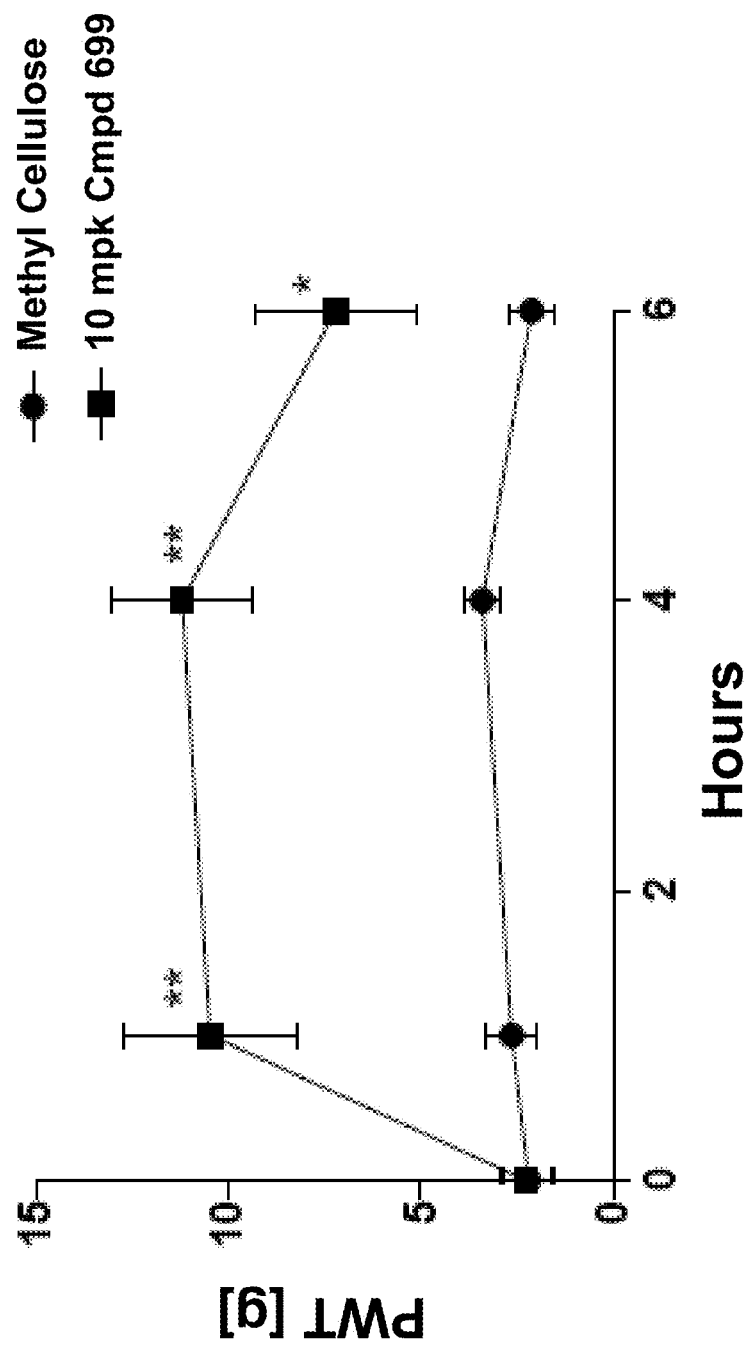
FIG. 9 shows the effect of Compound 699/Compound A (10 mpk) compared to vehicle (methyl cellulose) in the STZ-induced PDPN Model. See Example 12.
Figure 10:
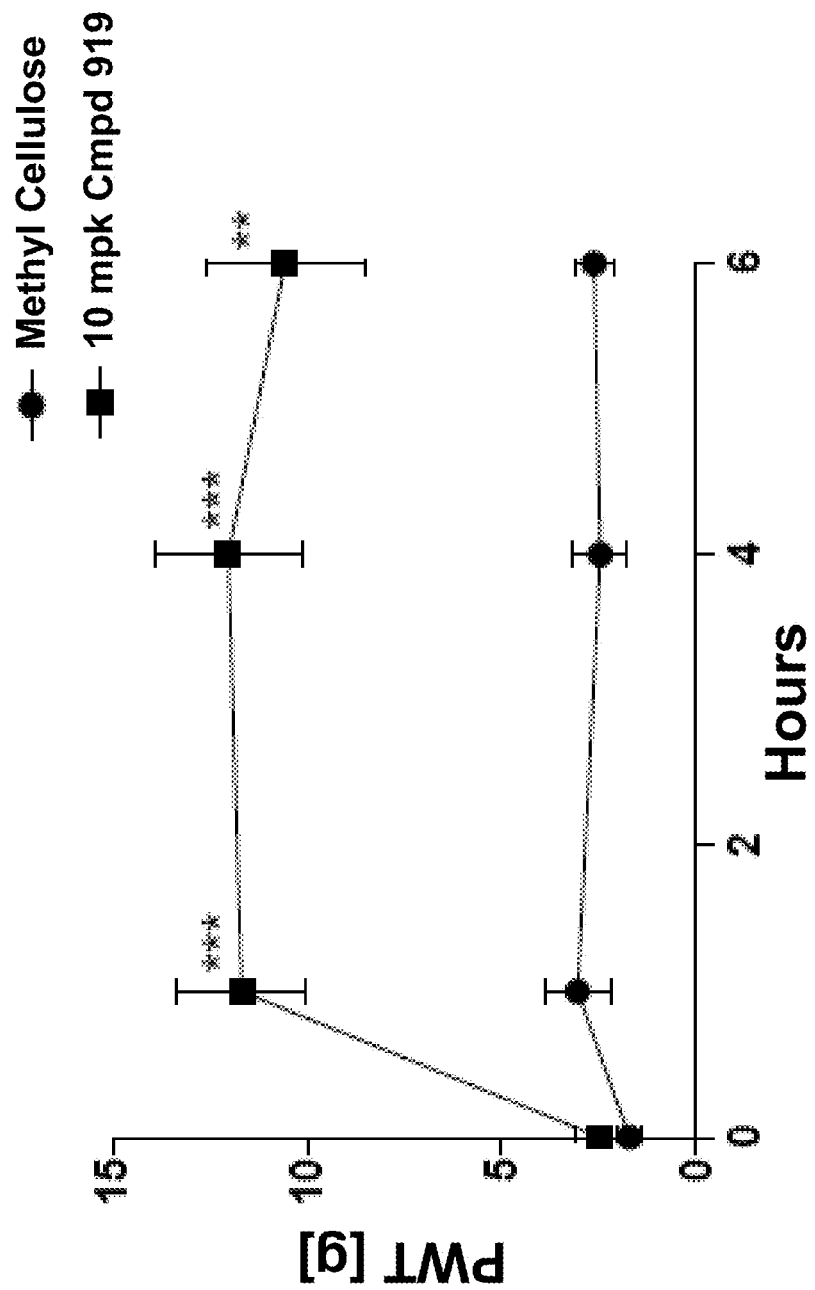
FIG. 10 shows the effect of Compound 919 (10 mpk) compared to vehicle (methyl cellulose) in the STZ-induced PDPN Model. See Example 12.

Rats were monitored once weekly for blood glucose levels and body weights. Development of tactile allodynia over time was analyzed using Von Frey filaments and a 50% withdrawal threshold was determined using Dixon's up-down procedure. The effect of $CB_2$ agonists Compound 699 and Compound 919 on pain threshold was evaluated in diabetic and allodynic rats by administering 10 mg/kg dose of either compound orally in 0.5% methylcellulose vehicle. Tactile allodynia was evaluated at 1, 4 and 6 hours post-dosing. As shown in FIG. 9 and FIG. 10, both $CB_2$ agonists Compound 699 and Compound 919 showed robust and sustained analgesic efficacy over 6 hours in this model.

Example 13: Visceral Pain Model—Writhing

In rodent pain assays, the efficacy of some $CB_2$ agonists decreases over repeated administration. A writhing model is used to evaluate the efficacy of Compound 699.

Writhing is induced in male Sprague Dawley rats by administering glacial acetic acid (1.5%) intraperitoneally (IP). Rats are administered vehicle (PO or IP), Compound 699 (3, 10, or 30 mg/kg) (0.5% MC) (PO), rimonabant (10 mg/kg) (PO) (a $CB_1$ receptor antagonist), AM630 (10 mg/kg) (PO), or morphine (1 mg/kg) (IP) for four days. On test day, rats are placed in observation cages and administered compound according to the schedules in Tables D, F, H, and J. Treatment groups are as provided in Tables E, G, I, and K.

Studies are performed to evaluate single dose assessment (Tables D and E), maintenance of efficacy after repeated administration (Tables F and G), antagonist interactions (Tables H and I), and dose response (Tables J and K).

TABLE D

| Time (min) | Activity |
|---|---|
| 0 | Rats placed in observation cages |
| 60 | Vehicle, morphine, or Compound 699 administered |
| 80 | Vehicle or acetic acid administered (1.5%, 2 mL/kg) |
| 100-130 | Writhing observation and scoring |

TABLE E

Group 1 (n = 4)

Vehicle IP
Acetic Acid 0.5%
Acetic Acid 1%
Acetic Acid 2%

Group 2 (n = 4)

Vehicle IP/Vehicle IP
Acetic Acid (1.5%)/Vehicle IP
Acetic Acid (1.5%)/Morphine (1 mg/kg)

Group 3 (n = 4)

Acetic Acid (1.5%)/Vehicle PO
Acetic Acid (1.5%)/Compound 699 (30 mg/kg)
Acetic Acid (1.5%)/Morphine (1 mg/kg)

TABLE F

| Time (min) | Activity |
|---|---|
| 0 | Rats placed in observation cages |
| 60 | Vehicle, morphine or Compound 699 administered |
| 80 | Vehicle or acetic acid administered (1.5%, 2 mL/kg) |
| 100-130 | Writhing observation and scoring |

TABLE G

| Group (n = 4) | Subchronic (4 days BID) | Acute 1 | Acute 2 |
|---|---|---|---|
| 1 | Vehicle PO | Vehicle IP | Vehicle PO |
| 2 | Vehicle PO | Acetic acid | Vehicle PO |
| 3 | Vehicle PO | Acetic acid | Compound 699 |
| 4 | Vehicle PO | Acetic acid | Morphine |
| 5 | Compound 699 | Acetic acid | Vehicle PO |
| 6 | Compound 699 | Acetic acid | Compound 699 |
| 7 | Morphine | Acetic acid | Vehicle PO |
| 8 | Morphine | Acetic acid | Morphine |

TABLE H

| Time (min) | Activity |
|---|---|
| 0 | Rats placed in observation cages |
| 60 | Vehicle or antagonists administered |
| 90 | Vehicle, morphine or Compound 699 administered |
| 110 | Vehicle or acetic acid administered (1.5%, 2 mL/kg) |
| 130-160 | Writhing observation and scoring |

TABLE I

Group (n = 6)

| | | | |
|---|---|---|---|
| 1 | Vehicle PO | Vehicle PO | Vehicle IP |
| 2 | Vehicle PO | Vehicle PO | Acetic acid |
| 3 | Vehicle PO | Morphine | Acetic acid |
| 4 | Vehicle PO | Compound 699 (10 mg/kg) | Acetic acid |
| 5 | Vehicle PO | Compound 699 (30 mg/kg) | Acetic acid |
| 6 | Rimonabant | Vehicle PO | Acetic acid |
| 7 | Rimonabant | Compound 699 (10 mg/kg) | Acetic acid |
| 8 | Rimonabant | Compound 699 (30 mg/kg) | Acetic acid |
| 9 | AM630 | Vehicle PO | Acetic acid |
| 10 | AM630 | Compound 699 (10 mg/kg) | Acetic acid |
| 11 | AM630 | Compound 699 (30 mg/kg) | Acetic acid |

TABLE J

| Time (min) | Activity |
|---|---|
| 0 | Rats placed in observation cages |
| 60 | Vehicle, morphine or Compound 699 administered |
| 80 | Saline or acetic acid administered (1.5%, 2 mL/kg) |
| 100-130 | Writhing observation and scoring |

TABLE K

Group (n = 4)

| | | |
|---|---|---|
| 1 | Vehicle (0.5% MC, PO) | Saline |
| 2 | Vehicle (0.5% MC, PO) | Acetic acid |
| 3 | Morphine (1 mg/kg) | Acetic acid |
| 4 | Compound 699 (3 mg/kg) | Acetic acid |
| 5 | Compound 699 (10 mg/kg) | Acetic acid |
| 6 | Compound 699 (30 mg/kg) | Acetic acid |

Writhing behavior is scored when a rat exhibits back arching, abdominal abduction, body stretches and/or forelimb extension. Writhing behavior is scored for 30 minutes in five-minute time bins.

Figure 11:
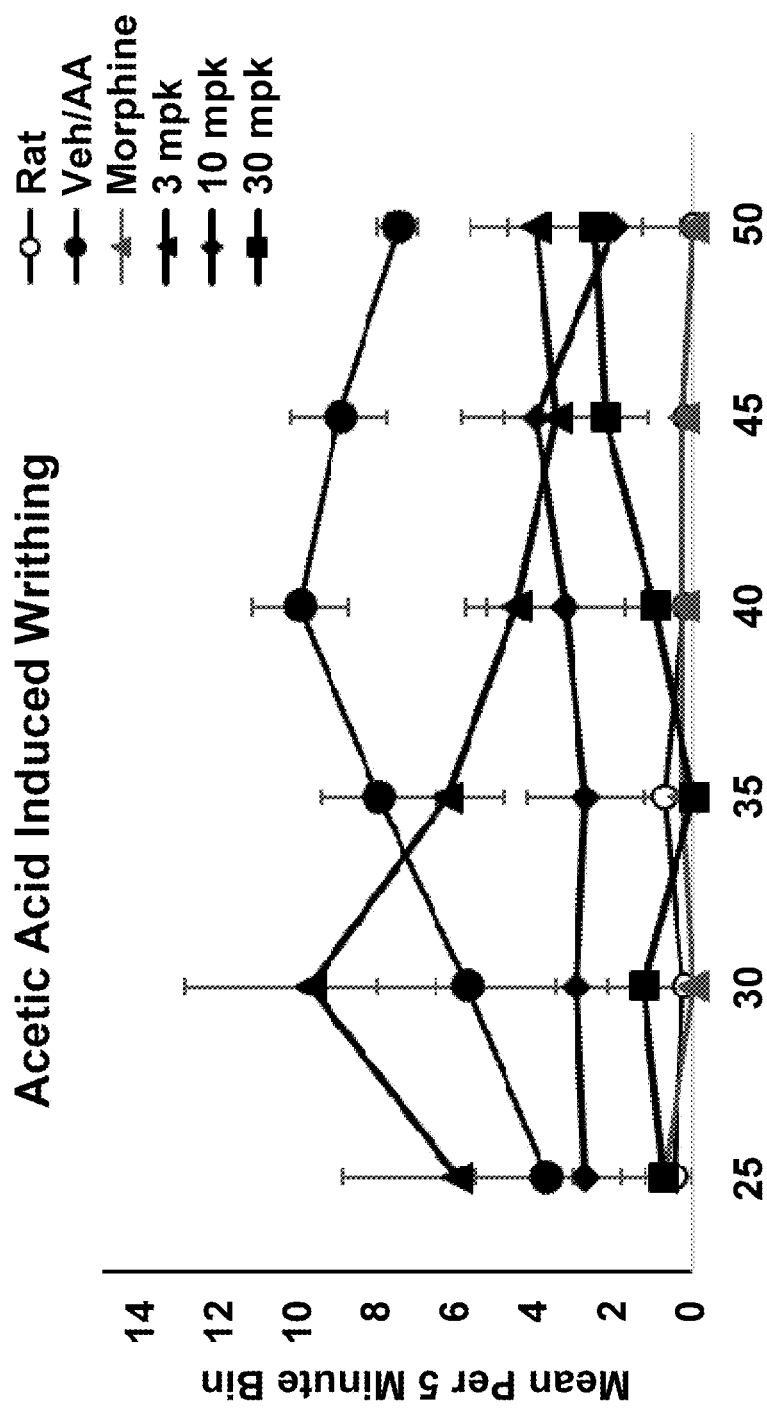
FIG. 11 shows the effect of Compound 699 in an acetic acid-induced writhing model of visceral pain. See Example 13.
Figure 12:
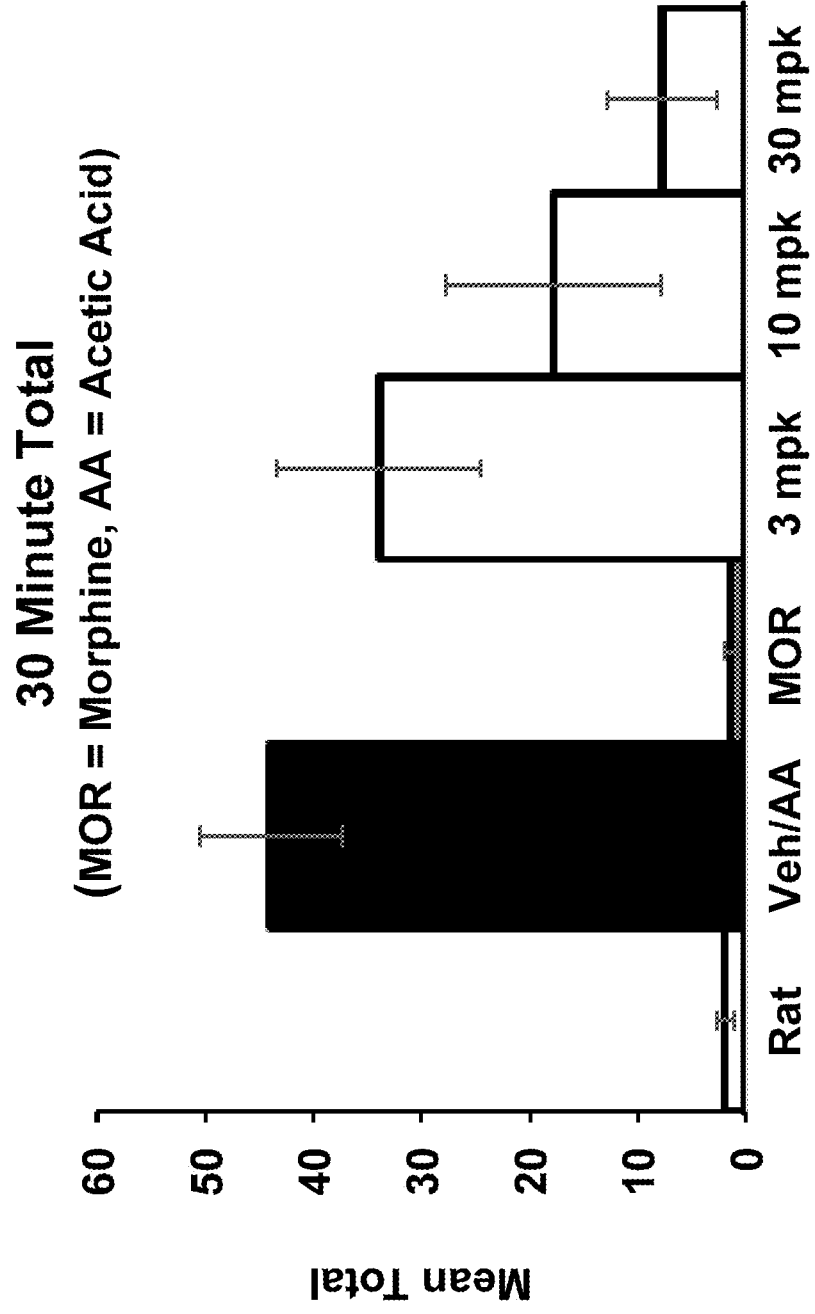
FIG. 12 shows the effect of Compound 699 in an acetic acid-induced writhing model of visceral pain. See Example 13.

For the dose response study, Sprague Dawley rats (350-430 g) were placed into individual observation cages at Time 0 and injected with vehicle, morphine (positive control), or Compound 699 one hour later. Rats then received saline or acetic acid (IP) 20 minutes after the vehicle, morphine, or Compound 699 dosing (Tables J and K). Writhing behavior was evaluated 20 minutes later and recorded for 30 minutes (in five-minute bins). Results are shown in FIGS. 11 and 12.

The data show that Compound 699 is efficacious in a writhing model for visceral pain.

Example 14: Visceral Pain Model—Colitis

Rats with active colitis display allodynia and hyperalgesia to colorectal distension following the administration of trinitrobenzene sulfonic acid (TNBS). Rats with active colitis (4 days after TNBS) induced by intracolonic TNBS are administered Compound 699 to determine whether Compound 699 reduces visceral pain response.

Healthy rats were treated twice daily with an oral gavage of one of the following for five days: 1.) vehicle (n=11); or 2.) 30 mg/kg Compound 699 (n=8). Abdominal electromyographic (EMG) electrode implantation is followed by measurement of visceromotor response (VMR) at 0, 20, 40, 60, and 80 mmHg of colorectal distention on day 4. The effect of each treatment on colonic compliance is also determined.

Figure 13:
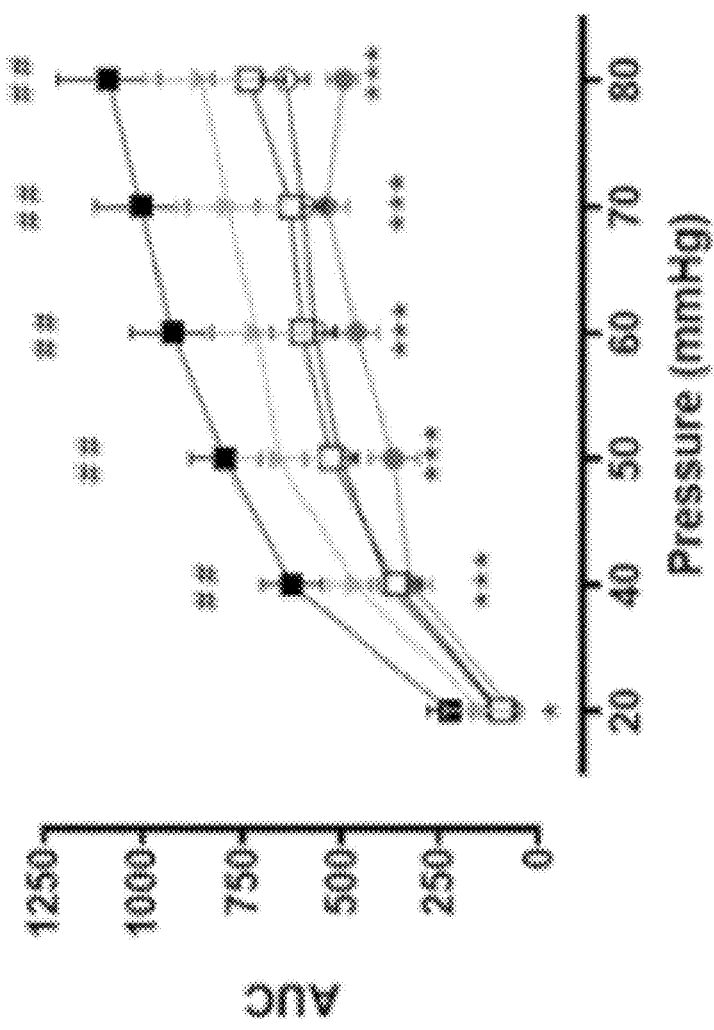
FIG. 13 shows the effect of Compound 699 in a visceral pain model of colitis. More specifically.

Rats with induced colitis were treated twice daily with an oral gavage of one of the following for five days, commencing 1 day before TNBS administration: 1.) vehicle (n=12); 2.) 10 mg/kg Compound 699 (n=9); or 3.) 30 mg/kg/ Compound 699 (n=9). Abdominal EMG electrode implantation is followed by measurement of VMR at 0, 20, 40, 60, and 80 mmHg of colorectal distention on day 4. The effect of each treatment on colonic compliance is also determined. Results are shown in FIG. 13.

These data show that Compound 699 reduces the visceral pain response in rats with TNBS-induced colitis, reducing colonic hypersensitivity in a dose-dependent manner without changing response in rats with healthy colons.

Example 15: Clinical Trial

A randomized, open-label, parallel Phase 2a study is conducted to determine the tolerability, pharmacokinetics, and efficacy of Compound 699 in subjects with Crohn's disease (CD) experiencing abdominal pain. The study population consists of adult male and female subjects aged 18 to 80 years who are diagnosed with abdominal pain due to quiescent to mildly active inflammatory Crohn's disease, as defined by a weekly average abdominal pain score (AAPS) ≥4, with minimal intestinal inflammation, confirmed with a simple endoscopic score (–CD) score<10 or fecal calprotectin<500 mcg/g. Endoscopy results obtained up to one month prior to screening may be utilized.

Eligible subjects enter a screening period of up to four weeks and are randomized in a 1:1 ratio into the study, receiving Compound 699 in oral doses of 25 mg three times daily (TID) or 100 mg capsules TID for 8 weeks. If subjects experience hypotensive symptoms and/or heart rate changes during the trial, they may be administered 50 mg TID (rather than 100 mg TID) or 25 mg BID (rather than 25 mg TID).

The analgesic effect of Compound 699 on abdominal pain is scored by subjects in a diary twice daily during screening and three times daily during treatment using an 11-point numeric rating scale from 0 (no abdominal pain) to 10 (worst possible abdominal pain). Additional efficacy assessments include achievement of clinical improvement (defined as a two-component PRO score (stool frequency and abdominal pain) of <11), clinical response from baseline to week 8, and change from baseline in C-reactive protein and fecal calprotectin at weeks 4 and 8.

A key objective of the study is to assess the tolerability and safety of Compound 699 in subjects with Crohn's disease experiencing abdominal pain. Additional objectives include:

the determination of pharmacokinetic (PK) profiles (including metabolites) and average PK parameters ($C_{max}$, $T_{max}$, $AUC_{0-8}$);

the change in abdominal pain score (APS) from pre-dose (trough) to 1.5 hours post-dose (peak) following the first of three daily doses;

the change in average abdominal pain score (AAPS) from baseline to week 8;

the proportion of subjects who are weekly responders;

the proportion of subjects who are end-of-treatment responders;

the number of pain-free days per week based on responses to the APS;

the change in CD-patient-reported-outcome (PRO) domain scores from baseline to week 8;

the change in Crohn's disease activity index (CDAI) from baseline to week 8;

frequency of pain medication use;

reduction in C-reactive protein (CRP) levels at weeks 4 and 8;

the change in Patient Health Questionnaire-9 (PHQ-9) score between screening, week 4, and week 8; and reduction in fecal calprotectin levels at week 4 and week 8.

Those skilled in the art will recognize that various modifications, additions, substitutions, and variations to the illustrative examples set forth herein can be made without departing from the spirit of the invention and are, therefore, considered within the scope of the invention.

What is claimed is:

1. A method for treating or alleviating visceral pain selected from the group consisting of pelvic pain, painful bladder syndrome, or pain associated with: pancreatitis, chronic pancreatitis, endometriosis, interstitial cystitis, interstitial cystitis induced by chemotherapy, ulcerative interstitial cystitis, nonulcerative interstitial cystitis, autoimmune interstitial cystitis, prostatitis, chronic prostatitis, or postsurgical abdominal lesion in a patient in need of such treatment, comprising administering to the patient a therapeutically effective amount of a compound selected from compounds of Formula Ia and pharmaceutically acceptable salts and N-oxides thereof:

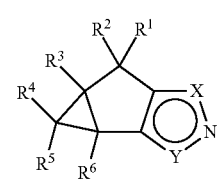

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O)N(R^8)R^9$; or
X is $CC(O)N(R^8)R^9$ and Y is $NR^7$;

$R^7$ is $-R^{10}-R^{11}-R^{12}-R^{13}$; wherein:
$R^{10}$ is selected from: $C_1$-$C_6$ alkylene, heteroarylene, and heterocyclylene; or $R^{10}$ is absent;
$R^{11}$ is selected from: $-C(O)NH-$ and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is $-R^{14}-R^{15}-R^{16}-R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: $-C(O)NH-$, $-C(O)-$, $-C(O)O-$, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

2. The method according to claim 1, wherein the compound of Formula Ia is selected from compounds of Formula Ic and pharmaceutically acceptable salts, and N-oxides thereof:

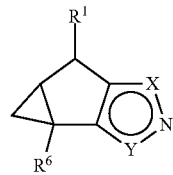

Ic wherein:
$R^1$ and $R^6$ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$;
$R^7$ is $-R^{10}-R^{11}-R^{12}-R^{13}$; wherein:
$R^{10}$ is selected from: $C_1$-$C_6$ alkylene, heteroarylene, and heterocyclylene; or $R^{10}$ is absent;
$R^{11}$ is selected from: $-C(O)NH-$ and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is $-R^{14}-R^{15}-R^{16}-R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: $-C(O)NH-$, $-C(O)-$, $-C(O)O-$, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

3. The method according to claim 1, wherein the compound of Formula Ia is selected from compounds of Formula Ie and pharmaceutically acceptable salts, and N-oxides thereof:

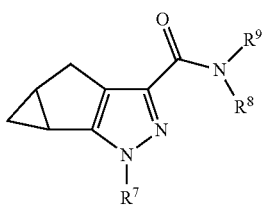

Ie wherein:
$R^7$ is —$R^{10}$—$R^{11}$—$R^{12}$—$R^{13}$; wherein:
$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;
$R^{11}$ is selected from: —C(O)NH— and methylene; or $R^{11}$ is absent;
$R^{12}$ is methylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;
$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl; or $R^{14}$ is absent;
$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl; or $R^{15}$ is absent;
$R^{16}$ is selected from: ethylene and methylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarbonyl, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methylpyrrolidinyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

4. The method of claim 1, wherein the compound of Formula Ia is selected from the following compounds and pharmaceutically acceptable salts, and N-oxides thereof:

(1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

(1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

(1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide;

(1aR,5aR)-2-Pyrazin-2-yl-1a,2,5,5a-tetrahydro-1H-2,3-diaza-cyclopropa[a]pentalene-4-carboxylic acid tert-butylamide;

(1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

(1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

(1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester;

(1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

(S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

(1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

(1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

(1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide;

(1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

(1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

(1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

(1aS,5aS)-2-(4-Oxy-pyrazin-2-yl)-1a,2,5,5a-tetrahydro-H-2,3-diaza-cyclopropa[a]pentalene-4-carboxylic acid ((S)-2-hydroxy-1-phenyl-ethyl)-amide;

(1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide;

(1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;

(1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;

(1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

5. The method of claim 1, wherein the compound of Formula Ia is (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound A), having the structure:

Compound A

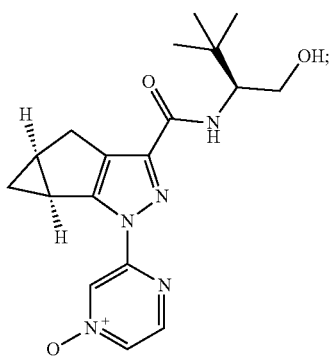

or a pharmaceutically acceptable salt or crystal form thereof.

6. The method according to claim 5, wherein the patient is administered a dose from 10 mg to 500 mg of Compound A.

7. The method according to claim 5, wherein the patient is administered a dose from 10 mg to 400 mg of Compound A.

8. The method according to claim 5, wherein the patient is administered a dose of 25 mg, 50 mg, or 100 mg of Compound A.

9. The method according to claim 6, wherein the dose is administered once, twice, or three times per day.

10. The method according to claim 5, wherein Compound A is administered in a pharmaceutical composition comprising Compound A and a pharmaceutically acceptable carrier.

11. A method for activating a $CB_2$ receptor in a patient experiencing visceral pain selected from the group consisting of pelvic pain, painful bladder syndrome, or pain associated with: pancreatitis, chronic pancreatitis, endometriosis, interstitial cystitis, interstitial cystitis induced by chemotherapy, ulcerative interstitial cystitis, nonulcerative interstitial cystitis, autoimmune interstitial cystitis, prostatitis, chronic prostatitis, or post-surgical abdominal lesion, comprising administering to the patient a therapeutically effective amount of a compound selected from compounds of Formula Ia and pharmaceutically acceptable salts and N-oxides thereof:

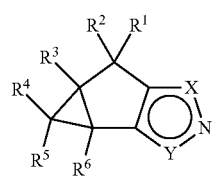

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O)N(R^8)R^9$; or
X is $CC(O)N(R^8)R^9$ and Y is $NR^7$;
$R^7$ is —$R^{10}$—$R^{11}$—$R^{12}$—$R^{13}$; wherein:
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or $R^{11}$ is absent;
$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

12. The method according to claim 1, wherein the patient has a visual analogue scale pain score of ≥40 mm.

13. The method according to claim 11, wherein the compound of Formula Ia is (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethylpropyl)-amide (Compound A), having the structure:

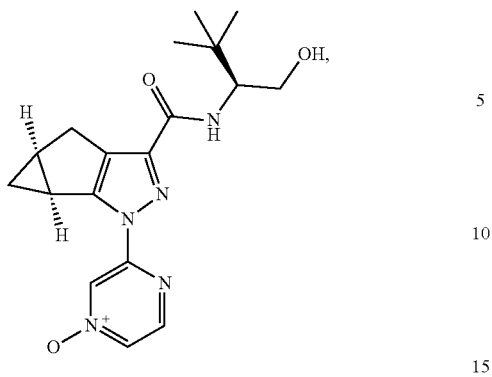
or a pharmaceutically acceptable salt or crystal form thereof.
\* \* \* \* \*